US007977466B2

(12) United States Patent
Imamura et al.

(10) Patent No.: US 7,977,466 B2
(45) Date of Patent: *Jul. 12, 2011

(54) C-GLYCOSIDE DERIVATIVES AND SALTS THEREOF

(75) Inventors: Masakazu Imamura, Tokyo (JP); Takeshi Murakami, Tokyo (JP); Ryota Shiraki, Tokyo (JP); Kazuhiro Ikegai, Tokyo (JP); Takashi Sugane, Tokyo (JP); Fumiyoshi Iwasaki, Tokyo (JP); Eiji Kurosaki, Tokyo (JP); Hiroshi Tomiyama, Tokyo (JP); Atsushi Noda, Tokyo (JP); Kayoko Kitta, Chikuma (JP); Yoshinori Kobayashi, Chikuma (JP)

(73) Assignees: Astellas Pharma Inc., Tokyo (JP); Kotobuki Pharmaceutical Co., Ltd., Nagano (JP)

( * ) Notice: Subject to any disclaimer, the term of this patent is extended or adjusted under 35 U.S.C. 154(b) by 327 days.

This patent is subject to a terminal disclaimer.

(21) Appl. No.: 12/173,614

(22) Filed: Jul. 15, 2008

(65) Prior Publication Data

US 2009/0069252 A1     Mar. 12, 2009

Related U.S. Application Data

(62) Division of application No. 11/710,434, filed on Feb. 26, 2007, now Pat. No. 7,772,407, which is a division of application No. 10/541,615, filed as application No. PCT/JP2004/003324 on Mar. 12, 2004, now Pat. No. 7,202,350.

(30) Foreign Application Priority Data

Mar. 14, 2003   (JP) .................................. 2003-070297

(51) Int. Cl.
*A61K 31/7034* (2006.01)
*C07H 7/04* (2006.01)

(52) U.S. Cl. ........................................ 536/1.11; 514/23

(58) Field of Classification Search .................. None
See application file for complete search history.

(56) References Cited

U.S. PATENT DOCUMENTS

| 6,617,313 | B1 | 9/2003 | Maurya et al. | |
| 6,936,590 | B2 * | 8/2005 | Washburn et al. | 514/25 |
| 7,202,350 | B2 * | 4/2007 | Imamura et al. | 536/1.11 |
| 7,772,407 | B2 * | 8/2010 | Imamura et al. | 549/48 |
| 2001/0041674 | A1 | 11/2001 | Tomiyama et al. | |
| 2005/0032711 | A1 | 2/2005 | Patel et al. | |
| 2005/0032712 | A1 | 2/2005 | Urbanski | |
| 2005/0037980 | A1 | 2/2005 | Rybczynski et al. | |
| 2005/0037981 | A1 | 2/2005 | Beavers et al. | |
| 2005/0124555 | A1 | 6/2005 | Tomiyama et al. | |
| 2005/0233988 | A1 | 10/2005 | Nomura et al. | |
| 2009/0143316 | A1 * | 6/2009 | Imamura et al. | 514/25 |
| 2010/0094025 | A1 * | 4/2010 | Komenoi et al. | 549/58 |

FOREIGN PATENT DOCUMENTS

| JP | 6-199695 | 7/1994 |
| JP | 2001-288178 | 10/2001 |
| WO | WO 98/31697 | 7/1998 |
| WO | WO 01/27128 | 4/2001 |
| WO | WO 03/082887 | 10/2003 |
| WO | WO 03/087093 | 10/2003 |
| WO | WO 03/094928 | 11/2003 |
| WO | WO 2004/013118 | 2/2004 |
| WO | WO 2004/080990 | 9/2004 |
| WO | WO 2005/012326 | 10/2005 |
| WO | WO 2006/011502 | 2/2006 |

OTHER PUBLICATIONS

U.S. Appl. No. 12/865,634, filed Jul. 2010, Eiji et al.*
Chinese Office Action dated Jan. 15, 2010 as issued in Chinese Patent Application No. 2004800067612 with partial English translation.
Korean Office Action dated Dec. 17, 2009 as issued in Korean Patent Application No. 10-2008-7015323 with partial English translation.
Korean Office Action dated Dec. 17, 2009 as issued in Korean Patent Application No. 10-2005-7017126 with partial English translation.
Todoulou, et al., "Synthesis and antiviral activity of some new 1H-1,2,4-triazole derivaties," European Journal of Medicinal Chemistry, 1994, pp. 611-620, vol. 29, No. 7-8.
Buchanan, et al., "Synthesis of C-Glycosyltetrazoles Related to 3-Deoxy-D-arabino-heptulosonic Acid 7-Phosphate (DAHP); Potential Inhibitors of Early Steps in the Shikimate Pathway," Journal of the Chemical Soociety, Oct. 21, 1992, pp. 2593-2601, No. 20.
Varma, et al., "Inhibition of Lens Aldose Reductase by Flavonoids— Their Possible Role in the Prevention of Diabetic Cataracts," Biochemical Pharmacology, Nov. 15, 1976, pp. 2505-2513, vol. 25, No. 22.
Andrade-Cetto, et al., "Hypoglycemic effect of Cecropia obtusifolia on streptozotocin diabetic rats," Journal of Ethno-Pharmacology, Dec. 2001, pp. 145-149, vol. 78, Nos. 2-3.
Shen, et al., "Hypoglycemic Effects of the Combined Use of Puerarin and Aspirin in Mice," Acta Pharmaccutica Sinica, 1985, pp. 863-865.
A. I. Rybachenko et al, "Basicity constants of natural isoflavonoids", Database CAPLUS Chemical Abstracts Service, 1986; pp. 773-775.
Toshihiro Kumazawa et al, "Cleavage of the C-C linkage between the sugar and the aglycon in *C*-glycosylphloroacetophenone, and.the NMR spectral characteristics of the resulting di-C-glycosyl compound", Carbohydrate Research, vol. 334, pp. 207-213, 2001.
Toshihiro Kumazawa et al, "Synthesis of 1-[3,5-bis-(2,3,4,6-tetra-0-acetyl-β-D-glucopyranosyl)-2,4,6-trihydroxyphenyl]ethanone: An intermediate of potential usefulness for synthesis of bis-C-glucosyl flavonoids", Carbohydrate Research, vol. 297, pp. 379-383, 1997.
Takeshi Kuribayashi et al, "The Sequential Double Aryl C-Glycosidation: Introduction of a Second Sugar Unit onto Mono Aryi C-Glycosides using SnCl4/AgOTfa", Tetrahedron Letters, vol. 39, pp. 4541-4542, 1998.
Emad El Telbani et al, "Synthesis of bis(C-glycosyl)flavonoid precursors", Carbohydrate Research, vol. 306, pp. 463-467, 1998.
Frank Cullmann et al, "Chemistry and Biology of Moss. 140. Lignans from the liverwort *Lepicolea ochroleuca*", Phytochemistry, vol. 52, pp. 1651-1656, 1999.
S.M. Jain et al, "Synthesis and antiinflammatory activity of glycosidated 4-aryl-1,4-dihydropyridines", Indian Journal of Chemistry, vol. 29B, pp. 95-97, 1990.

* cited by examiner

*Primary Examiner* — Eric S Olson
(74) *Attorney, Agent, or Firm* — Sughrue Mion, PLLC

(57) ABSTRACT

The present invention provides C-glycoside derivatives and salts thereof, wherein B ring is bonded to A ring via —X— and A ring is directly bonded to the glucose residue, and it is usable as a $Na^+$-glucose cotransporter inhibitor, especially for a therapeutic and/or preventive agent for diabetes such as insulin-dependent diabetes (type 1 diabetes) and insulin-independent diabetes (type 2 diabetes), as well as diabetes related diseases such as an insulin-resistant diseases and obesity.

7 Claims, No Drawings

C-GLYCOSIDE DERIVATIVES AND SALTS THEREOF

CROSS-REFERENCE TO RELATED APPLICATIONS

This application is a divisional application of U.S. application Ser. No. 11/710,434, now U.S. Pat. No. 7,772,407, filed Feb. 26, 2007, which is a divisional application of U.S. application Ser. No. 10/541,615, now U.S. Pat. No. 7,202,350, filed Jul. 7, 2005, which is a national stage application of PCT/JP2004/003324, filed Mar. 12, 2004, which claims priority to foreign application JP 2003-070297, filed Mar. 14, 2003.

FIELD OF THE INVENTION

The present invention relates to C-glycoside derivatives and salts thereof. More particularly, the present invention relates to C-glycoside derivatives and salts thereof useful as a $Na^+$-glucose cotransporter inhibitor. C-glycoside derivatives and salts thereof of the present invention are useful for treatment of various diabetes-related diseases inclusive of insulin-dependent diabetes (type 1 diabetes), insulin-independent diabetes (type 2 diabetes), insulin-resistant diseases and obesity, and the prevention of these diseases.

BACKGROUND OF THE INVENTION

In recent years, a medicine to inhibit glucose-reabsorption by $Na^+$-glucose cotransporters (SGLT) in the intestinal tract and kidney (a $Na^+$-glucose cotransporter inhibitor) has been demanded as an antidiabetic agent to rapidly normalize hyperglycemia and improve the energy balance in the body. Such a $Na^+$-glucose cotransporter inhibitor has been expected as an excellent agent for treating or preventing various diabetes-related diseases such as insulin-dependent diabetes (type 1 diabetes) and insulin-independent diabetes (type 2 diabetes), as well as insulin-resistant diseases and obesity.

As compounds used for the $Na^+$-glucose cotransporter inhibitor, phloridzin described in Welch, C. A. et al. (J. Natr., 1989, 119(11) 1698) and synthetic O-glycoside derivatives described in Hongu, M. et al. (Chem. Pharm. Bull., 1998, 46(1) 22) and JP-A-11-21243 are known, for example. These compounds are reported to discharge excess blood glucose into urine and reduce blood glucose level by inhibiting glucose-reabsorption by $Na^+$-glucose cotransporters in the intestinal tract or in the kidney.

However, because any of these compounds is an O-glycoside derivative comprising an O-glucoside bond formed between glucose and an aglycon moiety, it has a problem that the inhibition effect is reduced due to hydrolysis of O-glucoside bond by glucosidase or the like in the small intestine when orally absorbed.

In addition, in the case of phloridin, phloretin, which is an aglycon moiety of phloridin, is known as a strong inhibitor for a facilitated diffusion-type glucose transporter. For example, it is reported that the cerebral glucose concentration decreases when phloretin is administered to the vein of a rat (e.g. Stroke, 1983, 14, 388). Phloretin is also known as an inhibitor of a vitamin C transporter (Wang, Y. et al., Biochem. Biophys. Res. Commun., 2000, 267, 488-494).

Therefore, an attempt has been made to use a C-glycoside prepared by converting oxygen in the glucoside bond of the O-glycoside to carbon as the $Na^+$-glucose cotransporter inhibitor.

For example, JP-A-2001-288178 (Patent Document 1) describes that compounds of the following formula are effective in inhibiting $Na^+$-glucose cotransporters and are useful as a treating agent or preventing agent for diabetes and a hypoglycemic agent.

(Chemical Formula)

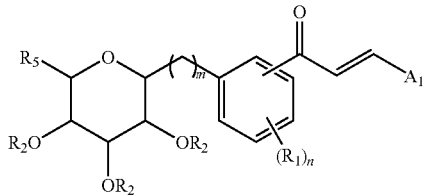

wherein $R^1$ represents H, OH, lower alkyl group, —O-lower alkyl group, or the like; $R^2$ represents H, —COO-lower alkyl group, or the like; $R^5$ represents —$CH_2OH$, —$CH_2OCOO$-lower alkyl group, or the like; $A_1$ represents pyridine, furan, thiophene, quinoline, indole, or the like; n is 0, 1, 2, or 3, and m is 0 or 1 (See Patent Document 1 for further details on the symbols of the above formula).

In addition, the pamphlet of WO 01/27128 (Patent Document 2) describes that a compound of the following formula can be used as the $Na^+$-glucose cotransporter inhibitor to treat obesity or type 2 diabetes.

(Chemical Formula)

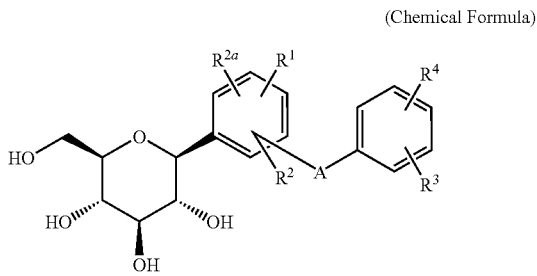

wherein $R^1$, $R^2$, and $R^{2a}$ individually represent a hydrogen atom, OH, $OR^5$, alkyl, $CF_3$, $OCHF_2$, $OCF_3$, or the like; $R^3$ and $R^4$ individually represent a hydrogen atom, OH, $OR^{5a}$, —O-aryl, —O—$CH_2$-aryl, alkyl, cycloalkyl, $CF_3$, or the like; A represents O, S, NH, or $(CH_2)_n$, and n is 0, 1, 2, or 3 (See Patent Document 2 for further details on the symbols of the above formula).

As explained above, the C-glycoside derivatives are useful to a certain extent for treating diabetes due to the effect of inhibiting a $Na^+$-glucose cotransporter. However, due to the recent rise in incidence of diabetes which is a lifestyle-related disease and could even be called one of the most popular diseases in Japan, compounds having a chemical structure different from that of known compounds and showing the effect of inhibiting $Na^+$-glucose cotransporters more rapidly and more significantly have been increasingly desired for the clinical practice of diabetes treatment or the like.

DISCLOSURE OF THE INVENTION

The present inventors have found that C-glycoside derivatives, which have B ring ((1) a saturated or an unsaturated eight to ten-membered bicyclic hetero ring having 1 to 4 hetero atom(s) selected from N, S, and O, (2) a saturated or an unsaturated five or six-membered monocyclic hetero ring having 1 to 4 hetero atom(s) selected from N, S, and O, (3) a saturated or an unsaturated eight to ten-membered bicyclic hydrocarbon ring, or (4) a benzene ring) bonded to A ring ((1) a benzene ring, (2) a five or six-membered monocyclic heteroaryl ring having 1 to 4 hetero atom(s) selected from N, S, and O, or (3) a saturated or an unsaturated eight to ten-membered bicyclic hetero ring having 1 to 4 hetero atom(s) selected from N, S, and O) via —X— (a bond or lower alkylene), with the A ring being directly bonded to a glucose residue (wherein A ring, B ring, and X have a correlation that (1) when A ring is a benzene ring, B ring is a ring other than a benzene ring or that (2) when A ring is a benzene ring, and B ring is a saturated or an unsaturated eight to ten-membered bicyclic hetero ring having 1 to 4 hetero atom(s) selected from N, S, and O including a benzene ring, or a saturated or an unsaturated eight to ten-membered bicyclic hydrocarbon ring including a benzene ring, X is bonded to the B ring in a part other than the benzene ring included in the B ring), shown by the following formula (I), has a significant effect of inhibiting a Na$^+$-glucose cotransporter, thereby the present invention has been achieved. That is, the present invention relates to compounds shown by the following formula (I) or salts thereof (hereinafter both sometimes referred to as "compound of the present invention"). The compound of the present invention can be suitably used as a Na$^+$-glucose cotransporter inhibitor using the compound as an active ingredient, particularly as a therapeutic agent or preventive agent for diabetes.

The chemical structure of the compound of the present invention differs from those of Patent Documents 1 and 2 in that the A ring and the B ring of the compound of the present invention cannot be benzene rings at the same time. That is, the present invention provides a Na$^+$-glucose cotransporter inhibitor having a new structure.

Specifically, the present invention provides C-glycoside derivatives described bellow, pharmaceutically acceptable salts thereof, pharmaceutical compositions containing these compounds, use of these compounds for producing a Na$^+$-glucose cotransporter inhibitor or an antidiabetic agent, and methods for treating diabetes.

[1] C-glycoside derivatives of the following formula (I) and salts thereof:

[Chemical Formula]

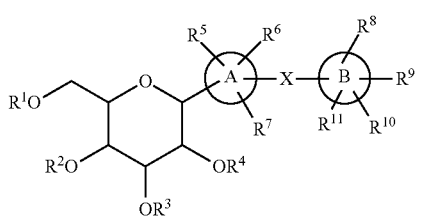

(I)

wherein A ring represents (1) a benzene ring, (2) a five or six-membered monocyclic heteroaryl ring having 1 to 4 hetero atom(s) selected from N, S, and O, or (3) a saturated or an unsaturated eight to ten-membered bicyclic hetero ring having 1 to 4 hetero atom(s) selected from N, S, and O;

B ring represents (1) a saturated or an unsaturated eight to ten-membered bicyclic hetero ring having 1 to 4 hetero atom(s) selected from N, S, and O, (2) a saturated or an unsaturated five or six-membered monocyclic hetero ring having 1 to 4 hetero atom(s) selected from N, S, and O, (3) a saturated or an unsaturated eight to ten-membered bicyclic hydrocarbon ring, or (4) a benzene ring;

X represents a bond or lower alkylene;

(wherein A ring, B ring, and X have a correlation that (1) when A ring is a benzene ring, B ring is a ring other than a benzene ring or that (2) when A ring is a benzene ring, and B ring is a saturated or an unsaturated eight to ten-membered bicyclic hetero ring having 1 to 4 hetero atom(s) selected from N, S, and O including a benzene ring, or a saturated or an unsaturated eight to ten-membered bicyclic hydrocarbon ring including a benzene ring, X is bonded to the B ring in a part other than the benzene ring included in the B ring: Incidentally, this correlation specifically means that the A ring and the B ring cannot be benzene rings simultaneously and that when the A ring is a benzene ring and the B ring is benzofuran or indane, X is not a benzene ring constituting a part of the B ring but bonds with a furan ring or a cyclopentane ring.)

$R^1$ to $R^4$ individually represent a hydrogen atom, a lower alkyl, —C(=O)-lower alkyl, or -lower alkylene-aryl; and $R^5$ to $R^{11}$ individually represent a hydrogen atom, a lower alkyl, a cycloalkyl, a halogen, a halogen-substituted lower alkyl, —OH, =O, —NH$_2$, lower alkyl sulfonyl-, halogen-substituted lower alkyl sulfonyl-, aryl sulfonyl-, an aryl, a saturated or an unsaturated five or six-membered monocyclic hetero ring having 1 to 4 hetero atom(s) selected from N, S, and O, -lower alkylene-OH, -lower alkylene-O-lower alkyl, -lower alkylene-O—C(=O)-lower alkyl, -lower alkylene-O-lower alkylene-COOH, -lower alkylene-O-lower alkylene-C(=O)—O-lower alkyl, -lower alkylene-NH$_2$, -lower alkylene-NH-lower alkyl, -lower alkylene-N(lower alkyl)$_2$, -lower alkylene-NH—C(=O)-lower alkyl, —COOH, —CN, —C(=O)—O-lower alkyl, —C(=O)—NH$_2$, —C(=O)—NH-lower alkyl, —C(=O)—N(lower alkyl)$_2$, —O-lower alkyl, —O-cycloalkyl, —O-lower alkylene-OH, —O-lower alkylene-O-lower alkyl, —O-lower alkylene-COOH, —O-lower alkylene-C(=O)—O-lower alkyl, —O-lower alkylene-C(=O)—NH$_2$, —O-lower alkylene-C(=O)—NH-lower alkyl, —O-lower alkylene-C(=O)—N(lower alkyl)$_2$, —O-lower alkylene-CH(OH)—CH$_2$(OH), —O-lower alkylene-NH$_2$, —O-lower alkylene-NH-lower alkyl, —O-lower alkylene-N(lower alkyl)$_2$, —O-lower alkylene-NH—C(=O)-lower alkyl, —NH-lower alkyl, —N(lower alkyl)$_2$, —NH—SO$_2$-lower alkyl, —NH—SO$_2$-halogen-substituted lower alkyl, —NH-lower alkylene-OH, —NH—C(=O)-lower alkyl, —NH—C(=O)—NH$_2$, —NH—C(=O)—NH-lower alkyl, —NH—C(=O)—N(lower alkyl)$_2$, or, —NH—C(=O)—O-lower alkyl;

wherein —N(lower alkyl)$_2$ in $R^5$ to $R^{11}$ includes the case of being constituted by different lower alkyls besides the case of being constituted by the same lower alkyl. —N(lower alkyl)$_2$ includes, for example, a methylethylamino group.

[2] C-Glycoside derivatives and the salts thereof according to the above [1], wherein the A ring in the formula (I) is (1) a benzene ring or (2) a five or six-membered monocyclic heteroaryl ring having 1 to 4 hetero atom(s) selected from N, S, and O.

[3] C-Glycoside derivatives and the salts thereof according to the above [2], wherein the B ring in the formula (I) is (1) a saturated or an unsaturated eight to ten-membered bicyclic hetero ring having 1 to 4 hetero atom(s) selected from N, S, and O or (2) a saturated or an unsaturated five or six-membered monocyclic hetero ring having 1 to 4 hetero atom(s) selected from N, S, and O.

[4] C-Glycoside derivatives and the salts thereof according to the above [3], wherein the A ring in the formula (I) is a benzene ring and the B ring is a saturated or an unsaturated eight to ten-membered bicyclic hetero ring having 1 to 4 hetero atom(s) selected from N, S, and O.

[5] C-Glycoside derivatives and the salts thereof according to the above [4], wherein the X in the formula (I) is methylene.

[6] C-Glycoside derivatives and the salts thereof according to the above [5], wherein the $R^1$ to $R^4$ in the formula (I) are hydrogen atoms.

[7] C-Glycoside derivatives and the salts thereof according to the above [1], wherein the C-glycoside derivative of the formula (I) is at least one compound selected from the group consisting of (1S)-1,5-anhydro-1-[3-(1-benzothien-2-ylmethyl)phenyl-D-glucitol, (1S)-1,5-anhydro-1-[5-(1-benzothien-2-ylmethyl)-2-hydroxyphenyl]-D-glucitol, (1S)-1,5-anhydro-1-[5-(1-benzothien-2-ylmethyl)-2-methoxyphenyl]-D-glucitol, (1S)-1,5-anhydro-1-[5-(1-benzothien-2-ylmethyl)-2-(2-hydroxyethoxy)phenyl]-D-glucitol, (1S)-1,5-anhydro-1-[5-(1-benzothien-2-ylmethyl)-2-(methylamino)phenyl]-D-glucitol, (1S)-1,5-anhydro-1-{5-(1-benzothien-2-ylmethyl)-2-[(2-hydroxyethyl)amino]phenyl}-D-glucitol, (1S)-1,5-anhydro-1-[5-(1-benzothien-2-ylmethyl)-4-methoxyphenyl]-D-glucitol, (1S)-1,5-anhydro-1-[5-(1-benzothien-2-ylmethyl)-4-chlorophenyl]-D-glucitol, (1S)-1,5-anhydro-1-[5-(1-benzothien-2-ylmethyl)-4-fluorophenyl]-D-glucitol, (1S)-1,5-anhydro-1-[5-(1-benzothien-2-ylmethyl)-2,4-dimethoxy phenyl]-D-glucitol, (1S)-1,5-anhydro-1-[5-(1-benzothien-2-ylmethyl)-4-chloro-2-methoxyphenyl]-D-glucitol, (1S)-1,5-anhydro-1-[5-(1-benzothien-2-ylmethyl)-4-chloro-2-hydroxyphenyl]-D-glucitol, (1S)-1,5-anhydro-1-[5-(1-benzothien-2-ylmethyl)-4-fluoro-2-hydroxyphenyl]-D-glucitol, and (1S)-1,5-anhydro-1-[5-(1-benzothien-2-ylmethyl)-4-fluoro-2-methoxyphenyl]-D-glucitol.

[8] A pharmaceutical composition containing a C-glycoside derivative or a salt thereof according to any one of the above [1] to [7].

[9] A pharmaceutical composition according to the above [8], wherein the composition is a $Na^+$-glucose cotransporter inhibitor.

[10] A pharmaceutical composition according to the above [8], wherein the composition is an antidiabetic agent.

[11] Use of the C-glycoside derivatives and the salts thereof according to any one of the above [1] to [7] for producing a $Na^+$-glucose cotransporter inhibitor or an antidiabetic agent.

[12] A method for treating diabetes comprising administering an effective amount of the C-glycoside derivatives and the salts thereof according to any one of the above [1] to [7] to a patient.

BEST MODE FOR CARRYING OUT THE INVENTION

The best mode for carrying out the present invention will hereinbelow be described in detail.

Examples of "a five or six-membered monocyclic heteroaryl ring having 1 to 4 hetero atom(s) selected from N, S, and O" include pyridine, pyrimidine, pyrazine, thiophene, pyrrole, furan, thiazole, oxazole, imidazole, triazole, and tetrazole. Of these, pyridine, thiophene, furan, and tetrazole are preferable.

Examples of "a saturated or an unsaturated eight to ten-membered bicyclic hetero ring having 1 to 4 hetero atom(s) selected from N, S, and O" include benzofuran, benzothiophene, indole, benzoxazole, benzothiazole, benzimidazole, quinoline, isoquinoline, quinazoline, quinoxaline, and tetrahydroisoquinoline. Of these, benzofuran, benzothiophene, benzoxazole, and benzothiazole are preferable.

Examples of "a saturated or an unsaturated five or six-membered monocyclic hetero ring having 1 to 4 hetero atom(s) selected from N, S, and O" include pyridine, pyrimidine, pyrazine, thiophene, pyrrole, furan, thiazole, oxazole, imidazole, triazole, tetrazole, morpholine, piperidine, pyrrolidine, and piperazine. Of these, pyridine, thiophene, furan, tetrazole, morpholine, piperidine, and pyrrolidine are preferable.

Examples of "a saturated or an unsaturated eight to ten-membered bicyclic hydrocarbon ring" include indane, indene, and tetrahydronaphthalene. Of these, indene is preferable.

In the definition of the formulas in this specification, "lower" refers to a linear or branched carbon chain having 1-6 carbon atoms, unless otherwise specified. Accordingly, examples of "a lower alkyl" include linear or branched alkyls having 1-6 carbon atoms such as a methyl, ethyl, propyl, isopropyl, butyl, isobutyl, sec-butyl, tert-butyl, pentyl, isopentyl, hexyl, and isohexyl. Of these, alkyls having 1-3 carbon atoms are preferable, and a methyl and ethyl are particularly preferable.

As "a lower alkylene", in addition to a methylene, ethylene, propylene, and butylene, a branched lower alkylene may be used. Of these, a methylene and ethylene are preferable.

Examples of "a cycloalkyl" include three to eight-membered cycloalkyls. Of these, cyclopropyl, cyclobutyl, cyclopentyl, and cyclohexyl are preferable.

Examples of "a halogen atom" include fluorine atom, chlorine atom, bromine atom, or iodine atom. Of these, fluorine atom, chlorine atom, and bromine atom are preferable.

Examples of "a halogen-substituted lower alkyl" and "a halogen-substituted lower alkylene" include a lower alkyl substituted with the above halogen atom and a lower alkylene substituted with the above halogen atom, respectively. Of these, a lower alkyl and a lower alkylene substituted with one or more fluorine atoms are particularly preferable.

"An aryl" refers to a monocyclic to tricyclic aromatic hydrocarbon group having 6-14 carbon atoms. Examples of the aryl include phenyl, naphthyl, anthranyl, and phenanthryl. Of these, phenyl and naphthyl are preferable.

Examples of "a lower alkylene-aryl" include benzyl and phenethyl.

Examples of "an acyl" include formyl, acetyl, propionyl, butyryl, valeryl, and pivaloyl. Of these, acetyl is preferable.

In $R^5$ to $R^{11}$, "=O" means an oxo group. However, when A ring or B ring is, for example, a pyridine ring, "=O" sometimes means an oxopyridine ring, which is an N-oxide of a pyridine ring.

In addition, the compounds of the present invention includes a mixture or isolated product of various stereoisomers such as a tautomer and an optical isomer.

The compounds of the present invention may form an acid-addition salt or, depending on the type of substituent, a salt with a base. Specific examples of such a salt include an acid-addition salt with a mineral acid such as hydrochloric acid, hydrobromic acid, hydroiodic acid, sulfuric acid, nitric acid, and phosphoric acid; with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; or with an acidic amino acid such as aspartic acid and glutamic acid; a salt with an inorganic base such as sodium, potassium, magnesium, calcium, and aluminum; with an organic base such as methylamine, ethylamine, and ethanolamine; or with a basic amino acid such as lysine and ornithine; and ammonium salts.

The compounds of the present invention further include hydrates and various pharmaceutically acceptable solvates and polymorphs.

Incidentally, as a matter of course, the compounds of the present invention should not be limited to the compounds later described in Examples, but include all the compounds of the above formula (I) (C-glycoside derivatives) and the pharmaceutically acceptable salts thereof.

Moreover, the compounds of the present invention include what is called a prodrug, which are compounds being convertible to compounds of the above formula (I) or salts thereof as a result of the metabolism in the body. As a group for forming a prodrug of a compound of the present invention, a group described in Prog. Med. 5: 2157-2161 (1985) or a group described in "Development of Pharmaceuticals," vol. 7, Molecular Design, 163-198 (Hirokawa Shoten, 1990) can be given.

The compounds of the present invention (compounds shown by the above formula (I) or pharmaceutically acceptable salts thereof) can be produced by various known synthetic methods utilizing characteristics based on the type of its basic structure or substituent. In this case, from the viewpoint of production technique, it may be effective to substitute the functional group with a suitable protective group, that is, a group which can readily be converted to the functional group, at the stage of a starting material or intermediate, depending on the type of functional group. Following this, the protective group is optionally removed to obtain the target compound. Examples of such a functional group include a hydroxyl group and a carboxyl group, and examples of a protective group for these functional groups include protective groups described in Greene and Wuts, "Protective Groups in Organic Synthesis," Third Edition. These groups may be suitably used according to the reaction conditions.

PREPARATION EXAMPLES

Examples of typical production processes of a compound of the present invention will be hereinbelow described:

(Preparation Process 1)

In Preparation Process 1 are carried out an addition reaction with a halide (1) and an aldehyde derivative (2), followed by reduction, an addition reaction with a lactone derivative (4), followed by reduction to obtain a compound (I), and deprotecting the compound (I) to obtain a compound (I'), as shown in the following formula.

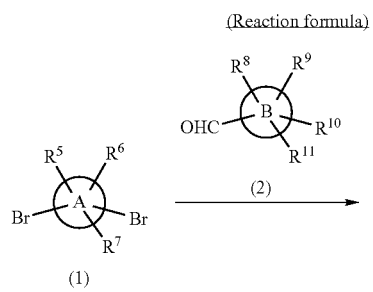

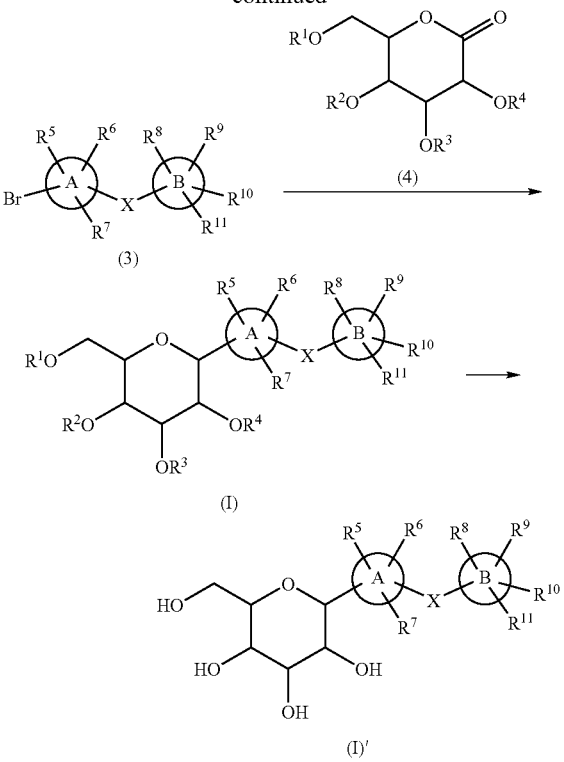

wherein A ring, B ring, X, and $R^1$ to $R^{11}$ in the formula mean the same things as the ones mentioned above.

The addition reaction with a halide (1) and an aldehyde derivative (2) is carried out in the presence of an alkyl lithium reagent such as n-butyl lithium, sec-butyl lithium, or t-butyl lithium in a suitable solvent. Specific examples of the solvent include ethers such as diethyl ether, tetrahydrofuran, and diglyme, and the solvent is appropriately selected according to the type of reaction substrate or the reaction conditions. The reaction temperature is generally from about −100° C. to about 180° C., and preferably from about −80° C. to about 30° C. though it varies, depending upon the type of starting material compounds, the reaction conditions, or the like.

The subsequent reduction reaction is carried out in the presence of an appropriate reducing agent and acid catalyst in a suitable solvent. Specific examples of the reducing agent include triethylsilane, triisopropylsilane, and t-butyldimethylsilane. Specific examples of the acid catalyst include boron trifluoride-diethyl ether complex, trifluoroacetic acid, and trimethylsilyl trifluoromethanesulfonate. Specific examples of the solvent include haloalkyls such as chloroform, dichloromethane, and 1,2-dichloroethane; ethers such as diethyl ether, tetrahydrofuran, and diglyme; acetonitrile; and a mixture of these solvents; and the solvent is appropriately selected according to the type of reaction substrate or the reaction conditions. The reaction temperature is generally from about −100° C. to about 180° C., and preferably from about −40° C. to about 20° C. though it varies, depending upon the type of starting material compounds, the reaction conditions, or the like.

The subsequent addition reaction of a lactone derivative (4) is carried out in the presence of an alkyl lithium reagent such as n-butyl lithium, sec-butyl lithium, or t-butyl lithium in a suitable solvent. Specific examples of the solvent include ethers such as diethyl ether, tetrahydrofuran, and diglyme, and the solvent is appropriately selected according to the type of reaction substrate or the reaction conditions. The reaction temperature is generally from about −100° C. to about 180° C., and preferably from about −80° C. to about 30° C. though it varies, depending upon the type of starting material compounds, the reaction conditions, or the like.

The subsequent reduction reaction is carried out in the same manner as the above reduction reaction.

The deprotection is carried out in the presence of a metal catalyst such as palladium/carbon, palladium hydroxide, or platinum/carbon in a suitable solvent in a hydrogen atmosphere, or in the presence of a Lewis acid in a suitable solvent. Specific examples of the Lewis acid include boron trichloride, boron tribromide, and aluminum trichloride. Specific examples of the solvent include ethers such as tetrahydrofuran and dioxane; esters such as ethyl acetate; alcohols such as methanol and ethanol; acetonitrile; and a mixture of these solvents, and the solvent is appropriately selected according to the type of reaction substrate or the reaction conditions. The reaction temperature is from about −100° C. to about 180° C., and preferably from about −40° C. to about 20° C. though it varies, depending upon the type of starting material compounds, the reaction conditions, or the like.

(Preparation Process 2)

In Preparation Process 2 are carried out an addition reaction with an aldehyde derivative (5) and a halide (6), followed by reduction, an addition reaction with a lactone derivative (4), followed by reduction to obtain a compound (I), and deprotecting the compound (I) to prepare a compound (I'), as shown in the following formula.

(Reaction formula)

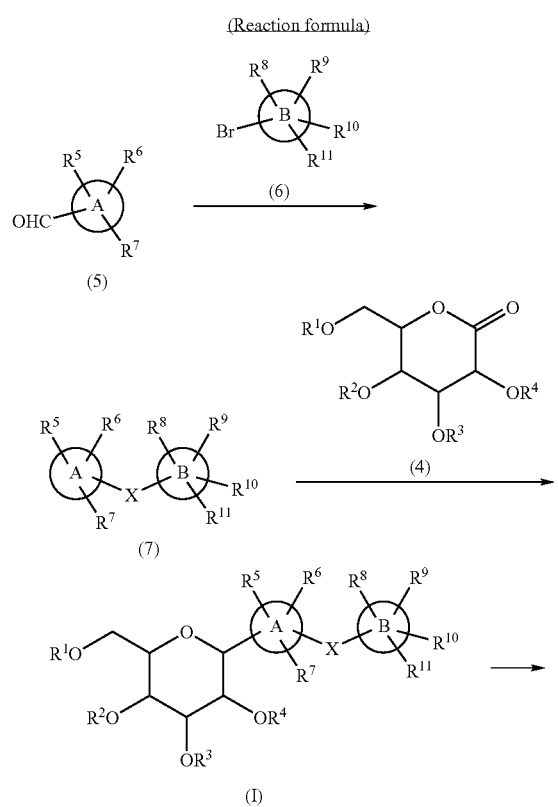

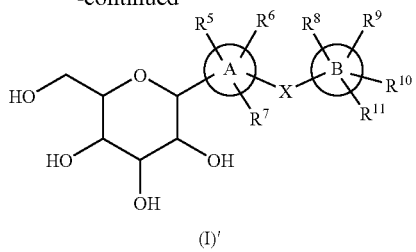

wherein A ring, B ring, X, and $R^1$ to $R^{11}$ in the formula mean the same things as the ones mentioned above.

The addition reaction with an aldehyde derivative (5) and a halide (6) is carried out in a manner similar to that of the addition reaction with a halide (1) and an aldehyde derivative (2).

The addition reaction may be carried alternatively by reacting the compound (6) with the compound (5) in an appropriate solvent, using a Grignard reagent prepared using a metal reagent such as magnesium. Specific examples of the solvent include ethers such as diethyl ether, tetrahydrofuran, and diglyme; and the solvent is appropriately selected according to the type of reaction substrate or the reaction conditions. The reaction temperature is generally from about 0° C. to about 180° C., and preferably from about 20° C. to about 80° C. though it varies, depending upon the type of starting material compounds, the reaction conditions, or the like.

The subsequent reduction reaction is carried out in the same manner as the reduction reaction in Preparation Process 1.

The subsequent addition reaction of a lactone derivative (4) is carried out in the same manner as the addition reaction of a lactone derivative (4) in Preparation Process 1.

The subsequent reduction reaction is carried out in the same manner as the reduction reaction in Preparation Process 1.

The deprotection is carried out in the same manner as the deprotection in Preparation Process 1.

(Preparation Process 3)

In Preparation Process 3 are carried out a substitution reaction in an appropriate solvent with a compound (8) and a compound (9), followed by alkylation by halide (11) to obtain a compound (I), and deprotecting the compound (I) to obtain a compound (I').

(Reaction Formula)

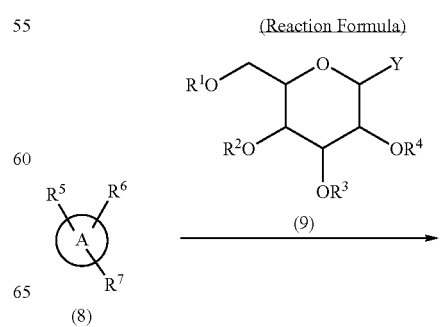

11
-continued

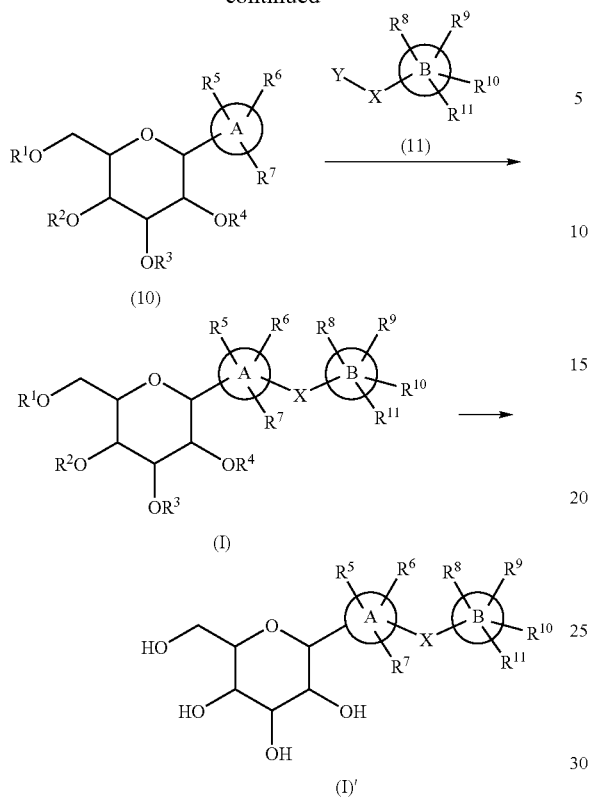

12
(Preparation Process 4)

In Preparation Process 4 are carried out protection of an alcohol (12), followed by an addition reaction with a lactone derivative (4), reduction, followed by deprotection to obtain a compound (13), which is then subjected to oxidation and an addition reaction with a compound (15), followed by reduction to obtain a compound (I), and deprotecting the compound (I) to prepare a compound (I').

(Reaction formula)

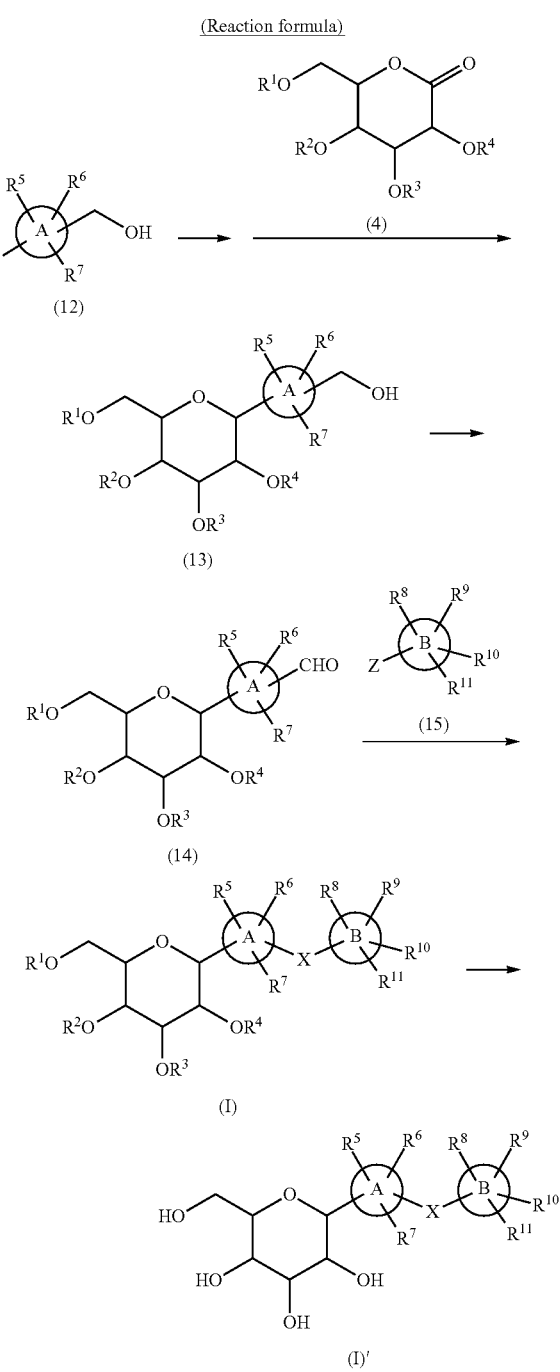

wherein A ring, B ring, X, and $R^1$ to $R^{11}$ in the formula mean the same things as the ones mentioned above, and Y is a group to be eliminated. Examples of the group to be eliminated are halide, acetoxy, trifluoroacetoxy, and trifluoromethanesulfoxy.

The substitution reaction is carried out in an appropriate solvent in the presence of an appropriate Grignard reagent. Specific examples of the Grignard reagent include methylmagnesium chloride, ethylmagnesium bromide, and isopropylmagnesium chloride. Specific examples of the solvent include ethers such as diethyl ether, tetrahydrofuran, and diglyme; benzene; and a mixture of these solvents; and the solvent is appropriately selected according to the type of reaction substrate or the reaction conditions. The reaction temperature is generally from about 0° C. to about 180° C., and preferably from about 20° C. to about 80° C. though it varies, depending upon the type of starting material compounds, the reaction conditions, or the like.

The alkylation is carried out in the presence of an appropriate base. Specific examples of the base include potassium hydroxide; sodium hydroxide; and Grignard reagents include ethers such as methylmagnesium chloride, ethylmagnesium bromide, and isopropylmagnesium chloride. Specific examples of the solvent include ethers such as diethyl ether, tetrahydrofuran, and diglyme; benzene; and a mixture of these solvents; and the solvent is appropriately selected according to the type of reaction substrate or the reaction conditions. The reaction temperature is generally from about 0° C. to about 180° C., and preferably from about 20° C. to about 80° C. though it varies, depending upon the type of starting material compounds, the reaction conditions, or the like.

The deprotection is carried out in the same manner as the deprotection in Preparation Process 1.

wherein A ring, B ring, X, and $R^1$ to $R^{11}$ in the formula mean the same things as the ones mentioned above, and Y and Z are halogen or hydrogen.

The alcohol (12) is protected according to a general manner with, for example, an appropriate protecting group such as tert-butyldimethylsilyl group, tert-butyldiphenylsilil group, and tetrahydropyranyl group. Then, the addition reaction with a lactone derivative (4) is carried out in an appropriate solvent in the present of an alkyllithium reagent such as n-butyllithium, sec-butyllithium, and tert-butyllithium. Specific examples of the solvent include ethers such as diethyl ether, tetrahydrofuran, and diglyme; and the solvent is appropriately selected according to the type of reaction substrate or the reaction conditions. The reaction temperature is generally from about −100° C. to about 180° C., and preferably from about −80° C. to about 30° C. though it varies, depending upon the type of starting material compounds, the reaction conditions, or the like.

The subsequent reduction reaction is carried out in the same manner as the reduction reaction shown in Preparation Process 1.

The subsequent deprotection is carried out in an appropriate solvent in the presence of an appropriate catalyst. Examples of the catalyst include tetrabutylammoniumfluoride, boron trifluoride ethylether complex, hydrogen fluoride, acetic acid, and p-toluenesulfonic acid. Examples of the solvent include ethers such as tetrahydrofuran and dioxane; alcohols such as methanol and ethanol; water; and a mixture of these solvents; and the solvent is appropriately selected according to the type of reaction substrate or the reaction conditions. The reaction temperature is generally from about −100° C. to about 180° C., and preferably from about 20° C. to about 80° C. though it varies, depending upon the type of starting material compounds, the reaction conditions, or the like.

The subsequent oxidation is carried out in a solvent in the presence of an appropriate oxidizing agent. Specific examples of the oxidizing agent include manganese dioxide, hydrogen peroxide, and pyridinium chlorochromate. Specific examples of the solvent include ethers such as tetrahydrofuran and dioxane; haloalkyls such as chloroform, dichloromethane, and 1,2-dichloroethane; and a mixture of these solvents; and the solvent is appropriately selected according to the type of reaction substrate or the reaction conditions. The reaction temperature is generally from about −100° C. to about 180° C., and preferably from about 20° C. to about 80° C. though it varies, depending upon the type of starting material compounds, the reaction conditions, or the like.

The subsequent addition reaction is carried out in the same manner as the addition reaction of a halide (1) and an aldehyde derivative (2) shown in Preparation Process (1).

The subsequent reduction reaction is carried out in the same manner as the reduction reaction shown in Preparation Process 1.

The deprotection is carried out in the same manner as the deprotection in Preparation Process 1.

(Preparation Process 5)

In Preparation Process 5, a compound (16) alone or a compound (16) and a metal are reacted to prepare a metal reagent, which is reacted with a compound (17) in the present of a palladium catalyst and, as necessary, an appropriate phosphine to obtain a compound (I), and the compound (I) is deprotected to obtain a compound (I').

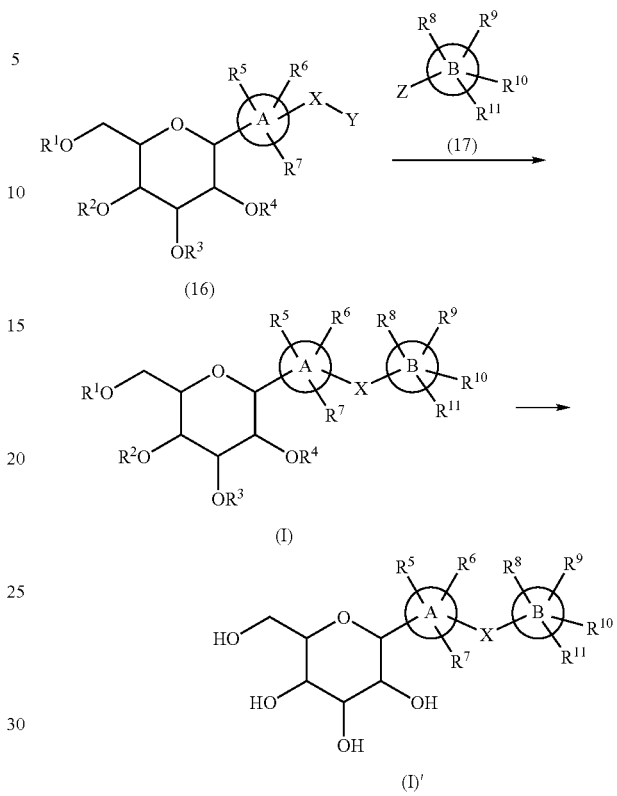

(Reaction Formula)

wherein A ring, B ring, X, and $R^1$ to $R^{11}$ in the formula mean the same things as the ones mentioned above, and Y is a group to be eliminated. Examples of the group to be eliminated are halogen, acetoxy, trifluoroacetoxy, and trifluoromethanesulfoxy. Z represents a hydrogen atom, MeS—, $R^a{}_3Sn—$, and $(R^aO)_2B—$. $R^a$ represents a lower alkyl.

Specific examples of the metal used in the reaction of the compound (16) and the compound (17) include copper, zinc, iron, and magnesium. Specific examples of the palladium catalyst include tetrakistriphenylphosphine palladium (0), palladium acetate (II), bistriphenylphosphine palladium dichloride (II), and trisdibenzyliden acetone dipalladium (0). Specific examples of the phosphine include triphenylphosphine, trifurylphosphine, diphenylphosphino ferrocene, diphenylphosphino ethane, dicyclohexylphosphino biphenyl, and tritert-butylphosphine. Specific examples of the solvent include ethers such as diethyl ether, tetrahydrofuran, and diglyme; and the solvent is appropriately selected according to the type of reaction substrate or the reaction conditions. The reaction temperature is generally from about 20° C. to about 180° C., and preferably from about 40° C. to about 100° C. though it varies, depending upon the type of starting material compounds, the reaction conditions, or the like.

The deprotection is carried out in the same manner as the deprotection in Preparation Process 1.

(Preparation Process 6)

In Preparation Process 6, a nitrile compound is subjected to a cyclization reaction to obtain an alkylated compound (I), followed by deprotection to obtain a compound (I)'.

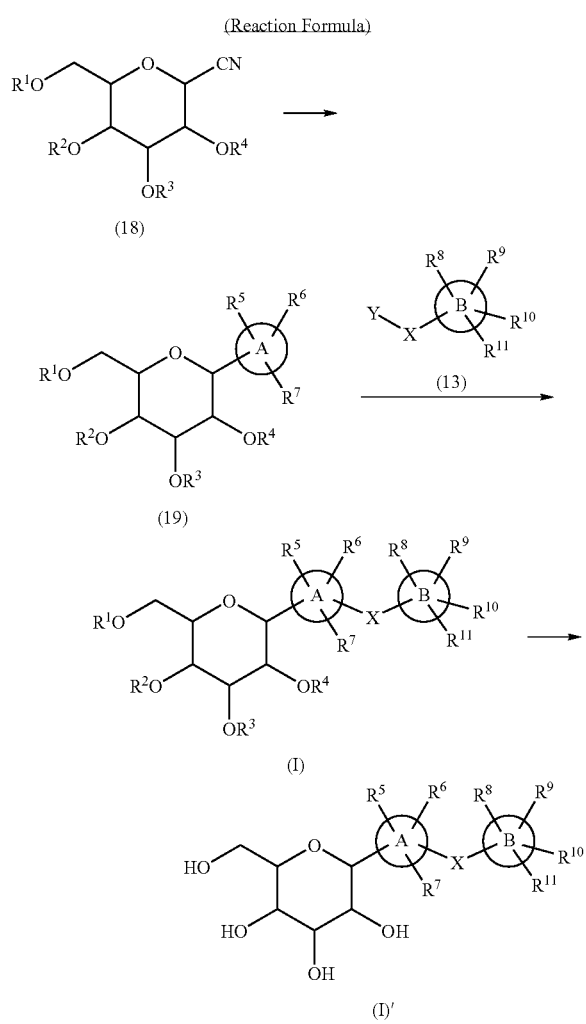

(Reaction Formula)

wherein A ring, B ring, X, and $R^1$ to $R^{11}$ in the formula mean the same things as the ones mentioned above, and Y is a group to be eliminated. Examples of the group to be eliminated are halogen, acetoxy, trifluoroacetoxy, and trifluoromethanesulfoxy.

The cyclization reaction is carried out in an appropriate solvent in the presence of an appropriate azide derivative and a hydrochloride of an amine. Specific examples of the azide derivative include sodium azide and trimethylsilyl azide. Specific examples of the amine include triethyl amine, triisopropyl amine, and diisopropylethyl amine. Specific examples of the solvent include dimethylformamide; dimethylsulfoxide; N-methylpyrrolidone; 1,3-Dimethyl-2-imidazolidinone; and a mixture of these solvents; and the solvent is appropriately selected according to the type of reaction substrate or the reaction conditions. The reaction temperature is generally from about −100° C. to about 180° C., and preferably from about 20° C. to about 80° C. though it varies, depending upon the type of starting material compounds, the reaction conditions, or the like.

The alkylation is carried out in an appropriate solvent in the presence of a halide (13) and an appropriate amine. Specific examples of the amine include triethyl amine, diisopropylethyl amine, and pyridine. Examples of the solvent include ethers such as tetrahydrofuran and dioxane; dimethyl formaldehyde; acetonitrile; and a mixture of these solvents; and the solvent is appropriately selected according to the type of reaction substrate or the reaction conditions. The reaction temperature is generally from about −100° C. to about 180° C., and preferably from about 20° C. to about 80° C. though it varies, depending upon the type of starting material compounds, the reaction conditions, or the like.

The deprotection is carried out in the presence of an appropriate base. Specific examples of the base include sodium hydroxide; potassium hydroxide; sodium carbonate; potassium carbonate; sodium methoxide; and sodium ethoxide. Specific examples of the solvent include alcohols such as methanol and ethanol; water; and a mixture of these solvents, and the solvent is appropriately selected according to the type of reaction substrate or the reaction conditions. The reaction temperature is from about −100° C. to about 180° C., and preferably from about 20° C. to about 80° C. though it varies, depending upon the type of starting materials, the reaction conditions, or the like.

EXAMPLES

The compound of the present invention will now be described in more detail by way of examples. Since starting materials of the compounds of the present invention include novel compounds, the methods for preparing these compounds will also be described in Reference Examples.

Reference Example 1

Potassium carbonatede (2.08 g) was added to a solution of 5-bromo-2,4-dihydroxybenzaldehyde (1.09 g) in acetone (20 ml), and the mixture was stirred for 30 minutes at room temperature. Then, chloromethyl methyl ether (1.01 g) was added to the reaction mixture, and the mixture was stirred over night at room temperature. To the reaction mixture were added water and toluene, and the toluene layer was separated, and then washed with saturated sodium bicarbonate solution and saturated saline solution, followed by drying and filtration, and the solvent was evaporated from the filtrate under reduced pressure to give the residue to obtain a solid. The solid was washed with diisopropylether and dried to obtain 5-bromo-2,4-bis (methoxymethoxy)benzaldehyde (0.91 g).

Reference Example 2

N-Bromosuccinimide (7.35 g) and benzoyl peroxide (196 mg) were added to a solution of 4-bromo-2-methylbiphenyl (5.0 g) in carbon tetrachloride (150 ml), and the mixture was stirred over night under reflux condition. After cooling to room temperature, the reaction mixture was poured into water and extracted with chloroform. The organic layer was washed with saturated saline solution and dried over anhydrous magnesium sulfate. After filtration, the solvent was evaporated therefrom under reduced pressure to give the residue. The residue was purified by silica gel column chromatography (n-hexane-ethyl acetate) to obtain 4-bromo-2-(dibromomethyl)biphenyl (7.9 g). Sodium acetate (9.6 g) was added to a solution of 4-bromo-2-(dibromomethyl)biphenyl in acetic acid (240 ml) and stirred for two days under reflux condition. After cooling to room temperature, 4M hydrochloric acid (50 ml) was added to the reaction mixture, and the resulting mixture was stirred for two hours under reflux condition. After cooling to room temperature, the solvent was evaporated therefrom under reduced pressure to give the residue, ethyl acetate was added to the resulting residue, and the resultant was washed with 1M hydrochloric acid and saturated saline solution in order and dried over anhydrous magnesium sulfate. After filtration, the solvent was evaporated from the filtrate under reduced pressure to give the residue, and the resulting residue was dried to obtain 4-bromo biphenyl-3-carboaldehyde (5.05 g).

Reference Example 3

Imidazole (3.3 g) and tert-butyl-diphenylchlorosilane (10.0 g) were added to a solution of (3-bromo-5-fluorophenyl)methanol (5.0 g) in dimethylformamide (50 ml), and the mixture was stirred over night at room temperature. The reaction mixture was poured into water and extracted with ethyl acetate. The organic layer was washed with saturated saline solution and dried over anhydrous magnesium sulfate. After filtration, the solvent was evaporated from the filtrate under reduced pressure to give the residue. The resulting residue was purified by silica gel column chromatography (n-hexane-ethyl acetate) to obtain [(3-bromo-5-fluorobenzyl)oxy] (tert-butyl)diphenylsilane (9.5 g).

The compounds in Reference Examples 4, 5, 6 were obtained in a manner similar to that of Reference Example 3.

Reference Example 7

Ten percents of palladium/carbon (500 mg) was added to a solution of (1S)-1,5-anhydro-2,3,4,6-tetra-O-benzyl-1-(3-([[tert-butyl (diphenyl)silyl]oxy]methyl)phenyl)-D-glucitol (5.93 g) in tetrahydrofuran (45 ml), and the mixture was stirred for 20 hours at room temperature in a hydrogen atmosphere. After filtration through celite of the reaction mixture, the solvent was evaporated from the filtrate under reduced pressure to give the residue, and the residue (3.47 g) was dissolved in pyridine (40 ml). To the resulting solution were added acetic anhydride (2.68 ml) and 4-dimethylaminopyridine (catalyst amount), and the resulting mixture was stirred for 16 hours at room temperature. Then, methanol (50 ml) was added dropwise to the reaction mixture, the solvent was evaporated therefrom under reduced pressure to give the residue, and the resulting residue was subjected to co-evaporation with toluene. The resulting residue was dissolved in ethyl acetate-toluene (3:2), washed, and then dried over magnesium sulfate. Then, the solvent was evaporated therefrom under reduced pressure to give the residue, and the residue (4.48 g) was dissolved in tetrahydrofuran (100 ml), and 1M tetrahydrofuran solution (8.12 ml) of tetrabutylammoniumfluoride was dropped, and the solution was stirred for two hours at room temperature. Then, the reaction mixture was concentrated and purified by silica gel column chromatography to obtain (1S)-2,3,4,6-tetra-0-acetyl-1,5-anhydro-1-[3-(hydroxymethyl)phenyl]-D-glucitol (1.30 g).

Reference Example 8

Triphenylphosphine (926 m) and carbon tetrabromide (1.17 g) were added to a solution of (1S)-2,3,4,6-tetra-0-acetyl-1,5-anhydro-1-[3-(hydroxymethyl)phenyl]-D-glucitol (1.29 g) in dichloromethane (40 ml) under cooling with ice, and the mixture was stirred for 20 minutes at room temperature. Saturated aqueous solution of sodium bicarbonate (60 ml) was added to the reaction mixture to separate the organic layer. Then, the mixture was dried over magnesium sulfate, and the solvent was evaporated therefrom under reduced pressure to give the residue. The residue was purified by silica gel column chromatography to obtain (1S)-2,3,4,6-tetra-0-acetyl-1,5-anhydro-1-[3-(bromomethyl)phenyl]-D-glucitol (1.04 g).

Reference Example 9

1.56 Moles of n-hexane solution of n-butyllithium (50 ml) were added dropwise to a solution of 1-(benzyloxy)-2-bromo-4-methylbenzene (20 g) in tetrahydrofuran (250 ml) at −78° C. in an argon atmosphere, and the mixture was stirred for one hour at the same temperature. To the reaction mixture was added dropwise a solution of 2,3,4,6-tetra-0-benzyl-D-(+)-glucono-1,5-lactone (35.0 g) in tetrahydrofuran (200 ml) at −78° C., and the resulting mixture was stirred for one hour at the same temperature. Aqueous solution of 1M hydrochloric acid (10 ml) was added to the mixture, and the temperature was raised to room temperature. Then, anhydrous magnesium sulfate (50 g) was added to the mixture, and the mixture was stirred for one hour at room temperature. After filtration, the filtrate was concentrated, and the resulting residue was purified by silica gel column chromatography (n-hexane-ethyl acetate) to obtain 2,3,4,6-tetra-0-benzy-1-C-[2-(benzyloxy)-5-methylphenyl]-D-glucopyranose (37 g). Triisopropylsilane (31 ml) and borontrifluoride diethylether complex (12.6 ml) were added to a solution of 2,3,4,6-tetra-0-benzy-1-C-[2-(benzyloxy)-5-methylphenyl]-D-glucopyranose in dicyclomethane-acetonitrile (1:3) (400 ml) under cooling with ice in an argon atmosphere, and the mixture was stirred for one hour at the same temperature. The reaction mixture was poured into saturated aqueous solution of sodium bicarbonate and extracted with chloroform. The organic layer was dried over anhydrous magnesium sulfate and filtrated, and then the solvent was evaporated from the filtrate under reduced pressure to give the residue. The residue was purified by silica gel column chromatography (n-hexane-ethyl acetate) to obtain (1S)-1,5-anhydro-2,3,4,6-tetra-O-benzyl-1-[2-(benzyloxy)-5-methylphenyl]-D-glucitol (16.9 g).

Reference Example 10

1.56 Moles of n-hexane solution of n-butyllithium (14.5 ml) were added dropwise to a solution of [(3-bromo-5-fluorobenzyl)oxy] (tert-butyl)diphenylsilane (10 g) in tetrahydrofuran (100 ml) at −78° C. in an argon atmosphere, and the mixture was stirred for half an hour at the same temperature. To the reaction mixture was added dropwise a solution of 2,3,4,6-tetra-0-benzyl-D-(+)-glucono-1,5-lactone (12.2 g) in tetrahydrofuran (100 ml) at −78° C., and the mixture was stirred for two hours at the same temperature. Aqueous solution of 1M hydrochloric acid (10 ml) was added to the mixture, and the temperature was raised to room temperature. Then, anhydrous magnesium sulfate (50 g) was added to the mixture, and the mixture was stirred for one hour at room temperature. After filtration, the filtrate was concentrated, and the residue was purified by silica gel column chromatography (n-hexane-ethyl acetate) to obtain 2,3,4,6-tetra-0-benzy-1-C-[3-({[tert-butyl(diphenyl)silyl]oxy}methyl)-5-fluorophenyl]-D-glucopyranose (6 g). Triethylsilane (1.3 ml) and borontrifluoride diethylether complex (0.9 ml) were added to a solution of 2,3,4,6-tetra-0-benzy-1-C-[3-({[tert-butyl (diphenyl)silyl]oxy}methyl)-5-fluorophenyl]-D-glucopyranose in dicyclomethane-acetonitrile (1:1) (120 ml) under cooling with ice in an argon atmosphere, and the mixture was stirred for one hour at the same temperature. The reaction mixture was poured into saturated aqueous solution of sodium bicarbonate and extracted with chloroform. The organic layer was dried over anhydrous magnesium sulfate and filtrated, and then the solvent was evaporated from the filtrate under reduced pressure to give the residue. The residue was purified by silica gel column chromatography (n-hexane-ethyl acetate) to obtain (1S)-1,5-anhydro-2,3,4,6-tetra-0- benzyl-1-[3-({[tert-butyl (diphenyl)silyl]oxy}methyl)-5-fluorophenyl]-D-glucitol (4.2 g). 1 M tetrahydrofuran solution of tetrabutylammoniumfluoride (9.5 ml) was added dropwise to a solution of (1S)-1,5-anhydro-2,3,4,6-tetra-0-benzyl-1-[3-({[tert-butyl(diphenyl)silyl]oxy}methyl)-5-fluorophenyl]-D-glucitol in tetrahydrofuran (90 ml), and the mixture was stirred for one hour at room temperature. The reaction mixture was concentrated, and the resulting residue was purified by silica gel column chromatography (n-hexane-ethyl acetate) to obtain (1S)-1,5-anhydro-2,3,4,6-tetra-0-benzyl-1-[3-fluoro-5-(hydroxymethyl)phenyl]-D-glucitol (0.5 g).

The compounds in Reference Examples 11, 12, 13 were obtained in a manner similar to that of Reference Example 10.

Reference Example 14

Methanol (75 ml), Pd(OH)$_2$ (168 mg) was added to a solution of (1S)-1,5-anhydro-2,3,4,6-tetra-0-benzyl-1-[2-(benzyloxy)-5-methylphenyl]-D-glucitol (16.8 g) in ethyl acetate (150 ml), and the mixture was stirred over night in a hydrogen atmosphere. After filtration through celite, the filtrate was concentrated. The obtained solid was recrystallized from ethyl acetate. Acetic anhydride (15 ml) was added to a solution of the obtained white crystals (6.6 g) in pyridine (30 ml) and the mixture was stirred over night at room temperature. Methanol was added to the reaction mixture, the solvent was evaporated therefrom under reduced pressure to give the residue, and the resulting residue was subjected to co-evaporation with toluene. The obtained solid was recrystallized from ethanol to obtain (1S)-1-[2-(acetoxy)-5-methylphenyl]-2,3,4,6-tetra-0-acetyl-1,5-anhydro-D-glucitol (9.1 g).

Reference Example 15

N-bromosuccinimide and (α, α'-azoisobutylo)nitrile was added to (1S)-1-[2-(acetoxy)-5-methylphenyl]-2,3,4,6-tetra-0-acetyl-1,5-anhydro-D-glucitol (9.1 g) in carbon tetrachloride (180 ml), and the mixture was stirred for two hours under reflux condition. After cooling to room temperature, the reaction mixture was poured into water and extracted with chloroform. The organic layer was washed with water and saturated saline solution and dried over anhydrous magnesium sulfate. After filtration, the solvent was evaporated from the filtrate under reduced pressure to give the residue. The resulting residue was purified by silica gel column chromatography (n-hexane-ethyl acetate) to obtain (1S)-1-[2-(acetoxy)-5-(bromomethyl)phenyl]-2,3,4,6-tetra-0-acetyl-1,5-anhydro-D-glucitol (7.8 g).

The compound in Reference Example 16 was obtained in a manner similar to that of Reference Example 9.

Reference Example 17

3-(2,3,4,6-Tetra-0-benzyl-β-D-glucopyranosyl)-4-fluorobenzonitrile (1.20 g) was dissolved in morpholine (10 ml), and the mixture was stirred for 24 hours at 110° C. The mixture was cooled to room temperature, and the solvent was evaporated from the filtrate under reduced pressure to give the residue. The residue was purified by silica gel column chromatography (n-hexane-ethyl acetate) to obtain 3-(2,3,4,6-tetra-0-benzyl-β-D-glucopyranosyl)-4-morpholinobenzonitrile (0.93 g).

Reference Example 18

A solution of 1.01 M toluene (2.1 ml) of diisobutyl aluminum hydride was added dropwise to a solution of 3-(2,3,4,6-tetra-0-benzyl-β-D-glucopyranosyl)-4-morpholino benzonitrile (700 mg) in toluene (10 ml) cooled at −78° C. under an argon atmosphere, and the mixture was stirred for 1.5 hours. Aqueous solution of saturated ammonium chloride was added to the mixture, and extracted with chloroform. The organic layer was washed with saturated saline solution and dried over anhydrous sodium sulfate. After filtration, the solvent was evaporated from the filtrate under reduced pressure to give the residue. The residue was purified by silica gel column chromatography (n-hexane-ethyl acetate) to obtain 3-(2,3,4,6-tetra-0-benzyl-β-D-glucopyranosyl)-4-morpholinobenzaldehyde (517 g).

Reference Example 19

Manganese dioxide (740 mg) was added to a solution of (1S)-1,5-anhydro-2,3,4,6-tetra-0-benzyl-1-[3-fluoro-5-(hydroxyl methyl)phenyl]-D-glucitol (0.5 g) in chloroform (10 ml), and the mixture was stirred for 24 hours. After filtration through celite, washing with chloroform was carried out, and the filtrate was concentrated. The resulting residue was dried to obtain 3-(-2,3,4,6-tetra-0-benzyl-β-D-glucopyranosyl)-5-fluoro benzaldehyde (0.4 g).

The compounds in Reference Examples 20 to 22 were obtained in a manner similar to that of Reference Example 19.

Reference Example 23

1.6 Moles of n-hexane solution of n-butyllithium (4.6 ml) were added dropwise to a solution of 1-bromo-3-(dimethoxymethyl)benzene (1.7 g) in tetrahydrofuran (20 ml) at −78° C., and the mixture was stirred for half an hour. To the reaction mixture was added dropwise a solution of 2,3,4,6-tetra-0-benzyl-D-(+)-glucono-1,5-lactone (4.0 g) in tetrahydrofuran (20 ml), and the mixture was stirred for one hour. Aqueous solution of saturated ammonium chloride was added to the mixture, and extracted with ethyl acetate. The organic layer was washed with saturated saline solution and dried over anhydrous sodium sulfate. After filtration, the solvent was evaporated from the filtrate under reduced pressure to give the residue. The resulting residue was purified by silica gel column chromatography (n-hexane-ethyl acetate) to obtain 2,3,4,6-tetra-0-benzyl-1-C-[3-dimethoxymethyl]phenyl]-D-glucopyranose (1.83 g). To a solution of 2,3,4,6-tetra-0-benzyl-1-C-3-dimethoxymethyl]phenyl]-D-glucopyranose in acetone-water (2:1) (30 ml) were added sulfamic acid (0.51 g) and sodium chlorite (0.6 g), and the mixture was stirred for eight hours at room temperature. Ten percents of hydrochloric acid was added to the reaction mixture to adjust the pH to 2, and extracted with chloroform. The organic layer was washed with saturated saline solution and dried over anhydrous sodium sulfate. After filtration, the solvent was evaporated from the filtrate under reduced pressure to give the residue. The resulting residue was purified by silica gel column chromatography (n-hexane-ethyl acetate) to obtain 3-(2,3,4,6-tetra-0-benzyl-D-glucopyranose-1-C)-yl-benzoic acid (1.3 g). Triethylsilane (0.63 ml) and trifluoroacetic acid (0.15 ml) were added to a solution of 3-(2,3,4,6-tetra-0-benzyl-D-glucopyranose-1-C)-yl-benzoic acid in dichloromethane (15 ml), and the mixture was stirred for 15 hours at room temperature. Aqueous solution of 10% sodium hydroxide was added to the reaction mixture, and extracted with dichloromethane. The organic layer was washed with saturated saline solution and dried over anhydrous sodium sulfate. After filtration, the solvent was evaporated from the filtrate under reduced pressure to give the residue. The resulting residue was purified by silica gel column chromatography (n-hexane-ethyl acetate) to obtain 3-(2,3,4,6-tetra-0-benzyl-β-D-glucopyranosyl)benzoic acid (0.85 g). N,O-dimethylhydroxylamine hydrochloride (0.14 g), triethyl amine (0.2 ml), and 1-ethyl-3-(3-dimethylaminopropyl) carbodiimide (0.28 g) were added to a solution of 3-(2,3,4,6-tetra-0-benzyl-β-D-glucopyranosyl)benzoic acid in dichloromethane (10 ml), and the mixture was stirred for four hours at room temperature. Then, the reaction mixture was poured into ice-cooled water and extracted with ethyl acetate. The organic layer was washed with saturated saline solution and dried over anhydrous sodium sulfate. After filtration, the solvent was evaporated from the filtrate under reduced pressure to give the residue, and the resulting residue was purified by silica gel column chromatography (n-hexane-ethyl acetate) to obtain 3-(2,3,4,6-tetra-0-benzyl-β-D-glucopyranosyl)-N-methyl-N-methoxybenzamide (0.42 g).

The compound in Reference Example 24 was obtained in a manner similar to that of Example 47.

Reference Example 25

Diisopropyl amine (2.34 g) was dissolved in tetrahydrofuran (60 ml). 1.58 M n-hexane solution (13.3 ml) of n-butyllithium was added dropwise to the mixture at −78° C., and the mixture was stirred for half an hour at 0° C. Then, 2,6-dichloropyrazine (2.98 g) was added to the reaction mixture at −78° C., and the mixture was stirred for ten minutes. Then, a solution of 2,3,4,6-tetra-0-benzyl-D-(+)-glucono-1,5-lactone (10.8 g) in tetrahydrofuran (100 ml) was added to the mixture, and the mixture was stirred for three hours at −78° C. The reaction mixture was washed with saturated ammonium chloride, and the water layer was extracted with diethyl ether. The organic layer was dried over sodium sulfate, the solvent was evaporated therefrom under reduced pressure to give the residue, and the resulting residue was purified by silica gel column chromatography (n-hexane-ethyl acetate) to obtain 2,3,4,6-tetra-0-benzyl-1-C-(3,5-dichloropyrazine-2-yl)-D-glucopyranose (9.07 g). The obtained 2,3,4,6-tetra-0-benzyl-1-C-(3,5-dichloropyrazine-2-yl)-D-glucopyranose (7.93 g) was dissolved in dichloromethane (90 ml), and triethyl silane (36.8 ml) and trifluoloacetic acid (17.7 ml) were added to the mixture, and the mixture was stirred for 19 days at room temperature. The reaction mixture was washed with saturated sodium bicarbonate solution, and the water layer was extracted with chloroform. The organic layer was dried over sodium sulfate, the solvent was evaporated therefrom under reduced pressure to give the residue, and the resulting residue was purified by silica gel column chromatography (n-hexane-ethyl acetate) to obtain (1S)-1,5-anhydro-2,3,4,6-tetra-0-benzyl-1-(3,5-dichloropyrazine-2-yl)-D-glucitol (2.15 g).

Reference Example 26

1,3-Dibromobenzene (25 g) and a solution of a Grignard reagent prepared using metal magnesium in ether (50 ml) were added to a solution of 5-ethylthiophene-2-carboxyaldehyde (5.0 g) in tetrahydrofuran (50 ml) at 0° C., and the mixture was stirred for one hour. The reaction mixture was poured into ice-cooled water and extracted with ethyl acetate. The organic layer was washed with saturated saline solution and dried over anhydrous sodium sulfate. After filtration, the solvent was evaporated from the filtrate under reduced pressure to give the residue, and the resulting residue was purified by silica gel column chromatography (n-hexane-ethyl acetate) to obtain (3-bromophenyl) (5-ethyl-2-thienyl)methanol (5.57 g). Borontrifluoride diethyl ether complex (1.57 ml) and triethylsilane (3.83 ml) were added to a solution of (3-bromophenyl) (5-ethyl-2-thienyl)methanol in acetonitrile (20 ml) at −40° C., and the mixture was stirred for two hours. Aqueous solution of saturated potassium carbonate was added to the reaction mixture, and extracted with ethyl acetate. The organic layer was washed with saturated saline solution and dried over anhydrous sodium sulfate. After filtration, the solvent was evaporated from the filtrate under reduced pressure to give the residue, and the residue was purified by silica gel column chromatography (n-hexane-ethyl acetate) to obtain 2-(3-bromobenzyl)-5-methylthiophene (3.77 g).

The compounds in Reference Examples 27 and 28 were obtained in a manner similar to that of Reference Example 26.

Reference Example 29

A solution of 1.56 M hexane (23.7 ml) of n-butyl lithium was added dropwise to a solution of 3-methyl-1-benzothiophene (5.0 g) in tetrahydrofuran (50 ml) at −78° C. under an argon atmosphere, and the mixture was stirred for half an hour at the same temperature. Then, a solution of 3-bromobenzaldehyde (6.05 g) in tetrahydrofuran (6 ml) was added dropwise to the mixture, and the mixture was stirred for half an hour. Water was added to the reaction mixture, and extracted with ethyl acetate. The organic layer was washed with aqueous solution of saturated ammonium chloride and dried over anhydrous magnesium sulfate. After filtration, the solvent was evaporated from the filtrate under reduced pressure to give the residue, and the residue was purified by silica gel column chromatography (n-hexane-ethyl acetate) to obtain (3-bromophenyl)(3-methyl-1-benzothien-2-yl) methanol (10.0 g) as achromatic oily matter. Borontrifluoride diethyl ether complex (4.42 ml) and triethylsilane (9.58 ml) were added to a solution of (3-bromophenyl)(3-methyl-1-benzothien-2-yl)methanol in dichloromethane (100 ml) at −30° C., and the mixture was stirred for half an hours. After the reaction mixture was heated to −10° C. and stirred for 10 minutes, aqueous solution of saturated sodium carbonate was added to the reaction mixture, and extracted with ethyl acetate. The organic layer was washed with saturated saline solution and dried over anhydrous magnesium sulfate. After filtration, the solvent was evaporated from the filtrate under reduced pressure to give the residue, and the residue was purified by silica gel column chromatography (n-hexane-ethyl acetate) to obtain 2-(3-bromobenzyl)-3-methyl-1-benzothiophene (6.68 g).

The compounds in Reference Examples 30 to 36 were obtained in a manner similar to that of Reference Example 29.

Reference Example 37

Benzo[b]thiophene (1.12 g) was dissolved in tetrahydrofuran (50 ml). This solution was cooled to −78° C., and a solution of 1.58 M hexane (10.5 ml) of n-butyllithium was added dropwise to the solution, and the mixture was stirred for 15 minutes at −78° C. Then, 5-chloro-2-bromobenzaldehyde (3.15 g) dissolved in tetrahydrofuran (50 ml) was added dropwise to the reaction mixture, and the mixture was stirred for two hours at room temperature. Aqueous solution of saturated ammonium chloride was added to the reaction mixture, and then the solvent was evaporated from the filtrate under reduced pressure to give the residue. Ethyl acetate and water were added to the residue obtained, and extracted with ethyl acetate. The organic layer was dried over magnesium sulfate, the solvent was evaporated from the filtrate under reduced pressure to give the residue, and the residue was purified by silica gel column chromatography (n-hexane-ethyl acetate) to obtain 1-benzothien-2-yl(5-bromo-2-chlorophenyl) methanol (4.75 g). Imidazole (1.08 g) and tert-butyl dimethylchlorosilane (2.99 g) were added to a solution of 1-benzothien-2-yl(5-bromo-2-chlorophenyl)methanol in dimethylformamide (100 ml), and the mixture was stirred for three hours at 70° C. Water was added to the reaction mixture, and extracted with diethyl ether. The organic layer was dried over magnesium sulfate, the solvent was evaporated therefrom under reduced pressure to give the residue, and the resulting residue was purified by silica gel column chromatography (n-hexane-ethyl acetate) to obtain [1-benzothien-2-yl(5-bromo-2-chloro phenyl)methoxy](tert-butyl) dimethylsilane (3.34 g).

The compounds in Reference Examples 38, 39 and 40 were obtained in a manner similar to that of Reference Example 37.

Reference Example 41

Aluminum chloride (8.9 g) and 4-ethylbenzoylchloride (5.96 g) were added to a solution of 2-bromothiophene (3.2 ml) in dichloromethane (50 ml) at 0° C., and the mixture was stirred for four hours at room temperature. 10% hydrochloric acid was added to the reaction mixture, and extracted with ethyl acetate. The organic layer was washed with water and saturated saline solution in order and dried over anhydrous sodium sulfate. After filtration, the solvent was evaporated from the filtrate under reduced pressure to give the residue. The residue was purified by silica gel column chromatography (n-hexane-ethyl acetate) to obtain (5-bromo-2-thienyl)(4-ethylphenyl)methanone (8.97 g). Borontrifluoride diethyl ether complex (1.57 ml) and triethylsilane (3.83 ml) were added to a solution of (5-bromo-2-thienyl)(4-ethylphenyl)methanone in acetonitrile (20 ml) at −40° C., and the mixture was stirred for two hours. Aqueous solution of saturated potassium carbonate was added to the reaction mixture, and extracted with ethyl acetate. The organic layer was washed with saturated saline solution and dried over anhydrous sodium sulfate. After filtration, the solvent was evaporated from the filtrate under reduced pressure to give the residue, and the residue was purified by silica gel column chromatography (n-hexane-ethyl acetate) to obtain 2-bromo-(4-ethylbenzyl)thiophene (6.78 g).

Reference Example 42

A solution of 1M tetrahydrofuran (2.98 ml) of ethylmagnesium bromide was added dropwise to pyrrole (0.2 g), and the mixture was stirred for half an hour. The solvent was evaporated from the filtrate under reduced pressure to give the residue, and 4-ethylbenzyl bromide (663 mg) was added to a solution of the obtained residue in benzene (5.0 ml), and the mixture was stirred for five hours at 60° C. Aqueous solution of saturated ammonium chloride was added to the reaction mixture, and extracted with ethyl acetate. The organic layer was washed with saturated saline solution and dried over anhydrous sodium sulfate. After filtration, the solvent was evaporated from the filtrate under reduced pressure to give the residue, and the residue was purified by silica gel column chromatography (n-hexane-ethyl acetate) to obtain 2-(4-ethylbenzyl)-1H-pyrrole (0.12 g).

Reference Example 43

A solution of 1.5 M hexane (21 ml) of n-butyllithium was added dropwise to a solution of 6,7-dimethyl-benzofuran (4.1 g) in tetrahydrofuran (100 ml) at −78° C. under an argon atmosphere, and the mixture was stirred for half an hour. Then, chloro tri-n-butyltin (8.4 ml) was added to the mixture, and the mixture was stirred for one hour. Aqueous solution of saturated ammonium chloride was added to the reaction mixture, and extracted with ethyl acetate. The organic layer was washed with saturated saline solution and dried over anhydrous sodium sulfate. After filtration, the filtrate was concentrated, and the residue was purified by silica gel column chromatography (n-hexane) to obtain tri-n-butyl(6,7-dimethyl-benzofuran-2-yl) tin (10.8 g).

The compounds in Reference Examples 44 to 49 were obtained in a manner similar to that of Reference Example 43.

Reference Example 50

Sodium borohydride (1.3 g) was added to a solution of 6-methyl-indane-1-one (5.0 g) in methanol (50 ml) at 0° C., and the mixture was stirred for one hour. The reaction mixture was poured into ice-cooled water, and extracted with ethyl acetate. The organic layer was washed with saturated saline solution and dried over anhydrous sodium sulfate. After filtration, the filtrate was concentrated to obtain 6-methylindane-1-ol (5.5 g). To a solution of 6-methylindane-1-ol in toluene (50 ml) was added p-toluene sulfonic acid monohydrate (0.2 g), and the mixture was stirred for 20 minutes. The temperature of the reaction mixture was returned to room temperature, and the reaction mixture was washed with water, 5% sodium hydrogencarbonate aqueous solution, and saturated saline solution in order and dried over anhydrous sodium sulfate. After filtration, the filtrate was concentrated to obtain 5-methyl-1H-indene (5.5 g).

The compound in Reference Example 51 was obtained in a manner similar to that of Reference Example 50.

Reference Example 52

Water (0.6 ml) and N-bromosuccinimide (6.1 g) was added to a solution of 5-methyl-1H-indene (4.4 g) in dimethylsulfoxide (50 ml), and the mixture was stirred for 40 minutes at room temperature. The reaction mixture was poured into ice-cooled water, and extracted with ether. The organic layer was washed with water, 5% sodium hydrogencarbonate aqueous solution, and saturated saline solution in order and dried over anhydrous sodium sulfate. After filtration, the filtrate was concentrated, and the resulting crystals were washed with hexane to obtain, by filtration, 2-bromo-6-methylindane-1-ol (4.4 g). To a solution of 2-bromo-6-methylindane-1-ol in toluene (50 ml) was added p-toluene sulfonic acid monohydrate (0.1 g), and the mixture was stirred for 20 minutes. The temperature of the reaction mixture was returned to room temperature, and the reaction mixture was washed with water, 5% sodium hydrogencarbonate aqueous solution, and saturated saline solution in order and dried over anhydrous sodium sulfate. After filtration, the filtrate was concentrated, and the residue was purified by silica gel column chromatography (n-hexane-ethyl acetate) to obtain 2-bromo-5-methyl-1H-indene (1.7 g).

The compound in Reference Example 53 was obtained in a manner similar to that of Reference Example 52.

Reference Example 54

2-Bromo-1H-indene (3.0 g) and a solution of a Grignard reagent prepared using metal magnesium in tetrahydrofuran (20 ml) were added to a solution of 3-(2,3,4,6-tetra-0-benzyl-β-D-glucopyranosyl)-N-methyl-N-methoxybenzamide (6.99 g) in tetrahydrofuran (20 ml) at 0° C., and the mixture was stirred for two hours. The reaction mixture was poured into ice-cooled water and extracted with ethyl acetate. The organic layer was washed with saturated saline solution and dried over anhydrous sodium sulfate. After filtration, the solvent was evaporated from the filtrate under reduced pressure to give the residue, and the residue was purified by silica gel column chromatography (n-hexane-ethyl acetate) to obtain (1H-indene-2-yl)[3-(2,3,4,6-tetra-0-benzyl-β-D-glucopyranosyl)phenyl]methanone (0.84 g).

Reference Example 55

Pentamethylbenzene (3.62 g) was dissolved in a solution of methyl-4-(1-benzothien-2-ylmethyl)-2-(2,3,4,6-tetra-0-benzyl-β-D-glucopyranosyl)benzoate (1.31 g) in dichloromethane (150 ml), and 1 M n-heptane solution (6.83 ml) of boron trichloride was added dropwise to the mixture at −78° C., and the mixture was stirred for two hours at the same temperature. Then, methanol (40 ml) was added dropwise to the reaction mixture at −78° C. After the temperature was raised to room temperature, the solvent was evaporated therefrom under reduced pressure to give the residue, and the resulting residue was purified by silica gel column chromatography (n-hexane-ethyl acetate) to obtain (2R,3S,4S,4aR,10bS)-7-(1-benzothien-2-ylmethyl)-3,4-dihydroxy-2-(hydroxymethyl)-3,4,4a,10b-tetrahydropyrano[3,2-c]isocumene-6(2H)-one (420 mg).

Example 1

1.58 Moles of n-hexane solution of n-butyllithium (2.4 ml) were added dropwise to a solution of benzo[b]thiophene (504 mg) in tetrahydrofuran (10 ml) at −78° C. in an argon atmosphere, and the mixture was stirred for two hours at the same temperature. To the reaction mixture was added dropwise a solution of 3-(2,3,4,6-tetra-0-benzyl-β-D-gluglucopyranosyl)benzaldehyde (1.57 g) in tetrahydrofuran (45 ml), and the mixture was stirred for five hours at the same temperature. Water (60 ml) was added to the reaction mixture, and extracted with ethyl acetate. The organic layer was dried over anhydrous sodium sulfate. After filtration, the solvent was evaporated from the filtrate under reduced pressure to give the residue. The residue was purified by silica gel column chromatography (n-hexane-ethyl acetate). Triethylsilane (0.67 ml) and a solution of boron trifluoride diethylether complex (447 ml) in dichloromethane (15 ml) were added dropwise to a solution of the residue (1.6 g) in dichloromethane (25 ml) under cooling with ice, and the mixture was stirred for two hours at the same temperature. Saturated sodium bicarbonate was added to the reaction mixture, and the organic layer was separated and dried over anhydrous magnesium sulfate. After filtration, the solvent was evaporated from the filtrate under reduced pressure to give the residue. The residue was purified by silica gel column chromatography (n-hexane-ethyl acetate) to obtain (1S)-1,5-anhydro-2,3,4,6-tetra-0-benzyl-1-[3-[(1-benzothien-2-yl)methyl]phenyl]-D-glucitol (1.56 g).

The compounds in Examples 2 to 16 were obtained in a manner similar to that of Example 1.

Example 17

1.58 Moles of n-hexane solution of n-butyllithium (1.18 ml) were added dropwise to a solution of 3-(4-methoxybenzyl) thiophene (0.38 g) in tetrahydrofuran (10 ml) at −78° C., and the mixture was stirred for one hour. To the reaction mixture was added dropwise a solution of 2,3,4,6-tetra-0-benzyl-D-(+)-glucono-1,5-lactone (1.0 g) in tetrahydrofuran (10 ml), and the mixture was stirred for one hour. 1.0 M hydrochloric acid was added to the reaction mixture, and extracted with ethyl acetate. After washing with saturated saline solution, the resultant was dried over anhydrous sodium sulfate. After filtration, the solvent was evaporated from the filtrate under reduced pressure to give the residue. The resulting residue was purified by silica gel column chromatography (n-hexane-chloroform-acetone). Triisopropylsilane (0.78 ml) and boron trifluoride diethylether complex (0.32 ml) were added to a solution of the residue (0.94 g) in chloroform (1.0 ml) and acetonitrile (5.0 ml) under cooling with ice, and the mixture was stirred for half an hour. Triethyl amine (1.0 ml) was added to the reaction mixture, and the solvent was evaporated therefrom under reduced pressure to give the residue. The resulting residue was purified by silica gel column chromatography (n-hexane-ethyl acetate) to obtain 1,4:5,9-dianhydro-6,7,8,10-tetra-0-benzyl-2,3-dideoxy-2(4-methoxybenzyl)-1-thio-D-glycero-D-glo-deca-1,3-dienitol (0.72 g).

The compounds in Examples 18 to 24 were obtained in a manner similar to that of Example 17.

Example 25

2-[3-Bromo-4-(methoxymethoxy)benzyl]-1-benzothiophene (17.4 g) was dissolved in tetrahydrofuran (200 ml). 1.58 Moles of n-hexane solution of n-butyl lithium (30.4 ml) were added dropwise to the mixture at −78° C., and the mixture was stirred for one hour at −78° C. Then, to the reaction mixture was added a solution of 2,3,4,6-tetra-0-benzyl-D-(+)-glucono-1,5-lactone (21.6 g) in tetrahydrofuran (150 ml), and the mixture was stirred for three hours at −78° C. The reaction mixture was washed with saturated ammonium chloride solution, and a water layer was extracted with ethyl acetate. The whole organic layer combined was dried over anhydrous sodium sulfate, and the solvent was evaporated therefrom under reduced pressure to give the residue. The obtained solid was recrystallized (hexane-ethyl acetate) to obtain 1-C-[5-(1-benzothien-2-ylmethyl)-2-(methoxymethoxy)phenyl]-2,3,4,6-tetra-0-benzyl-D-glucopyranose (25.3 g). This was dissolved in dichloromethane (500 ml). Triethylsilane (14.7 ml) and boron trifluoride diethylether complex (4.1 ml) were added to the solution at −40° C., and the mixture was stirred for four hours at −20° C. The reaction mixture was washed with saturated sodium bicarbonate, and a water layer was extracted with chloroform. The whole organic layer combined was dried with sodium sulfate, and the solvent was evaporated therefrom under reduced pressure to give the residue. The resulting residue was purified by silica gel column chromatography (n-hexane-ethyl acetate) to obtain (1S)-1,5-anhydro-1-[5-(1-benzothien-2-ylmethyl)-2-(methoxymethoxy)phenyl]-2,3,4,6-tetra-0-benzyl-D-glucitol (21.8 g).

The compounds in Examples 26 to 29 were obtained in a manner similar to that of Example 25.

Example 30

(1S)-1,5-Anhydro-1-[5-(1-benzothien-2-ylmethyl)-2-(methoxymethoxy)phenyl]-2,3,4,6-tetra-0-benzyl-D-glucitol (21.7 g) was dissolved in ethyl acetate (135 ml). To the mixture was added 4M hydrochloric acid-ethyl acetate solution (135 ml), and the mixture was stirred for 14 hours at room temperature. The reaction mixture was concentrated, and the resulting residue was purified by silica gel column chromatography (n-hexane-ethyl acetate) to obtain (1S)-1,5-anhydro-1-[5-(1-benzothien-2-ylmethyl)-2-hydroxyphenyl]-2,3,4,6-tetra-0-benzyl-D-glucitol (18.6 g).

The compounds in Examples 31 and 32 were obtained in a manner similar to that of Example 30.

Example 33

(1S)-1,5-Anhydro-1-[5-(1-benzothien-2-ylmethyl)-2-hydroxyphenyl]-2,3,4,6-tetra-0-benzyl-D-glucitol (763 mg) was dissolved in dimethylformamide (10 ml). To the mixture was added potassium carbonate (207 mg) and methyl iodide (0.095 ml), and the mixture was stirred for 16 hours at room temperature. The reaction mixture was diluted with sodium sulfate washed with water and saturated saline solution. The organic layer was dried with sodium sulfate, and the solvent was evaporated therefrom under reduced pressure to give the residue. The resulting residue was purified by silica gel column chromatography (n-hexane-ethyl acetate) to obtain (1S)-1,5-anhydro-1-[5-(1-benzothien-2-yl methyl)-2-methoxyphenyl]-2,3,4,6-tetra-0-benzyl-D-glucitol (736 mg).

The compounds in Examples 34 to 40 were obtained in a manner similar to that of Example 33.

Example 41

Tert-butyl[2-(4-(1-benzothien-2-ylmethyl)-2-(2,3,4,6-tetra-0-benzyl-β-D-glucopyranosyl)phenoxy)ethyl]carbamate (910 mg) was dissolved in tetrahydrofuran (20 ml), and lithium aluminum hydride (76 mg) was added to the mixture, and the mixture was stirred for seven hours under reflux condition. Aqueous solution of sodium hydroxide was added to the reaction mixture, and the precipitate was separated by filtration through celite. The filtrate was concentrate, and the resulting residue was diluted with chloroform and dried over sodium sulfate. The solvent was evaporated therefrom under reduced pressure to give the residue, and the obtained residue was purified by silica gel column chromatography (chloroform-methanol) to obtain (1S)-1,5-anhydro-1-[5-(1-benzothien-2-ylmethyl)-2-[2-methylamino]ethoxy]phenyl]-2,3,4,6-tetra-0-benzyl-D-glucitol (612 mg).

Example 42

Tert-butyl[2-(4-(1-benzothien-2-ylmethyl)-2-(2,3,4,6-tetra-0-benzyl-β-D-glucopyranosyl)phenoxy)ethyl]carbamate (906 mg) was dissolved in acetonitrile (10 ml), and methanol (0.08 ml), sodium iodide (300 mg), and acetyl chloride (0.28 ml), and the mixture was stirred for one hour at room temperature. To the mixture was added diisopropylethylamine (0.70 ml), and the mixture was stirred for 1.5 hours at room temperature. Further, acetyl chloride (0.14 ml) and diisopropylethylamine (0.35 ml) were added to the mixture, and the mixture was stirred for 14 hours at room temperature. The reaction mixture was diluted with 1M hydrochloric acid and extracted with diethyl ether. The organic layer was dried over sodium sulfate, and the solvent was evaporated therefrom under reduced pressure to give the residue. The residue was purified by silica gel column chromatography (n-hexane-ethyl acetate) to obtain N-[2-(4-(1-benzothien-2-yl methyl)-2-(2,3,4,6-tetra-0-benzyl-β-D-glucopyranosyl)phenoxy)ethyl]acetamide (387 mg).

Example 43

(1S)-1,5-Anhydro-1-[5-(1-benzothien-2-ylmethyl)-2-hydroxyphenyl]-D-glucitol (1.33 g) was dissolved in acetic anhydride-pyridine (1:2) (30 ml), and the mixture was stirred for 25 hours at room temperature. The reaction mixture was concentrated, and the obtained solid was washed with ethanol to obtain (1S)-2,3,4,6-tetra-0-acetyl-1,5-anhydro-1-[2-acetoxyphenyl-5-(1-benzothien-2-ylmethyl)-D-glucitol (1.93 g).

The compound in Example 44 was obtained in a manner similar to that of Example 43.

Example 45

(1S)-2,3,4,6-Tetra-0-acetyl-1,5-anhydro-1-[2-acetoxyphenyl-5-(1-benzothien-2-ylmethyl)-D-glucitol (1.93 g) was dissolved in acetonitrile (30 ml). 1,1,3,3-Tetramethylguanidine (1.6 ml) was added to the mixture, and the mixture was stirred for 2.5 hours at 50° C. The reaction mixture was concentrated, and the resulting residue was diluted with saturated ammonium chloride solution and extracted with ethyl acetate. The organic layer was dried over sodium sulfate. The solvent was evaporated therefrom under reduced pressure to give the residue. The resulting residue was purified by silica gel column chromatography (n-hexane-ethyl acetate) to obtain (1S)-2,3,4,6-tetra-0-acetyl-1,5-anhydro-1-[5-(1-benzothien-2-ylmethyl)-2-hydroxyphenyl]-D-glucitol (1.85 g).

The compound in Example 46 was obtained in a manner similar to that of Example 45.

Example 47

(1S)-2,3,4,6-Tetra-0-acetyl-1,5-anhydro-1-[5-(1-benzothien-2-ylmethyl)-2-hydroxyphenyl]-D-glucitol (570 mg) was dissolved in dimethylformamide (10 ml), and potassium carbonate (0.69 g), cyclopentyl bromide (0.54 ml), and potassium iodide (83 mg) were added to the mixture, and the mixture was stirred for two days at 50° C. The reaction mixture was diluted with ethyl acetate and washed with water. The organic layer was dried with sodium sulfate, and the solvent was evaporated therefrom under reduced pressure to give the residue. The resulting residue was purified by silica gel column chromatography (n-hexane-ethyl acetate) to obtain (1S)-2,3,4,6-tetra-0-acetyl-1,5-anhydro-1-[5-(1-benzothien-2-ylmethyl)-2-(cyclopentyloxy)phenyl]-D-glucitol (393 mg).

The compound in Example 48 was obtained in a manner similar to that of Example 47.

Example 49

(1S)-2,3,4,6-Tetra-0-acetyl-1,5-anhydro-1-[5-(1-benzothien-2-ylmethyl)-2-hydroxyphenyl]-D-glucitol (570 mg) was dissolved in tetrahydrofuran (10 ml). 2-propanol (0.38 ml), diethyl azodicarboxylato (0.63 ml), and triphenylphosphine (1.05 g) were added to the mixture, and the mixture was stirred for two days at room temperature. Further, 2-propanol (0.23 ml), diethyl azodicarboxylato (0.31 ml), and triphenylphosphine (0.52 g) were added to the mixture, and the mixture was stirred for four hours at room temperature. The reaction mixture was concentrated, and the residue was purified by silica gel column chromatography (n-hexane-ethyl acetate) to obtain (1S)-2,3,4,6-tetra-0-acetyl-1,5-anhydro-1-[5-(1-benzothien-2-ylmethyl)-2-(isopropyloxy)phenyl]-D-glucitol (544 mg).

Example 50

Sodium hydride (60%) is suspended in dimethylsulfoxide (3 ml), and the mixture was stirred for half an hour at 60° C. To the mixture was added a solution of (1S)-2,3,4,6-tetra-0-acetyl-1,5-anhydro-1-[5-(1-benzothien-2-ylmethyl)-2-hydroxyphenyl]-D-glucitol (571 mg) in dimethylsulfoxide (2 ml), and the mixture was stirred for one hour at room temperature. Then, (S)-(-)-4-chloro methyl-2,2-dimethyl-1,3-dioxolane (0.21 ml), and the mixture was stirred for seven hours at 80° C. The reaction mixture was diluted with water and extracted with dichloromethane. The organic layer was dried over sodium sulfate, and the solvent was evaporated therefrom under reduced pressure to give the residue. The resulting residue was purified by silica gel column chromatography (n-hexane-ethyl acetate) to obtain (1S)-2,3,4,6-tetra-0-acetyl-1,5-anhydro-1-[5-(1-benzothien-2-yl methyl)-2-{[(4R)-2,2-dimethyl-1,3-dioxolane-4-yl]methoxy}phenyl)-D-glucitol (77 mg).

Example 51

2,6-Lutidine (3.98 ml) and trifluoromethanesulfonic anhydride (3.45 ml) were added to a solution of (1S)-1,5-anhydro-1-[5-(benzothien-2-ylmethyl)-2-hydroxyphenyl]-2,3,4,6-tetra-0-benzyl-D-glucitol (13.1 g) in dichloromethane (150 ml) cooled at −20° C. under an argon atmosphere, and the mixture was stirred for three hours. To the mixture were further added 2,6-lutidine (2.00 ml) and trifluoromethanesulfonic anhydride (1.73 ml), and the mixture was stirred for one hour. Aqueous solution of saturated sodium bicarbonate was added to the mixture, and extracted three times with chloroform. The organic layer was washed with water and saturated saline solution and dried over anhydrous magnesium sulfate. The solid was removed by filtration, and the solvent was evaporated from the filtrate under reduced pressure to give the residue. The residue was purified by silica gel column chromatography (n-hexane-ethyl acetate) to obtain (1S)-1,5-anhydro-1-[5-(benzothien-2-ylmethyl)-2-trifluoromethanes ulfonylphenyl]-2,3,4,6-tetra-0-benzyl-D-glucitol (13.9 g).

Example 52

(1S)-1,5-Anhydro-1-[5-(benzothien-2-ylmethyl)-2-trifluorome thanesulfonylphenyl]-2,3,4,6-tetra-0-benzyl-D-glucitol (5.67 g) was dissolved in a mixed solvent of dimethylsulfoxide (30 ml) and methanol (25 ml). Palladium acetate (II) (285 mg), 1,3-bis(diphenylphosphino)propane (524 mg), and triethyl amine (1.94 ml) was added to the mixture, and the mixture was stirred for two days at 55° C. in a carbon monoxide atmosphere. The mixture was cooled to room temperature and then extracted three times with ethyl acetate. The organic layer was washed with water two times and saturated saline solution and dried over anhydrous magnesium sulfate. The solid was removed by filtration, and the solvent was evaporated the filtrate under reduced pressure to give the residue. The residue was purified by silica gel column chromatography (n-hexane-ethyl acetate) to obtain methyl 4-(1-benzothien-2-ylmethyl)-2-(2,3,4,6-tetra-0-benzyl-β-D-glucopyranosyl)benzoate (2.74 g).

Example 53

Methyl 4-(1-benzothien-2-ylmethyl)-2-(2,3,4,6-tetra-0-benzyl-β-D-glucopyranosyl)benzoate (5.26 g) is dissolved in tetrahydrofuran (5 ml). Methanol (10 ml) and aqueous solution of 10M sodium hydroxide (10 ml) was added to the mixture, and the mixture was stirred for 21 hours at 60° C. The reaction mixture was cooled to room temperature, and acidified by addition of 6M hydrochloric acid, and thereafter extracted three times with chloroform. The organic layer was washed with saturated saline solution and dried over anhydrous magnesium sulfate. The solid was removed by filtration, and the solvent was evaporated from the filtrate under reduced pressure to give the residue. The residue was subjected to vacuum drying to obtain 4-(1-benzothien-2-yl methyl)-2-(2,3,4,6-tetra-0-benzyl-β-D-glucopyranosyl)benzoic acid (5.13 g).

The compound in Example 54 was obtained in a manner similar to that of Example 53.

Example 55

Oxarylchloride (0.16 ml) and a drop of dimethylformamide was added to a solution of [4-(1-benzothien-2-ylmethyl)-2-(2,3,4,6-tetra-0-benzyl-β-D-glucopyranosyl)phenoxy]acetic acid (770 mg) in dichloromethane (10 ml) under cooling with ice, and the mixture was stirred for two hours at room temperature. The reaction mixture was subjected to evaporation under reduced pressure, and the residue obtained was dissolved in dichloromethane (15 ml). 28% aqueous ammonia (10 ml) was added to the solution, and the mixture was stirred for one hour at room temperature. The organic layer was separated and dried over magnesium sulfate. The solvent was evaporated therefrom under reduced pressure to give the residue to obtain [4-(1-benzothien-2-ylmethyl)-2-(2,3,4,6-tetra-0-benzyl-β-D-glucopyranosyl)phenoxy]acetamide (740 mg).

The compound in Example 56 was obtained in a manner similar to that of Example 55.

Example 57

4-(1-Benzothien-2-ylmethyl)-2-(2,3,4,6-tetra-0-benzyl-β-D-glucopyranosyl)benzoic acid (2.23 g) was dissolved in toluene (20 ml), and triethylamine (0.590 ml) was added to the solution, and the mixture was cooled to 0° C. Diphenylphosphorylazide (0.67 ml) was added dropwise gradually to the mixture, and the mixture was stirred for 2.5 hours at room temperature. The reaction mixture was diluted with toluene, and then was washed with aqueous solution of 1% sodium hydrogencarbonate and saturated saline solution and dried over anhydrous magnesium sulfate. The solid was removed by filtration, and the solvent was evaporated the filtrate under reduced pressure to give the residue. The residue was dissolved in toluene (20 ml), and the mixture was stirred for three hours at 130° C. 2-Propanol (30 ml) was further added to the mixture, and the mixture was stirred for 16 hours at 110° C. The mixture was cooled to room temperature, and water was added to the mixture, and extracted three times with chloroform. The organic layer was washed with saturated saline solution and dried over anhydrous magnesium sulfate. The solid was removed by filtration, and the solvent was evaporated from the filtrate under reduced pressure to give the residue. The residue was purified by silica gel column chromatography (n-hexane-ethyl acetate) to obtain tert-butyl 4-(1-benzothien-2-ylmethyl)-2-(2,3,4,6-tetra-0-benzyl-β-D-glucopyranosyl)phenylcarbamate (1.50 g).

Example 58

Tert-butyl 4-(1-benzothien-2-ylmethyl)-2-(2,3,4,6-tetra-0-benzyl-β-D-glucopyranosyl)phenylcarbamate (1.11 g) was dissolved in ethyl acetate (3 ml). 4M Ethyl acetate hydrochloride (3 ml) was added to the mixture under cooling with ice, and the temperature of the mixture was raised to room temperature. Then, the mixture was stirred for three hours. Aqueous solution of 1M sodium hydroxide was added to the mixture, and extracted three times with chloroform. The organic layer was washed with aqueous solution of 1M sodium hydroxide and saturated saline solution and dried over anhydrous magnesium sulfate. The solid was removed by filtration, and the solvent was evaporated the filtrate under reduced pressure to give the residue. The residue was purified by silica gel column chromatography (n-chloroform-methanol-aqueous ammonia) to obtain (1S)-1,5-anhydro-1-[2-amino-5-(1-benzothien-2-ylmethyl)phenyl]-2-(2,3,4,6-tetra-0-benzyl-D-glucitol (576 mg).

Example 59

Lithium aluminum hydride (68 mg) was added to anhydrous tetrahydrofuran (15 ml) under an argon atmosphere, and a solution of tert-butyl 4-(1-benzothien-2-ylmethyl)-2-(2,3,4,6-tetra-0-benzyl-β-D-glucopyranosyl)phenylcarbamate (1.27 g) in anhydrous tetrahydrofuran (15 ml) was gradually added dropwise to the mixture. The reaction mixture was stirred for two hours at 75° C. After the reaction was completed, the mixture was cooled to room temperature. Water (1.0 ml), aqueous solution of 15% sodium hydroxide (10 ml), and water (3.0 ml) were added in order, and the mixture was stirred at room temperature. The solid was removed by filtration through celite, and the solvent was evaporated from the filtrate under reduced pressure to give the residue. Chloroform was added to the mixture, and the mixture was washed with saturated saline solution and dried over anhydrous magnesium sulfate. The solid was removed by filtration, and the solvent was evaporated the filtrate under reduced pressure to give the residue. The residue was purified by silica gel column chromatography (n-hexane-ethyl acetate) to obtain (1S)-1,5-anhydro-1-[5-(1-benzothien-2-ylmethyl)-2-(methylamino)phenyl]-2-(2,3,4,6-tetra-0-benzyl-D-glucitol (737 mg) as achromatic viscous matter.

The compounds in Example 60 to 62 were obtained in a manner similar to that of Example 59.

Example 63

Phthalimide (294 mg), triphenylphosphine (525 mg), and diethlazodicarboxylate (0.32 ml) were added to a solution of (1S)-1,5-anhydro-1-[5-(1-benzothien-2-ylmethyl)-2-(hydroxyl ethoxy)phenyl]-2-(2,3,4,6-tetra-0-benzyl-D-glucitol (1.35 g) in tetrahydrofuran (20 ml), and the mixture was stirred for six hours at room temperature. Silica gel (3 g) was added to the reaction mixture, and the mixture was dry-solidified under reduced pressure and purified by column chromatography. The residue was dissolved in tetrahydrofuran (15 ml) and ethanol (15 ml). Hydrazine hydrate (0.54 ml) was added dropwise to the mixture, and the mixture was stirred for 24 hours at room temperature. After insoluble matter was separated by filtration, the filtrate was concentrated to obtain the residue. Chloroform was added to the residue, and insoluble matter was further separated by filtration. The filtrate was washed with water, dried over magnesium sulfate, and concentrated. The residue obtained was purified by silica gel column chromatography to obtain (1S)-1,5-anhydro-1-[2-(aminoethoxy)-5-(1-benzothien-2-ylmethyl)phenyl]-2,3,4,6-tetra-0-benzyl-D-glucitol (960 mg).

Example 64

(1S)-1,5-Anhydro-1-[5-(1-benzothien-2-ylmethyl)-2-(methylamino)phenyl]-2,3,4,6-tetra-0-benzyl-D-glucitol (179 mg) was dissolved in dichloromethane (3 ml). 35% Formalin (0.008 ml) and acetic acid (0.02 ml) were added to the mixture, and the mixture was stirred at room temperature.

Sodium triacetoxy boronhydride (74 mg) was added to the mixture, and the mixture was stirred for 11 hours. Aqueous solution of saturated sodium hydrogencarbonate was added to the reaction mixture, and extracted three times with chloroform after decomposition of the excessive reagent. The organic layer was washed with saturated saline solution and dried over anhydrous magnesium sulfate. The solid was removed by filtration, and the solvent was evaporated from the filtrate under reduced pressure to give the residue. The residue was purified by silica gel column chromatography (n-hexane-ethyl acetate) to obtain (1S)-1,5-anhydro-1-[5-(1-benzothien-2-ylmethyl)-2-(dimethylamino)phenyl]-2,3,4,6-tetra-0-benzyl-D-glucitol (124 mg).

Example 65

A solution of 1.58 M n-hexane (2.2 ml) of n-butyl lithium was added dropwise to a solution of [1-benzothien-2-yl(5-bromo-2-fluorophenyl)methoxy](tert-butyl)dimethylsilane (1.50 g) in anhydrous tetrahydrofuran (15 ml) cooled at −78° C. under an argon atmosphere, and the mixture was stirred for half an hour. Then, a solution of 2,3,4,6-tetra-0-benzylgluconolactone (1.90 g) in anhydrous tetrahydrofuran (20 ml) was added to the reaction mixture, and the mixture was stirred for 1.5 with gradually raising the temperature from −78° C. to 0° C. Aqueous solution of saturated ammonium chloride was added to the mixture, and extracted three times with ethyl acetate. The organic layer was washed with aqueous solution of saturated ammonium chloride and saturated saline solution and dried over anhydrous magnesium sulfate. The solid was removed by filtration, and the solvent was evaporated from the filtrate under reduced pressure to give the residue. The residue was purified by silica gel column chromatography (chloroform-n-hexane-acetone). The residue (1.52 g) obtained was dissolved in dehydrated tetrahydrofuran (15 ml). A solution of tetra-n-butyl ammonium fluoride in 1.0 M tetrahydrofuran (2.0 ml) was added to the mixture, and the mixture was stirred for 65 minutes at room temperature. After the solvent was evaporated therefrom under reduced pressure to give the residue, the residue was purified by silica gel column chromatography (n-hexane-ethyl acetate). Triethylsilane (0.239 ml) and borontrifluoride diethyl ether complex (0.175 ml) were added to a solution of the residue (500 mg) obtained in acetonitrile (5 ml), and the mixture was stirred for five hours. To the mixture was added aqueous solution of saturated sodium hydrogencarbonate, and then extracted three times with chloroform after decomposition of excessive reagent. The organic layer was washed with aqueous solution of saturated sodium hydrogencarbonate and saturated saline solution, and dried over anhydrous sodium sulfate. The solid was removed by filtration, and the solvent was evaporated from the filtrate under reduced pressure to give the residue to give the residue. The residue was purified by silica gel column chromatography (n-hexane-ethyl acetate) to obtain 1,5-anhydro-1-[3-(1-benzothien-2-ylmethyl)-4-fluorophenyl]-2,3,4,6-tetra-0-benzyl-D-glucitol (150 mg) as light-yellow viscous matter.

The compounds in Examples 66 to 68 were obtained in a manner similar to that of Example 65.

Example 69

Magnesium (granules; 131 mg), and 1,2-dibromoethane (a drop) were added to tetrahydrofuran (10 ml) under an argon atmosphere. A solution of 2-(1-benzothien-2-ylmethyl)-4-bromophenyl methyl ether (1.5 g) in tetrahydrofuran (15 ml) was gradually added dropwise to the mixture, and the temperature was raised from room temperature to 60° C. to prepare a Grignard reagent. After cooling to room temperature, a solution of 2,3,4,6-tetra-0-benzyl-D-(+)-glucono-1,5-lactone (2.91 g) in tetrahydrofuran (20 ml) was added to the reagent, and the mixture was stirred for three hours. Aqueous solution of saturated ammonium chloride was added to the mixture, and extracted three times with ethyl acetate. The organic layer was washed with aqueous solution of saturated ammonium chloride and saturated saline solution and dried over anhydrous magnesium sulfate. The solid was removed by filtration, and the solvent was evaporated from the filtrate under reduced pressure to give the residue. The residue was purified by silica gel column chromatography (n-hexane-ethyl acetate). Triethylsilane (0.146 ml) and boron trifluoride-diethyl ether complex (0.105 ml) was added to a solution of the residue (600 mg) obtained in acetonitrile (6 ml) at −20° C., and the mixture was stirred for three hours. Triethylsilane (0.073 ml) and boron trifluoride-diethyl ether complex (0.048 ml) was further added to the mixture. The temperature was raised to −10° C., and the mixture was stirred for two hours. Aqueous solution of saturated sodium hydrogencarbonate was added to the mixture to decompose superfluous reagent, and extracted three times with chloroform. The organic layer was washed with saturated saline solution and dried over anhydrous magnesium sulfate. The solid was removed by filtration, and the solvent was evaporated from the filtrate under reduced pressure to give the residue. The residue was purified by silica gel column chromatography (n-hexane-ethyl acetate) to obtain (1S)-1,5-anhydro-1-[3-(1-benzothien-2-ylmethyl)-4-methoxyphenyl]-2,3,4,6-tetra-0-benzyl-D-glucitol (394 mg).

The compound in Example 70 was obtained in a manner similar to that of Example 69.

Example 71

A solution of 2-bromopyridine (342 mg) in tetrahydrofuran (13 ml) was added dropwise to a solution of 1.59 M hexane (1.36 ml) of n-butyl lithium at −78° C. under an argon atmosphere, and the mixture was stirred for one hour at the same temperature. Then, a solution of 3-(2,3,4,6-tetra-0-benzyl-β-D-gluglucopyranosyl)benzaldehyde (1.13 g) in tetrahydrofuran (35 ml) was added dropwise to the mixture, and the mixture was stirred for 2.5 hours. Water (40 ml) was added to the reaction mixture, and extracted with ethyl acetate, and the organic layer was dried over anhydrous magnesium sulfate. After filtration, the solvent was evaporated from the filtrate under reduced pressure to give the residue, and the resulting residue was purified by silica gel column chromatography (n-hexane-ethyl acetate) to obtain (1S)-1,5-anhydro-2,3,4,6-tetra-0-benzyl-1-[3-[hydroxy(pyridine-2-yl)methyl]phenyl]-D-glucitol (0.99 g). Sodium hydride (60%) (202 mg) was added to a solution of (1S)-1,5-anhydro-2,3,4,6-tetra-0-benzyl-1-[3-[hydroxy(pyridine-2-yl)methyl]phenyl]-D-glucitol (1.78 g) in tetrahydrofuran (12 ml) at room temperature, and the mixture was stirred for half an hour. Carbon disulfide (1.15 ml) was added dropwise to the mixture under cooling with ice, and the mixture was stirred for two hours at the same temperature and further two hours at room temperature. Methyl iodide (0.28 ml) was added dropwise to the reaction mixture under cooling with ice, and the mixture was stirred for 2.5 hours at the same temperature. Water was added to the reaction mixture, and extracted with ethyl acetate. The organic layer was dried over anhydrous magnesium sulfate. After filtration, the solvent was evaporated from the filtrate under reduced pressure to give the residue, and the residue was dissolved in toluene (20 ml). Tributyltin hydride (3.28 ml) and α', α'-azoisobutyronitrile (82 mg) were added to the mixture, and the mixture was stirred for 64 hours under reflux condition. The solvent was evaporated from the filtrate under reduced pressure to give the residue, and the residue was purified by silica gel column chromatography (n-hexane-ethyl acetate) to obtain (1S)-1,5-anhydro-2,3,4,6-tetra-0-benzyl-1-[3-[(pyridine-2-yl)methyl]phenyl]-D-glucitol (1.51 g).

The compound in Example 72 was obtained in a manner similar to that of Example 71.

Example 73

(1S)-1,5-Anhydro-2,3,4,6-tetra-0-benzyl-1-[3-[(hydroxylmethyl)phenyl]-D-glucitol (631 mg) and phthalimide (154 mg) were dissolved in tetrahydrofuran (10 ml). Diethylazodicarboxylate (0.18 ml) and triphenylphosphine (303 mg) were added to the mixture under cooling with ice, and the mixture was stirred for 20 hours at room temperature. The reaction mixture was concentrated, and the residue was purified by silica gel column chromatography (n-hexane-ethyl acetate) to obtain (1S)-1,5-anhydro-2,3,4,6-tetra-0-benzyl-1-C-{3-[(1,3-dioxo-1,3-dihydro-2H-isoindole-2-yl)methyl]phenyl}-D-glucitol (784 mg).

Example 74

1,2-Dibromoethane (one drop) was added to a solution of zinc dust (86 mg) in tetrahydrofuran (2.0 ml) in an argon atmosphere, and the solution was refluxed for five minutes. Chloro-trimethylsilane (a drop) was added to the mixture at room temperature, and the mixture was stirred for 15 minutes. Then, (1S)-2,3,4,6-tetra-0-acetyl-1,5-anhydro-1-(3-bromomethyl-6-methoxy)phenyl-D-glucitol (700 mg) was added to the mixture, and the mixture was refluxed for one hour. 2-bromo-1H-indene (128 mg) and tetrakis(triphenylphosphine) palladium (76 mg) were added to the mixture, and the mixture was heat-refluxed for five hours. The temperature of the mixture was cooled to room temperature, and aqueous solution of saturated ammonium chloride was added. The insoluble matter was separated by filtration, and the filtrate was extracted with ethyl acetate. The organic layer was washed with saturated saline solution and dried with anhydrous sodium sulfate. After filtration, the solvent was evaporated from the filtrate under reduced pressure to give the residue, and the residue was purified by silica gel column chromatography (chloroform-ethyl acetate) to obtain (1S)-2,3,4,6-tetra-0-acetyl-1,5-anhydro-1-[3-[(1H-indene-2-yl)methyl-6-methoxy]phenyl]-D-glucitol (190 mg).

The compounds in Examples 75 to 79 were obtained in a manner similar to that of Example 74.

Example 80

Active zinc (131 mg) was suspended in tetrahydrofuran (2 ml). 1,2-dibromoethane (0.07 ml) was added to the suspension, and the suspension was stirred for five minutes at 60° C. Then, trimethylsilyl chloride (0.10 ml) was added to the mixture, and the mixture was stirred for 10 minutes at room temperature. Subsequently, a solution of (1S)-1,5-anhydro-2,3,4,6-tetra-0-benzyl-[3-(bromomethyl)phenyl]-D-glucitol (694 mg) in tetrahydrofuran (3 ml) was added to the mixture, and the mixture was stirred for one hour at 60° C. Then, 2-(methylthio) benzothiazole (181 mg) and tetrakis(triphenylphosphine) palladium (231 mg) were added to the mixture, and the mixture was stirred for 15 hours at 60° C. After the precipitate was separated by filtration, the filtrate was concentrated. The residue obtained was diluted with ethyl acetate and washed with saturated aqueous sodium bicarbonate and saturated saline solution. The organic layer was dried over sodium sulfate, and the solvent was evaporated therefrom under reduced pressure to give the residue. The residue was purified by silica gel column chromatography (n-hexane-ethyl acetate) to obtain (1S)-1,5-anhydro-2,3,4,6-tetra-0-benzyl-1-[3-(1,3-benzothiazole-2-ylmethyl)phenyl]-D-glucitol (355 mg).

Example 81

1,4-Dioxane (10 ml) suspension of (1S)-2,3,4,6-tetra-0-acetyl-1,5-anhydro-1-[3-(bromomethyl)phenyl]-D-glucitol (501 mg), 1-methyl-2-(tributylstanyl)-1H-indole (546 mg), tris(dibenzylidene-acetone)dipalladium (92 mg), 2-(dicyclohexylphosphino)biphenyl (88 mg), potassium fluoride (174 mg), and cesium carbonate (652 mg) was stirred for 18 hours at 60° C. The insoluble matter was removed by filtration, and the solvent was evaporated from the filtrate to give the residue. The residue obtained was subjected to silica gel column chromatography to obtain (1S)-2,3,4,6-tetra-0-acetyl-1,5-anhydro-1-{3-[(1-methyl-1H-indole-2-yl)methyl]phenyl}-D-glucitol (280 mg).

The compounds in Examples 82 to 91 were obtained in a manner similar to that of Example 81.

Example 92

Tetrakistriphenylphosphinepalladium(0) (43 mg) and dimethyl-1-benzothien-3-ylboronate (132 mg) to a solution of 1-(2,3,4,6-tetra-0-benzyl-β-D-glucopyranosyl)-3-(trifluoro methanesulfonyl)benzene (280 mg) in toluene (10 ml) at room temperature. Aqueous solution of saturated sodium bicarbonate (4 ml) was further added to the mixture, and the mixture was stirred for four hours at 90° C. Ethyl acetate and saturated saline solution were added to the reaction mixture, the insoluble matter was subjected to filtration through celite, and the organic layer was extracted. The organic layer was washed with water and saturated saline solution, dried over anhydrous magnesium sulfate, and concentrated to give the residue. The resulting residue was purified by silica gel column chromatography (n-hexane-ethyl acetate) to obtain (1S)-1,5-anhydro-1-[3-(1-benzothien-3-yl)phenyl]-2,3,4,6-tetra-0-benzyl-D-glucitol (170 mg).

Example 93

Twenty percents of palladium hydroxide/carbon (800 mg) were added to a suspension of 1,4:5,9-dianhydro-6,7,8,10-tetra-0-benzyl-2,3-dideoxy-2-(4-methoxybenzyl)-1-thio-D-glycero-D-deca-1,3-dienitol (0.72 g) in tetrahydrofurane (5.0 ml) and hydrochloric acid in 2% methanol solution (10 ml), and the mixture was stirred for 18 hours at hydrogen atmosphere (1 atm). The reaction mixture was filtrated through celite, and the filtrate was concentrated. Then, pyridine (3.0 ml) and acetic anhydride (1.5 ml) were added to the residue, and the mixture was stirred over night at room temperature. The solvent was evaporated therefrom under reduced pressure, and the resultant was co-evaporated with toluene. The resulting residue was purified by silica gel column chromatography (n-hexane-ethyl acetate) to obtain 6,7,8,10-tetra-0-acetyl-1,4:5,9-dianhydro-2,3-dideoxy-2-(4-methoxybenzyl)-1-thio-D-glycero-D-deca-1,3-dienitol (0.13 g).

Example 94

0.76 Mole of tetrahydrofuran solution of isopropylmagnesium bromide (27.6 ml) was added dropwise to a solution of 2-(4-ethylbenzyl)-1H-pyrrole (4.14 g) in tetrahydrofuran (10 ml), and the mixture was stirred for two hours. To the mixture was added dropwise 2,3,4,6-tetra-0-benzyl-D-glucopyranosyl fluoride (3.80 g), and the mixture was stirred for five hours. Aqueous solution of saturated ammonium chloride was added to the reaction mixture, and extracted with ethyl acetate. The organic layer was washed with saturated saline solution and dried over anhydrous sodium sulfate. After filtration, the solvent was evaporated from the filtrate under reduced pressure to give the residue. The residue was purified by silica gel column chromatography (n-hexane-ethyl acetate) to obtain (1S)-1,5-anhydro-2,3,4,6-tetra-0-benzyl-1-[5-(4-ethyl benzyl)-1H-pyrrole-2-yl]-D-glucitol (1.89 g).

Example 95

Fifteen mg of sodium hydride (60%) were added to a solution of (1S)-1,5-anhydro-2,3,4,6-tetra-0-benzyl-1-[5-(4-ethylbenzyl)-1H-pyrrole-2-yl]-D-glucitol (210 mg) in dimethylformamide (3.0 ml), and the mixture was stirred for 15 minutes at room temperature. Then, methyl iodide (0.185 ml) was added to the mixture, and the mixture was stirred for half an hour. Water was added to the reaction mixture, and extracted with diethyl ether. The organic layer was washed with water and saturated saline solution and dried over anhydrous sodium sulfate. After filtration, the solvent was evaporated from the filtrate under reduced pressure to give the residue. The residue was purified by silica gel column chromatography (n-hexane-ethyl acetate) to obtain (1S)-1,5-anhydro-2,3,4,6-tetra-0-benzyl-1-[5-(4-ethylbenzyl)-1-methyl-1H-pyrrole-2-yl]-D-glucitol (143 g).

Example 96

(1S)-1,5-Anhydro-2,3,4,6-tetra-0-benzyl-1-(1H-pyrrole-2-yl)-D-glucitol (773 mg) was added to a suspension of tetrabutyl ammonium bromide (42.2 mg) and potassium hydroxide (150 mg) in benzene (5.0 ml), and 4-ethylbenzyl bromide (331 mg) was added to the mixture. The mixture was stirred for two hours at room temperature. Water was added to the reaction mixture, and extracted with ethyl acetate. The organic layer was washed with saturated saline solution and dried over anhydrous sodium sulfate. After filtration, the solvent was evaporated from the filtrate under reduced pressure to give the residue. The resulting residue was purified by silica gel column chromatography (n-hexane-ethyl acetate) to obtain (1S)-1,5-anhydro-2,3,4,6-tetra-0-benzyl-1-[1-(4-ethylbenzyl)-1H-pyrrole-2-yl]-D-glucitol (695 mg).

Example 97

Triethylamine (0.6 ml) was added to a solution of (1S)-2,3,4,6-tetra-0-acetyl-1,5-anhydro-1-(1H-tetrazole-5-yl)-D-glucitol (0.85 g) in tetrahydrofuran (10.0 ml), and 4-ethylbenzyl bromide (0.50 g) was added to the mixture. The mixture was stirred for 17 hours at room temperature. Water was added to the reaction mixture, and extracted with ethyl acetate. The organic layer was washed with water and saturated saline solution and dried over anhydrous magnesium sulfate. After filtration, the solvent was evaporated from the filtrate under reduced pressure to give the residue. The resulting residue was purified by silica gel column chromatography (n-hexane-ethyl acetate) to obtain (1S)-2,3,4,6-tetra-0-acetyl-1,5-anhydro-1-[2-(4-ethylbenzyl)-1H-tetrazole-5-yl]-D-glucitol (0.22 g).

Example 98

2,3,4,6-Tetra-0-benzyl-1-C-(3,5-dichloropyrazine-2-yl)-D-glucopyranose (7.93 g) was dissolved in dichloromethane (90 ml), and triethylsilane (36.8 ml) and trifluoroacetic acid (17.7 ml) were added to the mixture, and the mixture was stirred for 19 days at room temperature. The reaction mixture was washed with saturated sodium bicarbonate, and the water layer was extracted with chloroform. The whole organic layer combined was dried over sodium sulfate, and the solvent was evaporated from the filtrate under reduced pressure to give the residue. The resulting residue was purified by silica gel column chromatography (n-hexane-ethyl acetate) to obtain (1S)-1,5-anhydro-2,3,4,6-tetra-0-benzyl-1-(3,5-dichloropyrazine-2-yl)-D-glucitol (2.15 g).

Example 99

1.58 Moles of n-hexane solution (2.15 ml) of n-butyllithium were diluted with tetrahydrofuran (20 ml), and 2,2,6,6-tetramethyl piperidine (0.64 ml) was added dropwise to the solution at −78° C., and the mixture was stirred for one hour at 0° C. Subsequently, a solution of (1S)-1,5-anhydro-2,3,4,6-tetra-0-benzyl-1-(3,5-dichloropyrazine-2-yl)-D-glucitol (2.09 g) in tetrahydrofuran (20 ml) was added to the mixture at −78° C., and the mixture was stirred for one hour at −78° C. Then, 4-ethylbenzaldehyde (1.28 ml) was added to the mixture, and the mixture was stirred for 1.5 hours at −78° C. The reaction mixture was washed with saturated aqueous ammonium chloride, and the water layer was extracted with diethyl ether. The whole organic layer combined was dried over sodium sulfate, and the solvent was evaporated therefrom under reduced pressure to give the residue. The resulting residue was purified by silica gel column chromatography (n-hexane-ethyl acetate) to obtain (1S)-1,5-anhydro-2,3,4,6-tetra-0-benzyl-1-(3,5-dichloro-6-[(4-ethylphenyl)(hydroxy)methyl]pyrazine-2-yl)-D-glucitol (842 mg).

Example 100

Pentamethylbenzene (1.57 g) and 1.0 M n-heptane solution (2.97 ml) of boron trichloride were added to a solution of (1S)-1,5-anhydro-1-[3-[(5-methyl-1-benzothien-2-yl)methyl]phenyl]-2,3,4,6-tetra-0-benzyl-D-glucitol (538 mg) in dichloromethane (25 ml), and the mixture was stirred for one hour. After the reaction was completed, methanol (5 ml) was added to decompose excessive reagent, and the resultant was subjected to evaporation under reduced pressure to remove solvent and give the residue. The residue was purified by silica gel column chromatography (chloroform-methanol) to obtain (1S)-1,5-anhydro-1-[3-[(5-methyl-1-benzothien-2-yl)methyl]phenyl]-D-glucitol (274 mg).

The compounds in Examples 101 to 153 were obtained in a manner similar to that of Example 100.

Example 154

1 Mole of n-heptane solution of borontribromide (4.54 ml) was added dropwise to a solution of (1S)-1,5-anhydro-2,3,4,6-tetra-0-benzyl-1-[3-[(benzothiophene-2-yl)methyl]phenyl]-D-glucitol (0.77 g) and pentamethylbenzene (2.3 g) in dichloromethane (20 ml) at −78° C. in an argon atmosphere, and the mixture was stirred for 90 minutes. Methanol was added dropwise to the reaction mixture at −78° C., and the mixture was stirred till the temperature became room temperature. The solvent was evaporated therefrom under reduced pressure to give the residue, and methanol (20 ml) was further added thereto, and concentrated to give the residue. Then, toluene was added for further thereto, and concentrated to give the residue. The resulting residue was purified by silica gel column chromatography (chloroform-methanol) to obtain yellow amorphous (390 mg). This was further purified by a reversed-phase column chromatography to obtain (1S)-1,5-anhydro-1-[3-[(1-benzo thiophene-2-yl)methyl]phenyl]-D-glucitol (270 mg).

The compound in Example 155 was obtained in a manner similar to that of Example 154.

Example 156

(1S)-2,3,4,6-Tetra-0-acetyl-1,5-anhydro-1-[5-(1-benzo thiophene-2-ylmethyl)-2-(cyclopentyloxy)phenyl]-D-glucitol (381 mg) was dissolved in methanol (10 ml). Sodium methoxide (32 mg) was added to the solution, and the mixture was stirred for three hours at room temperature. The reaction mixture was neutralized with acid ion-exchange resin, and the resin was separated by filtration. The filtrate was concentrated, and the resulting residue was purified by silica gel column chromatography (chloroform-methanol) to obtain (1S)-1,5-anhydro-1-[5-(1-benzothien-2-yl)methyl]-2-(cyclopentyloxy)phenyl]-D-glucitol (215 mg).

The compounds in Examples 157 to 178 were obtained in a manner similar to that of Example 156.

Example 179

(1S)-1,5-Anhydro-1-{5-[1-benzothien-2-ylmethyl]-2-[(2-dimethylamino)ethoxy]phenyl}-2,3,4,6-tetra-0-benzyl-D-glucitol (520 mg) was dissolved in dichloromethane (25 ml). After pentamethylbenzene (1.39 g) was added to the solution, the resultant was cooled to −78° C. 1.0 Mole of n-heptane solution (3.4 ml) of boron trichloride was added thereto, and the resultant mixture was stirred for four hours at −78° C. Methanol was added to the reaction mixture, and the solvent was evaporated therefrom under reduced pressure to give the residue. A mixed solution of toluene-diethyl ether (1:1) was added thereto, and extracted with aqueous solution of saturated sodium hydrogencarbonate. Water was evaporated under reduced pressure, and the residue was purified by a reversed-phase column chromatography (methanol-water). Finally, the solid obtained was washed with diethyl ether to obtain (1S)-1,5-anhydro-1-{5-[1-benzothien-2-yl methyl]-2-[(2-dimethyl amino)ethoxy]phenyl}-D-glucitol (104 mg).

Example 180

1 Mole of aqueous solution of sodium hydroxide (1.5 ml) was added to (2R,3S,4S,4aR,10bS)-7-(1-benzothien-2-ylmethyl)-3,4-dihydroxy-hydroxymethyl)-3,4,4a,10b-tetrahydropyrano[3,2-c]isocumene-6(2H)-one (80 mg), and the mixture was stirred for two hours. Then, the reaction mixture was neutralized by adding 1 M aqueous solution of hydrochloric acid (1,5 ml) The reaction mixture was concentrated, and the residue was purified by a reversed-phase column chromatography (water-methanol) to obtain 4-(1-benzothien-2-ylmethyl)-2-(β-D-glucopyranosyl)benzoic acid (67 mg).

Example 181

N-Methylmorpholine (412 mg) and chlorotrimethylsilane (295 mg) were added to a solution of (2R,3S,4S,4aR,10bS)-7-(1-benzothien-2-ylmethyl)-3,4-dihydroxy-2-hydroxymethyl)-3,4,4a,10b-tetrahydropyrano[3,2-c]isocumene-6 (2H)-one (280 mg) in tetrahydrofuran (14 ml) at −5° C., and the mixture was stirred for 12 hours at 40° C. Toluene and water were added to the reaction mixture, and the organic layer was extracted. The organic layer was washed with water and saturated saline solution and dried over anhydrous sodium sulfate. The resulting residue (384 mg) was dissolved in tetrahydrofuran (15 ml), and lithium aluminum hydride (56 mg) was added to the solution at −10° C. After the mixture was stirred for three hours under cooling with ice, sodium sulfate decahydrate was added thereto. After the resultant was filtrated through celite, the filtrate was concentrated to give the residue. The residue was purified by a reversed-phase column chromatography (water-methanol) to obtain (1S)-1,5-anhydro-1-[5-(1-benzothien-2-ylmethyl)-2-(hydroxymethyl)phenyl]-D-glucitol (90 mg).

Example 182

Twenty percents of hydrochloric acid-methanol (three drops) and 5% palladium-carbon (0.1 g) were added to a solution of (1H-indene-2-yl) [3-(2,3,4,6-tetra-0-benzyl-β-D-glucopyranosyl)phenyl]methanone (0.84 g) in methanol (10 ml), and the resultant was stirred for 18 hours in a hydrogen atmosphere. The reaction mixture was filtrated, and the solvent was evaporated from the filtrate under reduced pressure to give the residue, and the resulting residue was purified by silica gel column chromatography (chloroform-methanol) to obtain (1S)-1,5-anhydro-1-[3-[(2,3-dihydro-1H-indene-2-yl)methyl]phenyl]-D-glucitol (16 mg).

The compounds in Examples 183 and 184 were obtained in a manner similar to that of Example 182.

Example 185

Sodium hydride (42 mg) was added to a solution of pyrrole (64 mg) in dimethylformamide (10 ml) under cooling with ice, and the mixture was stirred for half an hour at room temperature. After the mixture was cooled to −30° C., a solution of (1S)-2,3,4,6-tetra-0-acetyl-1,5-anhydro-1-[3-(bromomethyl)phenyl]-D-glucitol (80 mg) in tetrahydrofuran (2 ml) was added dropwise thereto, and the resultant was stirred for one hour at room temperature. Methanol (10 ml) and sodium methoxide (44 mg) was added thereto, and the resultant was stirred for one hour at the same temperature. After the completion of the reaction, the reaction mixture was concentrated to give the residue. The resulting residue was purified by a reversed-phase column chromatography (water-methanol) to obtain (1S)-1,5-anhydro-1-[3-(1H-pyrrole-1-ylmethyl)-phenyl]-D-glucitol (18 mg).

Example 186

Twenty percents of palladium hydroxide/carbon (130 mg) were added to a suspension of (1S)-1,5-anhydro-2,3,4,6-tetra-0-benzyl-1-[5-(4-ethyl benzyl)-1H-pyrrole-2-yl]-D-glucitol (400 mg) in ethyl acetate-acetic acid (10:1) (11 ml), and the resultant was stirred for one hour in a hydrogen atmosphere (1 atm). The reaction mixture was filtrated through celite, and the filtrate was concentrated to give the residue. The resulting residue was purified by silica gel column chromatography (chloroform-methanol) to obtain (1S)-1,5-anhydro-1-[5-(4-ethyl benzyl)-1H-pyrrole-2-yl]-D-glucitol (25 mg).

The compound in Example 187 was obtained in a manner similar to that of Example 186.

Example 188

Ten percents of palladium/carbon (450 mg) was added to a solution of (1S)-1,5-anhydro-2,3,4,6-tetra-0-benzyl-1-[1-(4-ethylbenzyl)-1H-pyrrole-2-yl]-D-glucitol (587 mg) in ethyl acetate-methanol-acetic acid (10:2:1) (39 ml), and the resultant was stirred for 22 hours in a hydrogen atmosphere. The reaction mixture was filtrated through celite, and the filtrate was concentrated to give the residue. The resulting residue was purified by silica gel column chromatography (chloroform-methanol) to obtain (1S)-1,5-anhydro-1-[1-(4-ethyl benzyl)-1H-pyrrole-2-yl]-D-glucitol (59 mg).

The structural formulas and physicochemical properties of the compounds of Reference Examples are shown by the following Tables 1-6. The structural formulas and physicochemical properties of the compounds of Examples are shown by the following Tables 7-36.

Incidentally, the symbols in the tables have the following meanings:

Rf.: number of Reference Example, Ex: number of Example, Structure: structural formula, Me: methyl group, Et: ethyl group, Bn: benzyl group, Bu: butyl group, TBDMS: tert-butyldimethylsilyl group, TBDPS: tert-butyldiphenylsilyl group, Ac: Acetyl group, Tf: trifluoromethanesulfonyl group, Data: property data, NMR: nuclear magnetic resonance spectrum (TMS internal standard), MS: mass analysis value Compounds listed in Tables 37 to 39 can be easily prepared in a manner similar to that of Examples and Preparation Examples or by a method with minor modifications which are obvious for persons of ordinary skill in the art. Tables 37 to 39 are given after Tables 1 to 36.

INDUSTRIAL APPLICABILITY

Since C-glycoside derivatives and the salts thereof (the compounds of the present invention) have the effects of inhibiting a $Na^+$-glucose cotransporter and reducing the level of blood glucose, these compounds are useful for treating or preventing diabetes such as insulin-dependent diabetes (type 1 diabetes) and insulin-independent diabetes (type 2 diabetes), insulin-resistant diseases, and obesity, for example, as a medicine, particularly as a $Na^+$-glucose cotransporter inhibitor.

The significant effects of inhibiting a $Na^+$-glucose cotransporter and reducing the blood glucose of the compound of the present invention have been confirmed by the following pharmacological tests (Test Examples 1 and 2).

Test Example 1

Inhibition of Human $Na^+$-Glucose Cotransporter (Human SGLT2) Activity (1) Preparation of Human SGLT 2 Expression Vector First, single-strand cDNA was reversely transcripted from total RNA originating from the human kidney (manufactured by BD Biosciences Clontech) using a Superscript II (manufactured by Invitrogen Corporation) and a random hexamer. Second, using the cDNA as a template, a DNA fragment encoding a human SGLT2 (Wells, R. G. et al., Am. J. Physiol., 1992, 263(3) F459) was amplified by the PCR reaction using Pyrobest DNA polymerase (manufactured by Takara Bio Inc.). That is, a Hind III site and an EcoRI site were inserted into the 5' side and the 3' side of the DNA fragment, respectively by using primers.

The amplified fragment was cloned into a pCR2.1-Topo vector using a Topo TA Cloning Kit (manufactured by Invitrogen Corporation) and the cloned vector was transfected into a competent cell of *Escherichia coli* JM109. Ampicillin-resistant clones were cultured in a LB medium containing ampicillin (100 mg/l). A plasmid was purified from the cultured *Escherichia coli* using the method of Hanahan (see Maniatis et al., "Molecular Cloning"). A DNA fragment for encoding a human SGLT2 was obtained by the Hind III/EcoRI digestion of the plasmid and ligated and cloned to the same site of the expression vector pcDNA 3.1 (manufactured by Invitrogen Corporation) using a DNA ligase (manufactured by Roche Diagnostics). The ligated clone was transfected into a competent cell of *Escherichia coli* JM109 in the same manner as described above and cultured in a LB medium containing ampicillin, and a human SGLT2 expression vector was obtained using the method of Hanahan.

(2) Preparation of Human SGLT2 Expressed Cells

The human SGLT2 expression vector was transfected into a CHO-K1 cell using Lipofectamine2000 (manufactured by Invitrogen Corporation). The cell was cultured in a Ham's F12 medium (manufactured by Nissui Pharmaceutical Co., Ltd.) containing penicillin (50 IU/ml, manufactured by Dainippon Pharmaceutical Co., Ltd.), streptomycin (50 µg/ml, manufactured by Dainippon Pharmaceutical Co., Ltd.), Geneticin (40 µg/ml, manufactured by Invitrogen Corporation), and 10% fetal bovine serum in the presence of 5% $CO_2$ at 37° C. for two weeks, and Geneticin-resistant clones were obtained. A cell which stably expresses the human SGLT2, which exhibits sodium-dependent intake of methyl-α-D-glucopyranoside, was obtained (See the following paragraphs for the method for measuring the methyl-α-D-glucopyranoside intake).

(3) Inhibition of methyl-α-D-glucopyranoside Intake

After removing the medium of a CHO cell which stably expresses the human SGLT2, a pretreatment buffer solution (buffer solution of pH 7.4 containing choline chloride (140 mM), potassium chloride (2 mM), calcium chloride (1 mM), magnesium chloride (1 mM), 2-[4-(2-hydroxyethyl)1-piperazinyl]ethanesulfonic acid (10 mM), and tris(hydroxymethyl)aminomethane (5 mM)) was added in the amount of 100 µl per well, and incubated at 37° C. for 20 minutes.

11 µl of methyl-α-D-(U-14C)glucopyranoside (manufactured by Amersham Pharmacia Biotech) was mixed with 1,000 µl of a buffer solution for intake containing a test compound (buffer solution of pH 7.4 containing sodium chloride (140 mM), potassium chloride (2 mM), calcium chloride (1 mM), magnesium chloride (1 mM), methyl-α-D-glucopyranoside (50 µM), 2-[4-(2-hydroxy ethyl)1-piperazinyl] ethanesulfonic acid (10 mM), and tris(hydroxymethyl)aminomethane (5 mM)) to prepare a buffer solution for intake. A buffer solution for intake without a test compound was prepared for a control group. A buffer solution for basal intake without a test compound containing choline chloride (140 mM) instead of sodium chloride for measuring the basal intake was prepared as well.

After removing the pretreatment buffer solution, the buffer solution for intake was added (25 µl per well) and incubated at 37° C. for two hours. After removing the buffer solution for intake, a buffer solution for washing (buffer solution of pH 7.4 containing choline chloride (140 mM), potassium chloride (2 mM), calcium chloride (1 mM), magnesium chloride (1 mM), methyl-α-D-glucopyranoside (10 mM), 2-[4-(2-hydroxyethyl)-1-piperazinyl]ethanesulfonic acid (10 mM), and tris(hydroxymethyl) aminomethane (5 mM)) was added (200 µl per one well). The mixture was immediately removed. This washing operation was carried out once more. 0.5% Sodium lauryl sulfate was added (25 µl per well) to solubilize the cells. Seventy five µl of Microscint 40 (manufactured by Perkin Elmer, Inc.) was added to the solubilized cell and the radiation activity was measured using a microscintillation counter Top-Count (manufactured by Perkin Elmer, Inc.). The value obtained by subtracting the basal intake amount from the intake amount of the control group was defined as 100%. The concentration for 50% inhibition of the above value ($IC_{50}$ value) was calculated from a concentration-inhibition curve using the least squares method. As a result, the compound of the present invention exhibited a strong effect of inhibiting a $Na^+$-glucose cotransporter activity. The $IC_{50}$ values of typical compounds of the present invention are shown in Table 40.

TABLE 40

| Compound | $IC_{50}$ (nM) |
|---|---|
| Example 117 | 13 |
| Example 134 | 14 |
| Example 141 | 3.8 |
| Example 142 | 21 |
| Example 150 | 6.5 |
| Example 174 | 6.6 |

Test Example 2

Hypoglycemic Activity Confirmation Test

Fed KK-$A^y$ mice (CLEA Japan, Inc., male) were used. The test compound was suspended in 0.5% methylcellulose solution to a concentration of 1 mg/10 ml. The weight of each mouse was measured. The test compound suspension was orally administered to the mice at a dose of 10 ml/kg. Only 0.5% methylcellulose solution was administered to the mice of a control group. Each group consisted of six mice. Blood was collected from the tail vein immediately before administering the compound and one, two, four, and eight hours after administering the compound. The blood glucose value was measured using a glucose CII Test Wako (manufactured by Wako Pure Chemical Industries, Ltd.). The intensity of hypoglycemic activity was determined by calculating the area under the blood glucose value-time curve (AUC) using a trapezoidal method from the glucose value of 0-8 hours after administering the compound and calculating the rate (%) of the decrease in the AUC of the drug-administered group from that of the control group.

As a result, the compound of the present invention exhibited a strong hypoglycemic activity. The hypoglycemic activity of typical compounds of the present invention are shown in Table 41.

TABLE 41

| Compound | Hypoglycemic activity (%) |
|---|---|
| Example 134 | 39 |
| Example 141 | 34 |

As a result of Test Examples 1 and 2, compounds of the present invention showed a remarkable effect by inhibiting a $Na^+$-glucose cotransporter activity and a strong hypoglycemic activity. Therefore, it is expected that compounds of the present invention can serve as an antidiabetic medicine having the same or higher effect in comparison with the conventional antidiabetic medicines.

The pharmaceutical composition containing one or more of the compounds of the present invention and the pharmaceutically acceptable salts thereof is prepared as a tablet, powder, fine granule, granule, capsule, pill, liquid, injection, suppository, ointment, adhesive, or the like using a carrier, vehicle, or other additives commonly used for preparation and is orally or parenterally administered.

The amount of the compound of the present invention to be clinically administered to the human body is appropriately determined, taking the symptoms, weight, age, sex, and the like of a patient to which the compound is administered into consideration, in the range of 0.1-500 mg per day for oral administration or in the range of 0.01-100 mg per day for parenteral administration, once or several times a day. Since the amount to be administered varies, depending upon various conditions, it may be sufficient to administer the compound at a smaller amount than the above-described amount.

As a solid composition for oral administration of the compound of the present invention, a tablet, powder, granule, or the like is used. In such a solid composition, one or more active substances are mixed with at least one inert diluent such as lactose, mannitol, glucose, hydroxypropylcellulose, microcrystal cellulose, starch, polyvinylpyrrolidone, or magnesium aluminometasilicate. The composition may contain additives other than the inert diluent such as a lubricant such as magnesium stearate, a disintegrator such as carboxymethylcellulose calcium, a stabilizer such as sucrose, a solubilizer such as glutamic acid and aspartic acid, an adjuvant for solubilization, and the like by a conventional method. The tablet or pill may be optionally coated with a film of glucose or a stomach-soluble or intestines-soluble substance such as sucrose, gelatin, hydroxypropylcellulose, or hydroxypropylmethylcellulose phthalate.

The liquid composition for oral administration includes pharmaceutically acceptable preparations such as an emulsion preparation, solution preparation, suspension preparation, syrup preparation, elixir preparation, and the like and contains a commonly used inert diluent such as purified water and ethyl alcohol. The composition may contain, in addition to the diluent, adjuvants such as a solubilizer, humectant, and suspending agent, sweetener, flavorer, perfume, and preservative.

The injection for parenteral administration includes a sterilized aqueous or nonaqueous solution, suspension, and emulsion. Examples of the diluent for the aqueous solution or suspension include distilled water and a physiological saline solution for injection. Examples of the diluent for the nonaqueous solution or suspension include propylene glycol, polyethylene glycol, and vegetable oils such as olive oil; alcohols such as ethyl alcohol; and Polysolvate 80 (trade name).

Such a composition may further contain additives such as an isotonizing agent, preservative, humectant, emulsifier, dispersant, stabilizer (e.g. lactose), solubilizer and adjuvant for solubilization. These compounds are sterilized by filtering through a bacteria-retaining filter and adding a disinfectant or irradiating, for example. These compounds may be used by producing a sterilized solid composition and dissolving the composition in a sterilized water or injection solvent before using.

TABLE 1

| Rf. | STRUCTURE | DATA |
|---|---|---|
| 1 | 4-bromo-2,5-bis(methoxymethoxy)benzaldehyde | FAB-MS(m/z); 307[M + H]$^+$ |
| 2 | 4'-bromo-[1,1'-biphenyl]-2-carbaldehyde | EI-MS(m/z); 261[M]$^+$ |
| 3 | (3-bromo-5-fluorobenzyl)oxy-TBDPS | FAB-MS(m/z); 443[M]$^+$ |
| 4 | (3-bromo-4-chlorobenzyl)oxy-TBDPS | FAB-MS(m/z); 459[M]$^+$ |
| 5 | (4-bromo-2-chloro-5-(methoxymethoxy)benzyl)oxy-TBDPS | EI-MS(m/z); 518[M − H]$^-$ |
| 6 | (5-(benzyloxy)-4-bromo-2-fluorobenzyl)oxy-TBDPS | $^1$H-NMR(CDCl$_3$); 1.09(9H, s), 4.70(2H, s), 5.11(2H, s), 6.61(1H, d), 7.32-7.48(11H, m), 7.63-7.70(5H, m) |

TABLE 1-continued

| Rf. | STRUCTURE | DATA |
|---|---|---|
| 7 | (structure) | FAB-MS(m/z); 439[M + H]⁺ |
| 8 | (structure) | FAB-MS(m/z); 502[M + H]⁺ |
| 9 | (structure) | $^1$H-NMR(CDCl$_3$); 2.29(3H, s), 3.54-3.90(6H, m), 3.98(1H, d), 4.40-4.68(4H, m), 4.75-5.05(6H, m), 6.75-7.43(28H, m) |

TABLE 2

| Rf. | STRUCTURE | DATA |
|---|---|---|
| 10 | (structure) | FAB-MS(m/z); 648[M + H]⁺ |
| 11 | (structure) | FAB-MS(m/z); 665[M + H]⁺ |
| 12 | (structure) | EI-MS(m/z); 748[M + Na]⁺ |
| 13 | (structure) | EI-MS(m/z); 777[M + Na]⁺ |
| 14 | (structure) | FAB-MS(m/z); 481[M + H]⁺ |
| 15 | (structure) | FAB-MS(m/z); 559[M + H]⁺ |
| 16 | (structure) | ES-MS(m/z); 666[M + Na]⁺ |
| 17 | (structure) | FAB-MS(m/z); 711[M + H]⁺ |

TABLE 3

| Rf. | STRUCTURE | DATA |
|---|---|---|
| 18 | (morpholine-substituted benzaldehyde with tetra-O-benzyl pyranose) | ES-MS(m/z); 714[M + H]+ |
| 19 | (3-fluoro-5-formyl phenyl with tetra-O-benzyl pyranose) | ES-MS(m/z); 669[M + Na]+ |
| 20 | (2-chloro-5-formyl phenyl with tetra-O-benzyl pyranose) | ES-MS(m/z); 685[M + Na]+ |
| 21 | (4-MOM-O, 5-chloro-formyl phenyl with tetra-O-benzyl pyranose) | ES-MS(m/z); 746[M + Na]+ |
| 22 | (4-BnO, 5-fluoro-formyl phenyl with tetra-O-benzyl pyranose) | FAB-MS(m/z); 753[M + H]+ |
| 23 | (3-(N-methoxy-N-methylcarbamoyl)phenyl with tetra-O-benzyl pyranose) | 1H-NMR(CDCl3); 3.33(3H, s), 3.47(3H, s), 3.61-3.84(7H, m), 4.28-4.96(8H, m), 6.89-7.39(20H, m), 7.42(1H, t), 7.55(1H, d), 7.66(1H, d), 7.81(1H, s) |

TABLE 3-continued

| Rf. | STRUCTURE | DATA |
|---|---|---|
| 24 | (structure) | ES-MS(m/z); 749[M + H]⁺ |
| 25 | (structure) | FAB-MS(m/z); 671[M + H]⁺ |

TABLE 4

| Rf. | STRUCTURE | DATA |
|---|---|---|
| 26 | (structure) | $^1$H-NMR(CDCl$_3$); 1.27(3H, t), 2.76(2H, dd), 4.04(2H, s), 6.60(2H, d), 7.16-7.39(4H, m) |
| 27 | (structure) | $^1$H-NMR(CDCl$_3$); 2.16(3H, s), 4.04(2H, s), 6.82(1H, d), 7.07(1H, d), 7.12-7.34(4H, s) |
| 28 | (structure) | FAB-MS(m/z); 203[M − H]⁻ |
| 29 | (structure) | $^1$H-NMR(CDCl$_3$); 2.36(3H, s), 4.18(2H, s), 7.14-7.18(2H, m), 7.25-7.40(4H, m), 7.65(1H, d), 7.74(1H, d) |
| 30 | (structure) | $^1$H-NMR(CDCl$_3$); 4.16(2H, s), 7.13(1H, d), 7.15-7.19(2H, m), 7.33-7.38(3H, m), 7.42(1H, s), 7.67(1H, m), 7.87(1H, m) |
| 31 | (structure) | EI-MS(m/z); 364[M + H]⁺ |
| 32 | (structure) | EI-MS(m/z); 334[M + H]⁺ |

TABLE 4-continued

| Rf. | STRUCTURE | DATA |
| --- | --- | --- |
| 33 | (2-bromo-4,5-bis(methoxymethoxy)phenyl)methyl-benzothiophene | FAB-MS(m/z); 423[M + H]+ |
| 34 | (2-bromo-4,5-dimethoxyphenyl)methyl-benzothiophene | EI-MS(m/z); 364[M + H]+ |
| 35 | (3-bromo-biphenyl)methyl-benzothiophene | EI-MS(m/z); 380[M + H]+ |

TABLE 5

| Rf. | STRUCTURE | DATA |
| --- | --- | --- |
| 36 | thiophen-3-ylmethyl-benzothiophene | EI-MS; 230[M]+ |
| 37 | (5-bromo-2-chlorophenyl)(OTBDMS)methyl-benzothiophene | FAB-MS(m/z); 467[M]+ |
| 38 | (5-bromo-2-fluorophenyl)(OTBDMS)methyl-benzothiophene | FAB-MS(m/z); 451[M]+ |
| 39 | (3-bromo-4-fluorophenyl)(OTBDMS)methyl-benzothiophene | FAB-MS(m/z); 451[M]+ |

TABLE 5-continued

| Rf. | STRUCTURE | DATA |
|---|---|---|
| 40 | 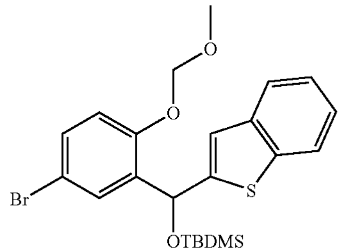 | FAB-MS(m/z); 493[M]+ |
| 41 | 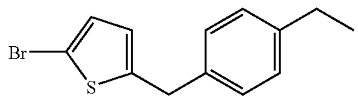 | $^1$H-NMR(CDCl$_3$); 1.22(3H, t), 2.63(2H, q), 4.03(2H, s), 6.55(1H, d), 6.85(1H, d), 7.14(4H, s) |
| 42 | 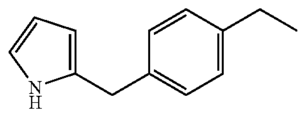 | $^1$H-NMR(CDCl$_3$); 1.22(3H, t), 2.62(2H, q), 3.44(2H, s), 5.96-6.01(1H, m), 6.14(1H, dd), 6.65(1H, dd), 7.00-7.28(4H, m) |
| 43 | 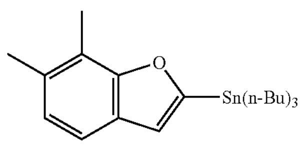 | $^1$H-NMR(CDCl$_3$); 0.90(9H, m), 1.12-1.39(12H, m), 1.60(6H, m), 2.37(3H, s), 2.44(3H, s), 6.83(1H, s), 6.98(1H, d), 7.26(1H, m) |
| 44 | 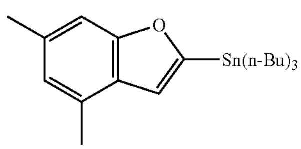 | $^1$H-NMR(CDCl$_3$); 0.88(9H, m), 1.12-1.38(14H, m), 1.58(4H, m), 2.42(3H, s), 2.47(3H, s), 6.81(1H, s), 6.84(1H, s), 7.14(1H, s) |
| 45 | 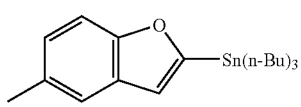 | $^1$H-NMR(CDCl$_3$); 0.91(9H, m), 1.08-1.62(18H, m), 2.43(3H, s), 6.81(1H, s), 7.02(1H, d), 7.32(1H, s), 7.36(1H, d) |

TABLE 6

| Rf. | STRUCTURE | DATA |
|---|---|---|
| 46 | 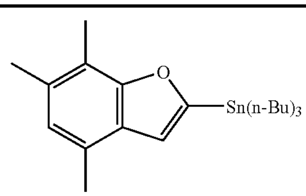 | $^1$H-NMR(CDCl$_3$); 0.90(9H, m), 1.14(6H, m), 1.36(6H, m), 1.61(6H, m), 2.34(3H, s), 2.40(3H, s), 2.44(3H, s), 6.80(1H, s), 6.83(1H, s) |
| 47 | 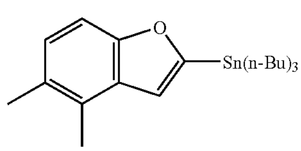 | $^1$H-NMR(CDCl$_3$); 0.90(9H, m), 1.14(6H, m), 1.35(6H, m), 1.60(6H, m), 2.34(3H, s), 2.42(3H, s), 6.87(1H, s), 7.00(1H, d), 7.23(1H, d) |
| 48 | 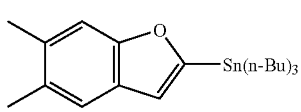 | $^1$H-NMR(CDCl$_3$); 0.89(9H, m), 1.12(6H, m), 1.33(6H, m), 1.57(6H, m), 2.32(3H, s), 2.35(3H, s), 6.78(1H, d), 7.28(2H, s) |
| 49 | 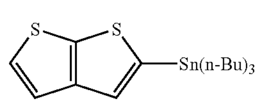 | ES-MS(m/z); 431[M + H]+ |

TABLE 6-continued

| Rf. | STRUCTURE | DATA |
|---|---|---|
| 50 | 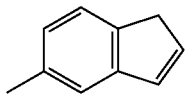 | $^1$H-NMR(CDCl$_3$); 2.39(3H, s), 3.35(2H, s), 6.52-6.54(1H, m), 6.82-6.84(1H, m), 6.99-7.35(2H, ABq), 7.22(1H, s) |
| 51 | 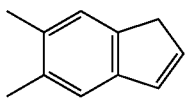 | $^1$H-NMR(CDCl$_3$); 2.37(3H, s), 3.55(2H, s), 6.87(1H, s), 6.96-7.25(2H, ABq), 7.11(1H, s) |
| 52 | 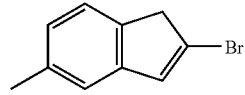 | $^1$H-NMR(CDCl$_3$); 2.29(6H, s), 3.33(2H, s), 6.45(1H, d), 6.80(1H, d), 7.18(1H, s), 7.24(1H, s) |
| 53 | 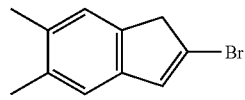 | $^1$H-NMR(CDCl$_3$); 2.26(3H, s), 2.27(3H, s), 3.53(2H, s), 6.85(1H, s), 7.08(1H, s), 7.14(1H, s) |
| 54 | 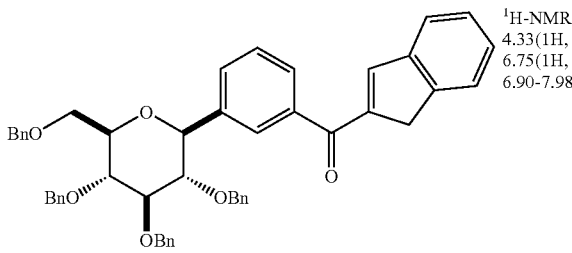 | $^1$H-NMR(CDCl$_3$); 3.52-4.06(6H, m), 4.33(1H, d), 4.45-4.95(10H, m), 6.75(1H, d), 7.67-7.86(4H, m), 6.90-7.98(27H, m), 8.23(1H, s) |
| 55 | 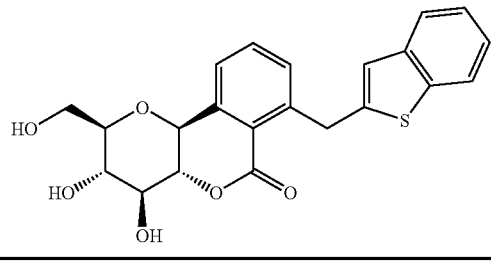 | FAB-MS(m/z); 413[M + H]$^+$ |

TABLE 7

| Ex. | STRUCTURE | DATA |
|---|---|---|
| 1 | 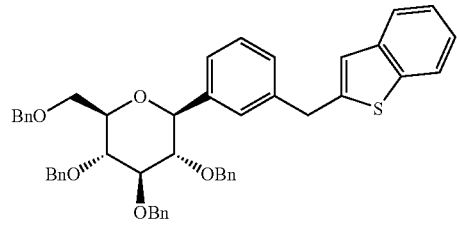 | $^1$H-NMR(CDCl$_3$); 3.51(1H, m), 3.59(1H, m), 3.73-3.81(5H, m), 4.21-4.24(3H, m), 4.35(1H, d), 4.50-4.65(3H, m), 4.82-4.94(3H, m), 6.87-6.89(2H, m), 6.97(1H, s), 7.13-7.40(24H, m), 7.66(1H, d), 7.68(1H, d)<br>FAB-MS(m/z); 746[M − H]$^-$ |
| 2 | 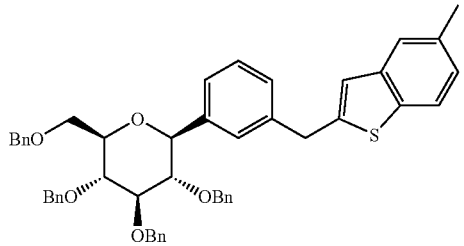 | $^1$H-NMR(CDCl$_3$); 2.41(3H, s), 3.48-3.59(2H, m), 3.76-3.82(5H, m), 4.20(2H, s), 4.22(1H, d), 4.34(1H, d), 4.54(1H, d), 4.62-4.66(2H, m), 4.86(1H, d), 4.87(1H, d), 4.94(1H, d), 6.87-6.89(3H, m), 7.04-7.40(24H, m), 7.55(1H, d)<br>FAB-MS(m/z); 759[M − H]$^-$ |

TABLE 7-continued

| Ex. | STRUCTURE | DATA |
|---|---|---|
| 3 | (structure: 2,3,4,6-tetra-O-benzyl glucopyranosyl attached to phenyl-CH2-benzothiophene with 5-Cl) | $^1$H-NMR(CDCl$_3$); 7.52-7.58(2H, m), 7.11-7.40(23H, m), 6.85-6.90(3H, m), 4.84-4.94(3H, m), 4.51-4.67(3H, m), 4.36(1H, d), 4.24(1H, d), 4.19(2H, s), 3.72-3.82(5H, m), 3.48-3.62(2H, m) FAB-MS(m/z); 781[M]$^+$ |
| 4 | (structure: 2,3,4,6-tetra-O-benzyl glucopyranosyl attached to phenyl-CH2-benzothiophene with 5-F) | $^1$H-NMR(CDCl$_3$); 3.48-3.60(2H, m), 3.76-3.82(5H, m), 4.20(2H, s), 4.24(1H, d), 4.36(1H, d), 4.54(1H, d), 4.61-4.85(2H, m), 4.86(1H, d), 4.88(1H, d), 4.93(1H, d), 6.87-6.91(3H, m), 6.94-7.01(1H, m), 7.13-7.39(23H, m), 7.56(1H, dd) FAB-MS(m/z); 763[M − H]$^-$ |
| 5 | (structure: 2,3,4,6-tetra-O-benzyl glucopyranosyl attached to phenyl-CH2-(3-methyl)benzothiophene with F) | $^1$H-NMR(CDCl$_3$); 2.29(3H, s), 3.47-3.59(2H, m), 3.73-3.82(5H, m), 4.17(2H, s), 4.22(1H, d), 4.34(1H, d), 4.53(1H, d), 4.63(2H, d), 4.86(1H, d), 4.87(1H, d), 4.92(1H, d), 6.87-6.89(2H, m), 6.97-7.03(1H, m), 7.11-7.36(23H, m), 7.55(1H, dd) ES-MS(m/z); 801[M + Na]$^+$ |

TABLE 8

| Ex. | STRUCTURE | DATA |
|---|---|---|
| 6 | (structure: 2,3,4,6-tetra-O-benzyl glucopyranosyl attached to phenyl-CH2-(3-methyl)benzothiophene with Cl) | $^1$H-NMR(CDCl$_3$); 2.28(3H, s), 3.47-3.58(2H, m), 3.73-3.82(5H, m), 4.18(2H, s), 4.22(1H, d), 4.34(1H, d), 4.53(1H, d), 4.63(2H, d), 4.86(1H, d), 4.87(1H, d), 4.92(1H, d), 6.86-6.89(2H, m), 7.11-7.36(23H, m), 7.53-7.56(2H, m) ES-MS(m/z); 817[M + Na]$^+$ |
| 7 | (structure: 2,3,4,6-tetra-O-benzyl glucopyranosyl attached to phenyl-CH2-benzothiophene with t-Bu) | $^1$H-NMR(CDCl$_3$); 1.35(9H, s), 3.49-3.59(2H, m), 3.76-3.82(5H, m), 4.20(2H, s), 4.23(1H, d), 4.34(1H, d), 4.56(1H, d), 4.63(1H, d), 4.64(1H, d), 4.86(1H, d), 4.87(1H, d), 4.94(1H, d), 6.86-6.88(2H, m), 6.94(1H, brs), 7.08-7.36(22H, m), 7.40(1H, brs), 7.60-7.62(2H, m) ES-MS(m/z); 825[M + Na]$^+$ |

TABLE 8-continued

| Ex. | STRUCTURE | DATA |
|---|---|---|
| 8 | 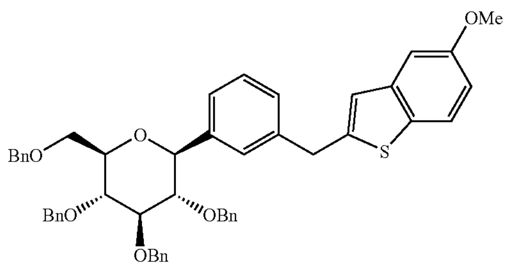 | ¹H-NMR(CDCl₃); 3.49-3.59(2H, m), 3.77-3.80(5H, m), 3.81(3H, s), 4.20(2H, s), 4.23(1H, d), 4.35(1H, d), 4.54(1H, d), 4.62-4.66(2H, m), 4.86(1H, d), 4.88(1H, d), 4.93(1H, d), 6.86-6.90(3H, m), 7.05(1H, d), 7.10-7.36(22H, m), 7.40(1H, brs), 7.53(1H, d) FAB-MS(m/z); 777[M + H]⁺ |
| 9 | 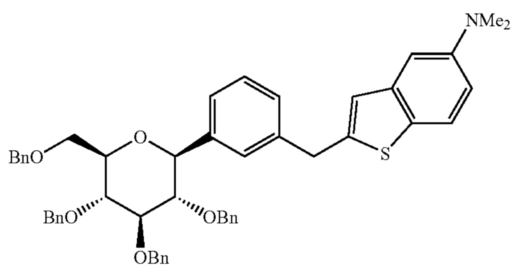 | ¹H-NMR(CDCl₃); 2.93(6H, s), 3.49-3.59(2H, m), 3.73-3.82(5H, m), 4.18(2H, s), 4.23(1H, d), 4.34(1H, d), 4.55(1H, d), 4.63(1H, d), 4.64(1H, d), 4.86(1H, d), 4.87(1H, d), 4.93(1H, d), 6.81-6.91(5H, m), 7.11-7.35(21H, m), 7.40(1H, brs), 7.49(1H, d) ES-MS(m/z); 790[M + H]⁺ |
| 10 | 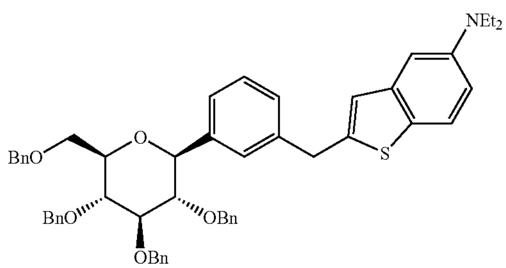 | ¹H-NMR(CDCl₃); 1.14(6H, t), 3.34(4H, q), 3.49-3.59(2H, m), 3.73-3.82(5H, m), 4.17(2H, s), 4.22(1H, d), 4.33(1H, d), 4.53(1H, d), 4.63(1H, d), 4.64(1H, d), 4.86(1H, d), 4.87(1H, d), 4.94(1H, d), 6.76(1H, dd), 6.82(3H, m), 7.10-7.35(21H, m), 7.40(1H, brs), 7.47(1H, d) FAB-MS(m/z); 818[M + H]⁺ |
| 11 | 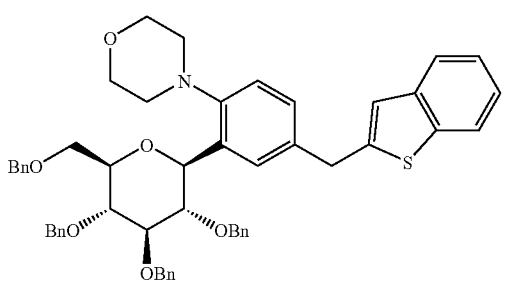 | ¹H-NMR(CDCl₃); 2.92(4H, brs), 3.60(1H, m), 3.71-3.76(8H, m), 3.98(1H, m), 4.17-4.24(2H, m), 4.39-4.59(5H, m), 4.86-4.94(4H, m), 6.70-6.72(2H, m), 6.94(1H, s), 7.08-7.30(23H, m), 7.46(2H, m), 7.56-7.59(1H, m) ES-MS(m/z); 832[M + H]⁺ |

TABLE 9

| Ex. | STRUCTURE | DATA |
|---|---|---|
| 12 | 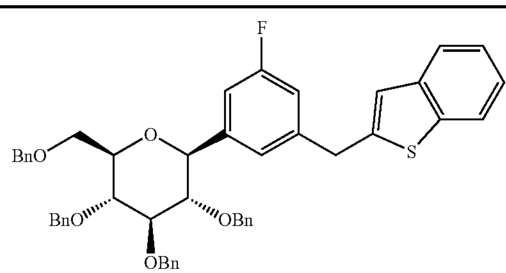 | ¹H-NMR(CDCl₃); 3.40-3.63(2H, m), 3.70-3.90(5H, m), 4.15-4.25(3H, m), 4.42(1H, d), 4.50-4.66(3H, m), 4.82-4.96(3H, m), 6.88-7.35(26H, m), 7.59-7.65(1H, m), 7.67-7.72(1H, m) ES-MS(m/z); 787[M + Na]⁺ |

TABLE 9-continued

| Ex. | STRUCTURE | DATA |
|---|---|---|
| 13 | 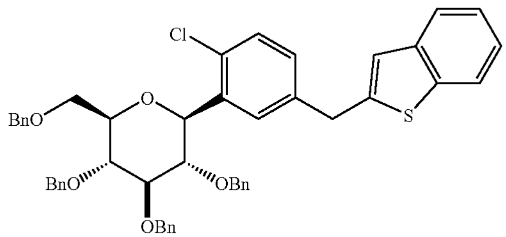 | $^1$H-NMR(CDCl$_3$); 3.61-3.66(2H, m), 3.71-3.88(4H, m), 3.95(1H, d), 4.18(2H, s), 4.37(1H, d), 4.51(1H, d), 4.61(1H, d), 4.63(1H, d), 4.83-4.94(4H, m), 6.93-6.96(3H, m), 7.13-7.31(21H, m), 7.35(1H, d), 7.48(1H, d), 7.58(1H, d), 7.67(1H, d)<br>ES-MS(m/z); 803[M + Na]$^+$ |
| 14 | 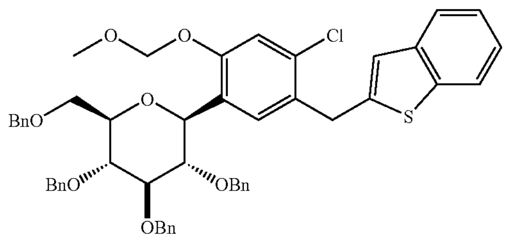 | $^1$H-NMR(CDCl$_3$); 3.33(3H, d), 3.54-3.87(6H, m), 3.98-4.05(1H, m), 4.16-4.34(2H, m), 4.44-4.78(5H, m), 4.82-5.07(5H, m), 6.91-6.98(3H, m), 7.05-7.35(21H, m), 7.41(1H, d), 7.52(1H, d), 7.62(1H)<br>ES-MS(m/z); 841[M]$^+$ |
| 15 | 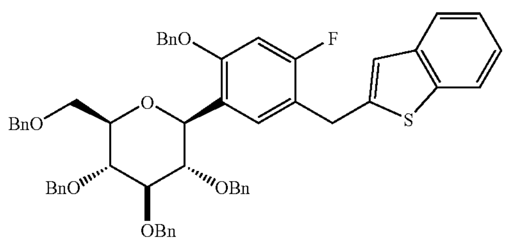 | $^1$H-NMR(CDCl$_3$); 3.56-3.60(1H, m), 3.66-3.83(5H, m), 4.01(1H, d), 4.09-4.24(2H, m), 4.43-4.65(4H, m), 4.75(1H, brs), 4.82-4.99(5H, m), 6.63(1H, d), 6.88(2H, d), 6.93(1H, s), 7.06-7.40(26H, m), 7.56(1H, d), 7.65(1H, d)<br>EI-MS(m/z); 894[M + Na]$^+$ |
| 16 | 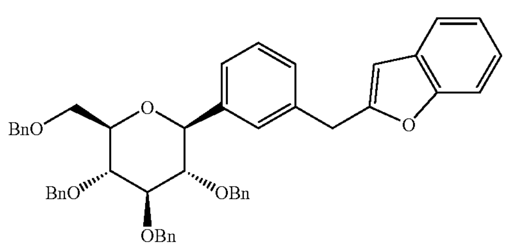 | $^1$H-NMR(CDCl$_3$); 3.48-3.60(2H, m), 3.73-3.81(5H, m), 4.10(2H, s), 4.24(1H, d), 4.37(1H, d), 4.54(1H, d), 4.62-4.66(2H, m), 4.86(1H, d), 4.88(1H, d), 4.94(1H, d), 6.32(1H, d), 6.87-6.90(2H, m), 7.11-7.43(26H, m)<br>ES-MS(m/z); 753[M + Na]$^+$ |
| 17 | 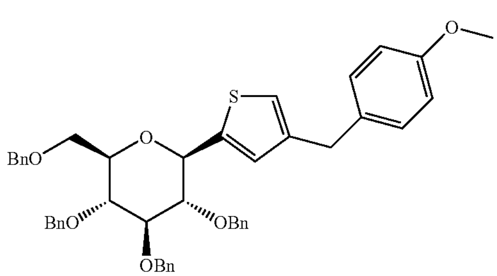 | $^1$H-NMR(CDCl$_3$); 3.47-4.07(12H, m), 4.42-4.70(5H, m), 4.80-4.95(3H, m), 7.75-7.38(26H, m)<br>EI-MS(m/z); 726[M]$^+$ |

TABLE 10

| Ex. | STRUCTURE | DATA |
|---|---|---|
| 18 | 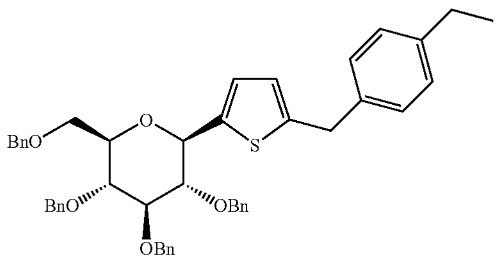 | ¹H-NMR (CDCl₃); 1.21 (3H, t), 2.62 (5H, q), 3.49-4.13 (7H, m), 4.10 (2H, s), 4.43-4.95 (8H, m), 6.69-7.34 (26H, m) ES-MS (m/z); 747 [M + Na]⁺ |
| 19 | 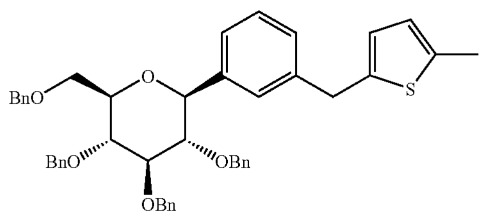 | ¹H-NMR (CDCl₃); 2.36 (3H, s), 3.51-3.82 (7H, m), 4.06 (2H, s), 4.23 (1H, d), 4.35 (1H, d), 4.54-4.96 (6H, m), 6.51-7.33 (26H, m) ES-MS (m/z); 728 [M + NH₄]⁺ |
| 20 | 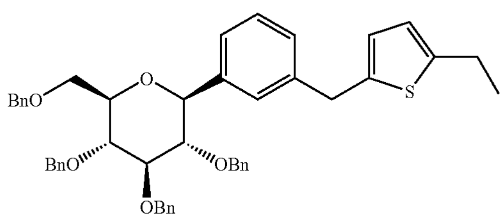 | ¹H-NMR (CDCl₃); 1.21 (3H, t), 2.70 (2H, dd), 3.49-3.82 (7H, m), 4.07 (2H, s), 4.23 (1H, d), 4.35-4.95 (7H, m), 6.53 (2H, dd), 6.89-7.36 (24H, m) ES-MS (m/z); 742 [M + NH₄]⁺ |
| 21 | 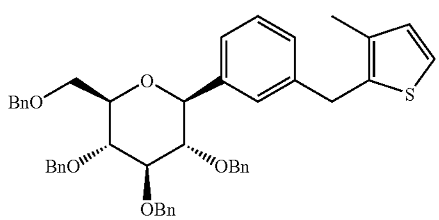 | ¹H-NMR (CDCl₃); 2.14 (3H, s), 3.48-3.81 (7H, m), 4.06 (2H, s), 4.20-4.96 (8H, m), 6.77-7.36 (26H, m) ES-MS (m/z); 728 [M + NH₄]⁺ |
| 22 | 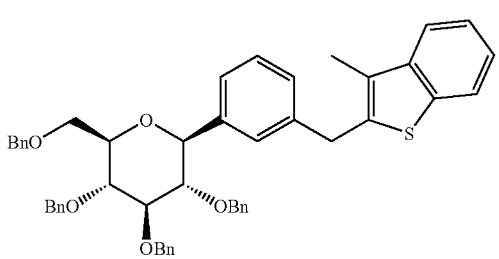 | ¹H-NMR (CDCl₃); 7.67 (1H, d), 7.61 (1H, d), 7.11-7.38 (24H, m), 6.89 (2H, d), 4.84-4.94 (3H, m), 4.63 (2H, d), 4.54 (1H, d), 4.33 (1H, d), 4.22 (1H, d), 4.19 (2H, s), 3.72-3.82 (5H, m), 3.48-3.62 (2H, m), 2.34 (3H, s) FAB-MS (m/z); 760 [M]⁺ |
| 23 | 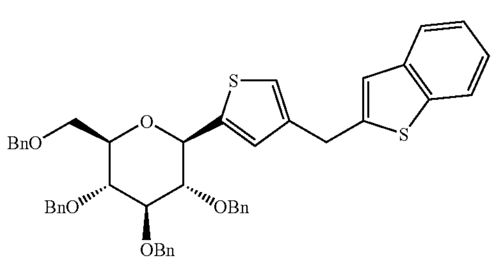 | ¹H-NMR (CDCl₃); 3.49-3.77 (6H, m), 4.05-4.22 (3H, m), 4.40-5.00 (8H, m), 6.85-7.74 (27H, m) FAB-MS (m/z); 751 [M + H]⁻ |

TABLE 10-continued

| Ex. | STRUCTURE | DATA |
|---|---|---|
| 24 | 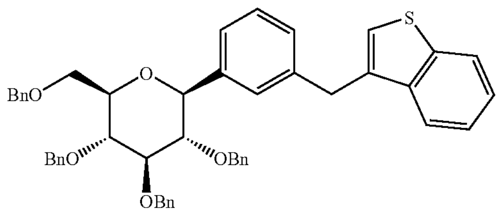 | ¹H-NMR (CDCl₃); 7.83 (1H, brd), 7.65 (1H, dd), 7.15-7.40 (24H, m), 6.93 (1H, s), 6.89 (2H, dd), 4.84-4.94 (3H, m), 4.63 (2H, d), 4.53 (1H, d), 4.34 (1H, d), 4.22 (1H, d), 4.19 (2H, s), 3.72-3.82 (5H, m), 3.48-3.62 (2H, m) |

TABLE 11

| Ex. | STRUCTURE | DATA |
|---|---|---|
| 25 | 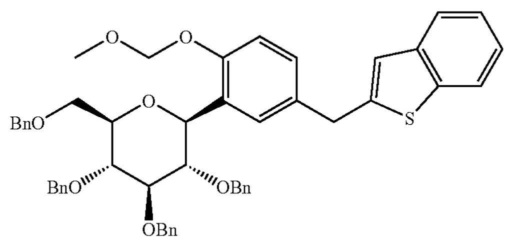 | ¹H-NMR (CDCl₃); 3.35 (3H, s), 3.59-3.61 (1H, m), 3.72-3.82 (5H, m), 3.93 (1H, d), 4.12-4.22 (2H, m), 4.43 (1H, d), 4.51 (1H, d), 4.60 (1H, d), 4.64 (1H, d), 4.73-4.79 (1H, br), 4.87 (1H, d), 4.88 (1H, d), 4.95 (1H, d), 5.03-5.07 (2H, m), 6.85-6.88 (2H, m), 6.96 (1H, s), 7.09-7.31 (22H, m), 7.42 (1H, d), 7.56 (1H, d), 7.66 (1H, d) <br> EI-MS (m/z); 829 [M + Na]⁺ |
| 26 | 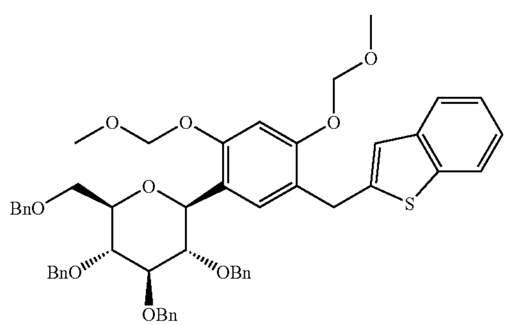 | ¹H-NMR (CDCl₃); 3.37 (3H, s), 3.41 (3H, s), 3.50-3.80 (4H, s), 4.00 (1H, d), 4.10-4.72 (8H, m), 4.84-5.23 (8H, m), 6.73-7.02 (4H, m), 7.07-7.39 (21H, m), 7.51 (1H, d), 7.63 (1H, d) <br> ES-MS (m/z); 889 [M + Na]⁺ |
| 27 | 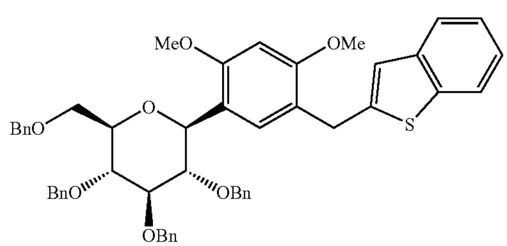 | ¹H-NMR (CDCl₃); 3.17-4.01 (13H, m), 4.10 (1H, d), 4.19 (1H, d), 4.36-5.00 (8H, m), 6.46 (1H, s), 6.85-7.40 (24H, m), 7.52 (1H, d), 7.63 (1H, m) <br> FAB-MS (m/z); 808 [M + H]⁺ |
| 28 | 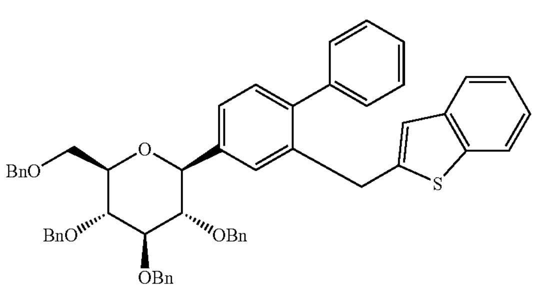 | ¹H-NMR (CDCl₃); 3.45-5.35 (17H, m), 6.70-7.85 (33H, m). <br> ES-MS (m/z); 845 [M + Na]⁺ |

TABLE 11-continued

| Ex. | STRUCTURE | DATA |
| --- | --- | --- |
| 29 | 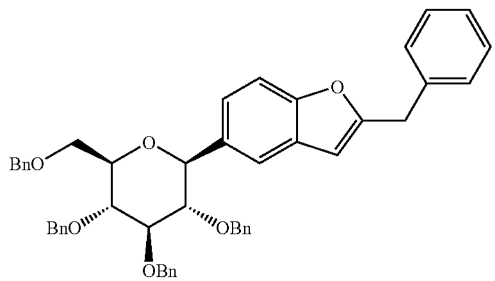 | ¹H-NMR (CDCl₃); 3.50-3.56 (1H, m), 3.60-3.64 (1H, m), 3.71 (1H, d), 3.75-3.84 (4H, m), 4.12 (2H, s), 4.31 (1H, d), 4.32 (1H, d), 4.56 (1H, d), 4.64 (1H, d), 4.65 (1H, d), 4.88 (1H, d), 4.89 (1H, d), 4.96 (1H, d), 6.36 (1H, s), 6.84-6.87 (2H, m), 7.10-7.40 (25H, m), 7.55 (1H, d) FAB-MS (m/z); 731 [M + H]⁺ |
| 30 | 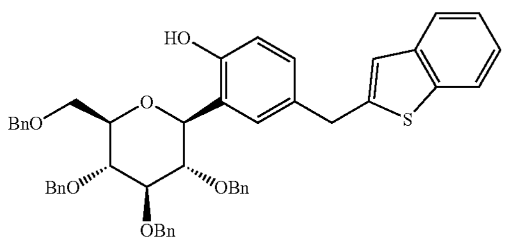 | ¹H-NMR (CDCl₃); 3.54-3.58 (1H, m), 3.67-3.77 (4H, m), 3.83-3.97 (2H, m), 4.05-4.17 (2H, m), 4.37-4.48 (3H, m), 4.52-4.62 (2H, m), 4.83-4.95 (3H, m), 6.90-6.96 (3H, m), 7.08-7.34 (22 H), 7.60 (1H, d), 7.67-7.69 (2H, m) EI-MS (m/z); 785 [M + Na]⁺ |

TABLE 12

| Ex. | STRUCTURE | DATA |
| --- | --- | --- |
| 31 | 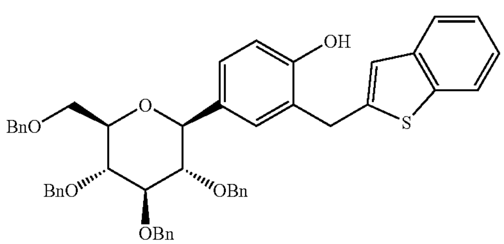 | ¹H-NMR (CDCl₃); 3.44-3.65 (2H, m), 3.70-3.92 (4H, m), 4.13-4.27 (3H, m), 4.37 (1H, d), 4.50-4.67 (3H, m), 4.80-4.96 (3H, m), 6.75-7.05 (3H, m), 7.08-7.35 (22 H), 7.56 (1H, d), 7.67 (1H, d) FAB-MS (m/z); 761[M − H]⁻ |
| 32 | 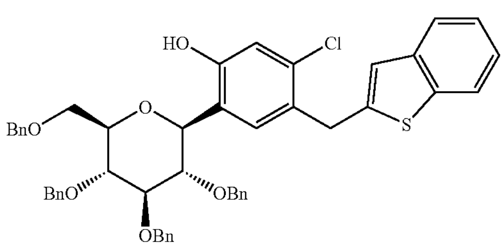 | ¹H-NMR (CDCl₃); 3.51-3.59 (1H, m), 3.63-3.78 (4H, m), 3.84-4.00 (2H, m), 4.04-4.16 (1H, m), 4.26-4.40 (2H, m), 4.43-4.61 (4H, m), 4.82-4.95 (3H, m), 6.90-6.98 (2H, m), 6.99-7.03 (1H, m), 7.05-7.09 (1H, m), 7.12-7.37 (20H, m), 7.56-7.63 (1H, m), 7.66-7.72 (1H, m), 7.80-7.88 (1H, m) FAB-MS (m/z); 795 [M − H]⁻ |
| 33 | 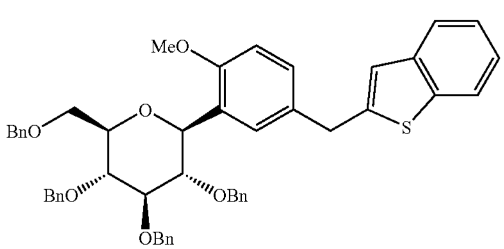 | ¹H-NMR (CDCl₃); 3.58-3.62 (1H, m), 3.71-3.82 (9H, m), 3.92 (1H, d), 4.15-4.19 (2H, m), 4.40 (1H, d), 4.52 (1H, d), 4.61-4.65 (2H, m), 4.84-4.88 (2H, m), 4.94 (1H, d), 6.84-6.89 (3H, m), 6.95 (1H, s), 7.11-7.31 (21H, m), 7.42 (1H, d), 7.56 (1H, d), 7.65 (1H, d). EI-MS (m/z); 799 [M + Na]⁺ |

TABLE 12-continued

| Ex. | STRUCTURE | DATA |
| --- | --- | --- |
| 34 | (structure) | $^1$H-NMR (CDCl$_3$); 3.53-3.82 (9H, m), 3.97-4.20 (1H, m), 4.17-4.32 (2H, m), 4.41-4.66 (4H, m), 4.73 (1H, brs), 4.81-4.95 (3H, m), 6.83-6.94 (4H, m), 7.09-7.32 (20H, m), 7.38-7.43 (1H, m), 7.48-7.55 (1H, m), 7.58-7.64 (1H, m) ES-MS (D/z); 811 [M]$^+$ |
| 35 | (structure) | $^1$H-NMR (CDCl$_3$); 3.38 (3H, s), 3.56-3.62 (2H, m), 3.64-3.81 (7H, m), 3.92 (1H, d), 3.95-4.08 (2H, m), 4.14 (1H, d), 4.19 (1H, d), 4.40 (1H, d), 4.51 (1H, d), 4.62 (1H, d), 4.63 (1H, d), 4.84-4.88 (2H, m), 4.93 (1H, d), 6.84-6.88 (3H, m), 6.96 (1H, s), 7.09-7.31 (21H, m), 7.39 (1H, s), 7.57 (1H, d), 7.66 (1H, d). EI-MS (m/z); 843 [M + Na]$^+$ |
| 36 | (structure) | $^1$H-NMR (CDCl$_3$); 3.40-3.65 (3H, m), 3.70-3.98 (7H, m), 4.05-4.47 (6H, m), 4.50-4.70 (3H, m), 4.80-4.95 (3H, m), 6.80-6.96 (3H, m), 7.06-7.40 (21H, m), 7.55 (1H, d), 7.66 (1H, d). FAB-MS (m/z); 806 [M − H]$^-$ |

TABLE 13

| Ex. | STRUCTURE | DATA |
| --- | --- | --- |
| 37 | (structure) | $^1$H-NMR (CDCl$_3$); 1.40 (9H, s), 3.32-3.38 (2H, m), 3.58-3.61 (1H, m), 3.71-3.83 (6H, m), 3.95-4.03 (2H, m), 4.13 (1H, d), 4.18 (1H, d), 4.45-4.52 (2H, m), 4.56-4.63 (2H, m) 4.84-4.89 (2H, m), 4.97 (1H, d), 5.36-5.44 (1H, d), 6.77 (1H, d), 6.82 (2H, d), 6.98 (1H, s), 7.06-7.32 (21H, m), 7.35 (1H, s), 7.59 (1H, d), 7.67 (1H, d). EI-MS (m/z); 928 [M + Na]$^+$ |
| 38 | (structure) | $^1$H-NMR (CDCl$_3$); 3.61 (1H, m), 3.72 (3H, s), 3.73-3.84 (5H, m), 4.00 (1H, d), 4.15-4.19 (2H, m), 4.41 (1H, d), 4.48-4.55 (3H, m), 4.59-4.66 (2H, m), 4.84-4.96 (4H, m), 6.74 (1H, d), 6.86-6.90 (2H, m), 6.96 (1H, s), 7.08-7.32 (21H, m), 7.41 (1H, s), 7.57 (1H, d), 7.66 (1H, d) FAB-MS (m/z); 836 [M + H]$^+$ |

TABLE 13-continued

| Ex. | STRUCTURE | DATA |
|---|---|---|
| 39 | 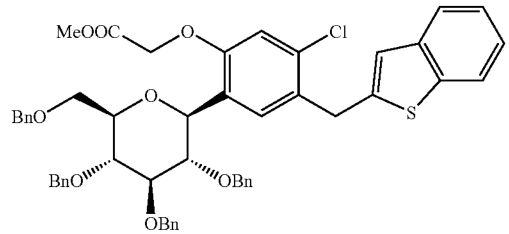 | ¹H-NMR (CDCl₃); 1.28 (3H, t), 3.56-3.62 (1H, m), 3.67-3.84 (5H, m), 4.08 (1H, d), 4.19-4.27 (4H, m), 4.45-4.52 (4H, m), 4.56-4.65 (2H, m), 4.74 (1H, brs), 4.83-4.93 (3H, m), 6.80 (1H, s), 6.88-6.95 (3H, m), 7.08-7.32 (20H, m), 7.40 (1H, s), 7.53-7.67 (1H, m), 7.63-7.67 (1H, m)<br>ES-MS (m/z); 905 [M + Na]⁺ |
| 40 | 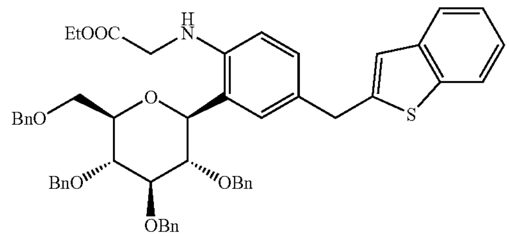 | ¹H-NMR (CDCl₃); 1.25 (3H, t), 3.58-3.87 (8H, m), 4.10 (2H, s), 4.12-4.19 (3H, m), 4.34-4.37 (2H, m), 4.49 (1H, d), 4.55 (1H, d), 4.62 (1H, d), 4.84-4.96 (3H, m), 6.45 (1H, d), 6.90-6.96 (3H, m), 7.08-7.31 (22H, m), 7.60 (1H, d), 7.68 (1H, d)<br>ES-MS (m/z); 848 [M + H]⁺ |
| 41 | 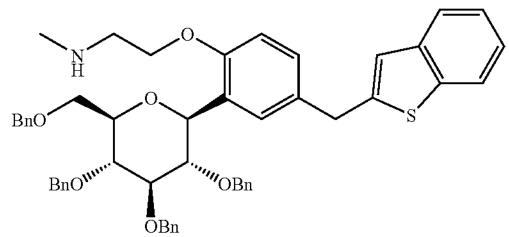 | ¹H-NMR (CDCl₃); 2.40 (3H, s), 2.90 (2H, t), 3.57-3.61 (1H, m), 3.71-3.79 (6H, m), 3.94-4.04 (3H, m), 4.14 (1H, d), 4.19 (1H, d), 4.38 (1H, d), 4.51 (1H, d), 4.58-4.63 (2H, m), 4.86 (1H, d), 4.87 (1H, d), 4.93 (1H, d), 6.83-6.87 (3H, m), 6.96 (1H, s), 7.08-7.31 (21H, m), 7.37 (1H, s), 7.57 (1H, d), 7.66 (1H, d).<br>FAB-MS (m/z); 820 [M + H]⁺ |
| 42 | 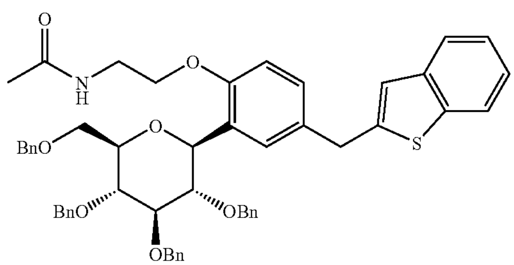 | ¹H-NMR (CDCl₃); 1.70 (3H, s), 3.37-3.50 (2H, m), 3.59-3.63 (1H, m), 3.68-3.83 (7H, m), 3.92 (1H, d), 4.08-4.12 (1H, m), 4.17 (1H, d), 4.22 (1H, d), 4.44 (1H, d), 4.52 (1H, d), 4.59 (1H, d), 4.63 (1H, d), 4.85 (1H, d), 4.91 (2H, s), 6.76-6.83 (3H, m), 6.99 (1H, s), 7.08-7.33 (21H, m), 7.42 (1H, s), 7.59 (1H, d), 7.67 (1H, d).<br>EI-MS (m/z); 848 [M + H]⁺ |

TABLE 14

| Ex. | STRUCTURE | DATA |
|---|---|---|
| 43 | 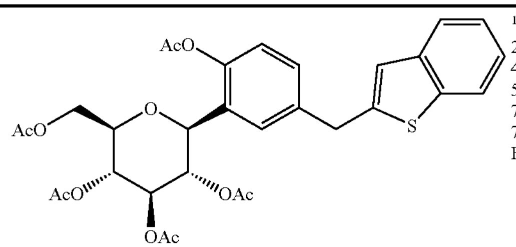 | ¹H-NMR (CDCl₃); 1.73 (3H, s), 2.00 (3H, s), 2.04 (6H, s), 2.36 (3H, s), 3.80 (1H, ddd), 4.09 (1H, dd), 4.21 (2H, s), 4.30 (1H, dd), 4.57-4.63 (1H, m), 5.17-5.22 (1H, m), 5.28-5.32 (2H, m), 6.98 (1H, s), 7.04 (1H, d), 7.24-7.32 (3H, m), 7.36 (1H, d), 7.67 (1H, d), 7.73 (1H, d)<br>FAB-MS (m/z); 612 [M + H]⁺ |
| 44 | 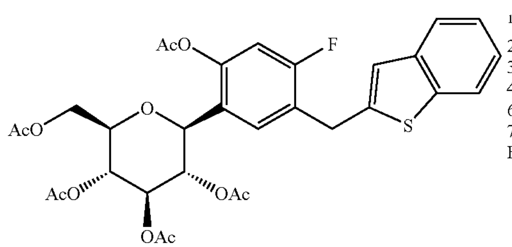 | ¹H-NMR (CDCl₃); 1.74 (3H, s), 1.99 (3H, s), 2.02 (3H, s), 2.04 (3H, s) 2.36 (3H, s), 3.75-3.82 (1H, m), 4.07 (1H, dd), 4.22 (2H, brs), 4.28 (1H, dd), 4.55 (1H, d), 5.13-5.33 (3H, m), 6.88 (1H, d), 7.00 (1H, s), 7.22-7.37 (3H, m), 7.64-7.78 (2H, m)<br>EI-MS (m/z); 653 [M + Na]⁺ |

TABLE 14-continued

| Ex. | STRUCTURE | DATA |
|---|---|---|
| 45 | 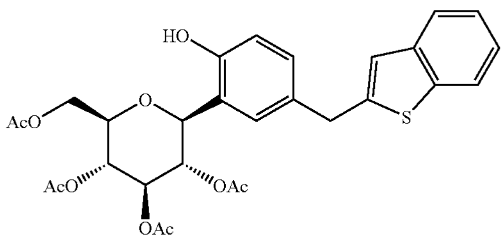 | $^1$H-NMR (CDCl$_3$); 1.60 (3H, s), 1.98 (3H, s), 2.05 (3H, s), 2.12 (3H, s), 3.83-3.88 (1H, m), 4.10 (2H, s), 4.17 (1H, dd), 4.33 (1H, dd), 4.52-4.56 (1H, m), 5.27-5.31 (3H, m), 6.87-6.89 (2H, m), 6.94 (1H, d), 6.97 (1H, s), 7.16-7.31 (2H, m), 7.64 (1H, d), 7.71 (1H, dd)<br>FAB-MS (m/z); 570 [M + H]$^+$ |
| 46 | 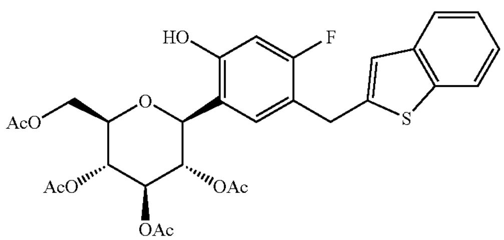 | $^1$H-NMR (CDCl$_3$); 1.59 (3H, s), 1.98 (3H, s), 2.05 (3H, s), 2.12 (3H, s), 3.80-3.87 (1H, m), 4.07 (1H, t), 4.31 (1H, dd), 4.47-4.53 (1H, m), 5.21-5.30 (3H, m), 6.66 (1H, d), 6.83 (1H, d), 6.96 (1H, s), 7.22-7.32 (2H, m), 7.64 (1H, d), 7.71 (1H, d)<br>EI-MS (m/z); 611 [M + Na]$^+$ |
| 47 | 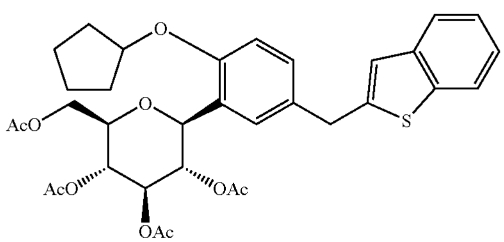 | $^1$H-NMR (CDCl$_3$); 1.60-1.69 (2H, m), 1.71 (3H, s), 1.78-1.92 (6H, m), 2.00 (3H, s), 2.036 (3H, s), 2.040 (3H, s), 3.78-3.83 (1H, m), 4.10-4.18 (3H, m), 4.26 (1H, dd), 4.75-4.85 (2H, m), 520 (1H, t), 5.30-5.40 (2H, m), 6.80 (1H, d), 6.95 (1H, s), 7.15 (1H, dd), 7.20-7.30 (3H, m), 7.65 (1H, d), 7.71 (1H, d).<br>FAB-MS (m/z); 638 [M + H]$^+$ |
| 48 | 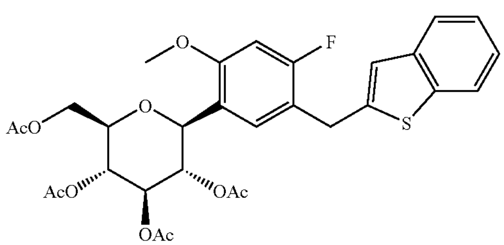 | $^1$H-NMR (CDCl$_3$); 1.73 (3H, s), 1.99 (3H, s), 2.02 (3H, s), 2.04 (3H, s), 3.77-3.85 (4H, m), 4.09-4.19 (3H, m), 4.24 (1H, dd), 4.77-4.86 (1H, m), 5.16-5.24 (1H, m), 5.28-5.38 (2H, m), 6.61 (1H, d), 6.96 (1H, s), 7.20-7.32 (3H, m), 7.65 (1H, d), 7.72 (1H, d)<br>EI-MS (m/z); 625 [M + Na]$^+$ |

TABLE 15

| Ex. | STRUCTURE | DATA |
|---|---|---|
| 49 | 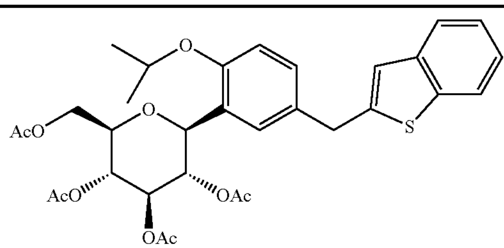 | $^1$H-NMR (CDCl$_3$); 1.35 (3H, d), 1.36 (3H, d), 1.72 (3H, s), 2.00 (3H, s), 2.03 (3H, s), 2.04 (3H, s), 3.81-3.85 (1H, m), 4.11-4.14 (3H, m), 4.24 (1H, dd), 4.50-4.56 (1H, m), 4.92 (1H, brs), 5.21 (1H, t), 5.32-5.38 (2H, m), 6.81 (1H, d), 6.96 (1H, s), 7.15 (1H, dd), 7.21-7.30 (3H, m), 7.66 (1H, d), 7.72 (1H, dd).<br>EI-MS (m/z); 613 [M + H]$^+$ |

TABLE 15-continued

| Ex. | STRUCTURE | DATA |
|---|---|---|
| 50 | 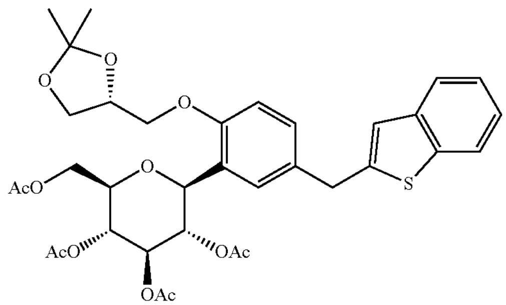 | $^1$H-NMR (CDCl$_3$); 1.42 (3H, s), 1.50 (3H, s), 1.71 (3H, s), 1.99 (3H, s), 2.04 (6H, s), 3.81-3.86 (1H, m), 3.97-4.06 (3H, m), 4.10-4.22 (4H, m), 4.27 (1H, dd), 4.48-4.54 (1H, m), 4.80-4.90 (1H, br), 5.21 (1H, t), 5.31 (1H, t), 5.35-5.45 (1H, br), 6.82 (1H, d), 6.95 (1H, d), 7.17-7.31 (4H, m), 7.66 (1H, d), 7.72 (1H, dd). FAB-MS (m/z); 685 [M + H]$^+$ |
| 51 | 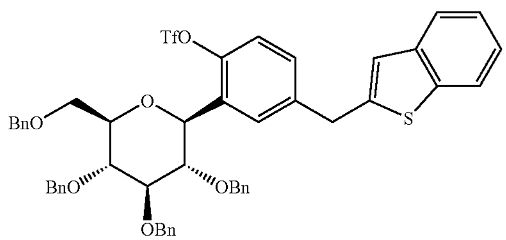 | $^1$H-NMR (DMSO-d$_6$), 3.62-3.84 (6H, m), 4.02 (1H, d), 4.19 (2H, s), 4.44-4.62 (5H, m), 4.83-4.88 (3H, m), 6.83 (2H, m), 6.99 (1H, s), 7.06-7.33 (22H, m), 7.44 (1H, d), 7.60 (1H, m), 7.68 (1H, m) ES-MS (m/z); 917 [M + Na]$^+$ |
| 52 | 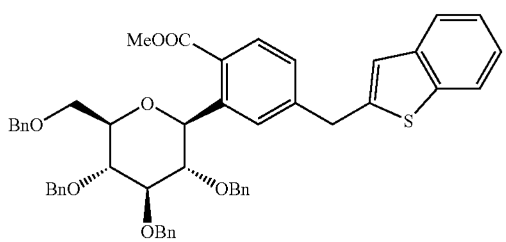 | $^1$H-NMR (DMSO-d$_6$); 3.55 (1H, m), 3.71 (3H, s), 3.76-3.86 (6H, m), 4.22 (2H, s), 4.38 (1H, d), 4.52 (1H, d), 4.61 (1H, d), 4.63 (1H, d), 4.84-4.93 (3H, m), 5.37 (1H, d), 6.90-6.93 (2H, m), 6.96 (1H, s), 7.12-7.30 (21H, m), 7.59 (2H, m), 7.68 (1H, d), 7.74 (1H, d) ES-MS (m/z); 827 [M + Na]$^+$ |
| 53 | 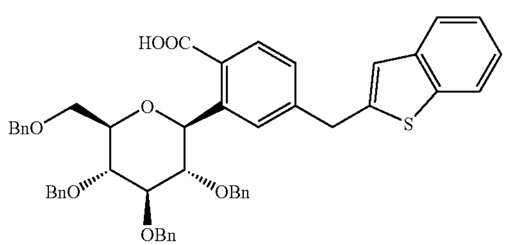 | $^1$H-NMR (DMSO-d$_6$), 3.56-3.81 (7H, m), 4.24 (1H, d), 4.32 (2H, s), 4.45-4.59 (3H, m), 4.73-4.78 (3H, m), 5.37 (1H, d), 6.84 (2H, d), 7.01-7.40 (22H, m), 7.66 (2H, m), 7.77 (2H, d), 12.9 (1H, s) FAB-MS (m/z); 791[M + H]$^+$ |
| 54 | 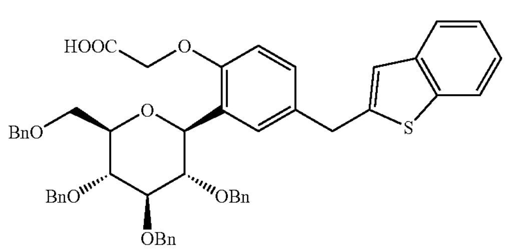 | $^1$H-NMR (CDCl$_3$); 3.62 (1H, m), 3.69-3.83 (5H, m), 3.99 (1H, d), 4.18 (2H, s), 4.25-4.68 (7H, m), 4.85 (1H, d), 4.93 (2H, s), 6.72-6.78 (3H, m), 7.00 (1H, m), 7.03-7.09 (2H, m), 7.13-7.19 (3H, m), 7.23-7.36 (17H, m), 7.63 (1H, d), 7.70 (1H, d) FAB-MS (m/z); 819 [M − H]$^-$ |

TABLE 16

| Ex. | STRUCTURE | DATA |
|---|---|---|
| 55 | 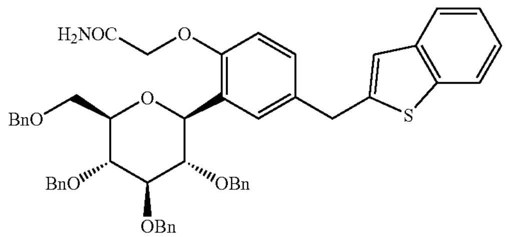 | ¹H-NMR (CDCl₃); 3.54 (1H, m), 3.72-3.87 (5H, m), 3.91 (1H, d), 4.18 (2H, s), 4.29 (1H, m), 4.40-4.55 (6H, m), 4.63-4.70 (2H, m), 4.88-4.96 (3H, m), 6.72-6.80 (3H, m), 7.00 (1H, s), 7.04-7.10 (2H, m), 7.14 (1H, d), 7.21-7.36 (19H, m), 7.62 (1H, d), 7.70 (1H, d)<br>FAB-MS (m/z); 819 [M − H]⁻ |
| 56 | 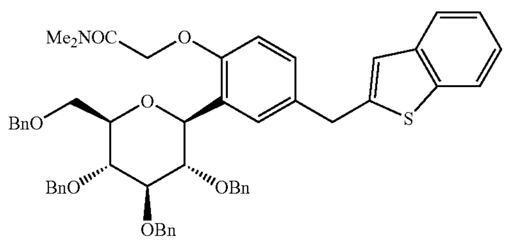 | ¹H-NMR (CDCl₃); 2.81 (3H, s), 2.85 (3H, s), 3.54-3.83 (6H, m), 3.91 (1H, d), 4.12-4.23 (2H, m), 4.41-4.66 (7H, m), 4.84-4.97 (3H, m), 6.80-6.85 (2H, m), 6.91 (1H, d), 6.96 (1H, d), 7.08-7.33 (21H, m), 7.42 (1H, brs), 7.56 (1H, d), 7.64 (1H, d)<br>FAB-MS (m/z); 849 [M + H]⁺ |
| 57 | 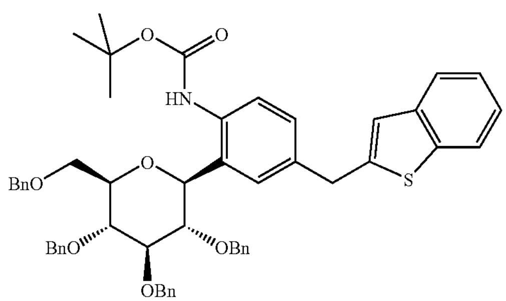 | ¹H-NMR (CDCl₃); 1.48 (9H, s), 3.53 (1H, m), 3.70-3.85 (5H, m), 4.15 (2H, s), 4.35 (2H, t), 4.55-4.63 (4H, m), 4.85-4.95 (3H, m), 6.90-6.95 (3H, m), 7.10-7.31 (23H, m), 7.60 (1H, d), 7.69 (1H, d), 8.05 (1H, m)<br>ES-MS (m/z); 884 [M + Na]⁺ |
| 58 | 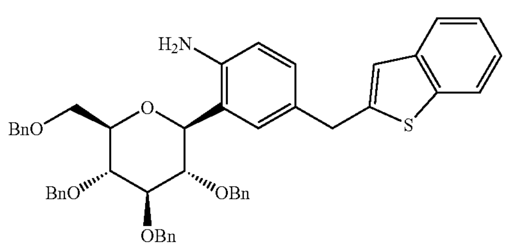 | ¹H-NMR (CDCl₃); 3.52 (1H, d), 3.71-3.90 (5H, m), 4.06 (1H, m), 4.10 (2H, s), 4.32-4.61 (5H, m), 4.85-4.97 (3H, m), 6.92-6.96 (3H, m), 7.07-7.32 (23H, m), 7.60 (1H, d), 7.68 (1H, d)<br>ES-MS (m/z); 762 [M + H]⁺ |
| 59 | 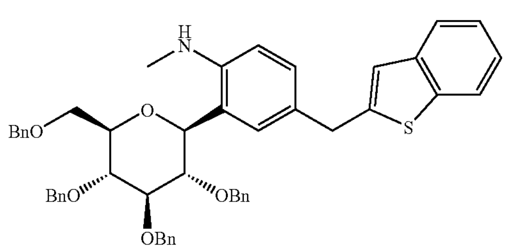 | ¹H-NMR (CDCl₃); 2.62 (3H, s), 3.52 (1H, d), 3.74-3.93 (5H, m), 4.11 (2H, s), 4.33 (2H, m), 4.45-4.64 (4H, m), 4.85-4.96 (4H, m), 6.90 (2H, m), 6.96 (1H, s), 7.09-7.33 (23H, m), 7.59 (1H, d), 7.68 (1H, d)<br>FAB-MS (m/z); 776 [M + H]⁺ |
| 60 | 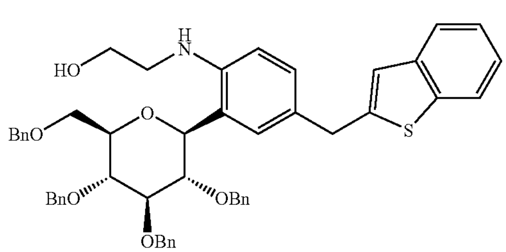 | ¹H-NMR (CDCl₃); 3.08-3.14 (2H, m), 3.51-3.66 (3H, m), 3.70-3.88 (5H, m), 3.98-4.07 (1H, m), 4.10 (2H, s), 4.32 (1H, d), 4.34 (1H, d), 4.45-4.60 (4H, m), 4.84-5.01 (4H, m), 6.65 (1H, d), 6.89.6.91 (2H, m), 6.97 (2H, m), 7.06-7.33 (21H, m), 7.59 (1H, d), 7.68 (1H, d)<br>ES-MS (m/z); 806 [M + H]⁺ |

TABLE 17

| Ex. | STRUCTURE | DATA |
|---|---|---|
| 61 | (structure) | ¹H-NMR (CDCl₃); 3.56 (1H, m), 3.67-3.80 (6H, m), 3.83-3.92 (2H, m), 3.98 (1H, m), 4.03 (1H, d), 4.11 (1H, m), 4.16 (2H, s), 4.39-4.53 (5H, m), 4.81-4.95 (3H, m), 6.79-6.85 (3H, m), 6.99 (1H, s), 7.04-7.09 (2H, m), 7.11-7.17 (3H, m), 7.19-7.33 (17H, m), 7.60 (1H, d), 7.69 (1H, d) FAB-MS (m/z); 808 [M + H]⁺ |
| 62 | (structure) | ¹H-NMR (CDCl₃); 3.38-4.15 (12H, m), 4.19-4.31 (2H, m), 4.36-4.66 (4H, m), 4.80-4.94 (3H, m), 6.80-6.98 (3H, m), 7.03-7.10 (1H, m), 7.12-7.35 (21H, m), 7.52-7.60 (1H, m), 7.61-7.69 (1H, m) EI-MS (m/z); 863[M + Na]⁺ |
| 63 | (structure) | ¹H-NMR (CDCl₃); 2.97 (1H, m), 2.95 (1H, m), 3.59 (1H, brs), 3.71-3.82 (6H, m), 3.89-3.97 (1H, m), 4.18 (2H, d), 4.43 (1H, d), 4.47-4.65 (3H, m), 4.84-4.97 (3H, m), 6.79-6.87 (2H, m), 6.98 (1H, s), 7.08-7.17 (2H, m), 7.18-7.34 (20H, m), 7.39 (1H, s), 7.58 (1H, d), 7.67 (1H, d) FAB-MS (m/z); 807 [M + H]⁺ |
| 64 | (structure) | ¹H-NMR (CDCl₃); 2.69 (6H, s), 3.64-3.82 (5H, m), 3.93 (1H, d), 4.16 (2H, d) 4.37 (1H, d), 4.48 (1H, d), 4.58-4.64 (2H, m), 4.85-4.94 (4H, m), 6.76 (2H, m), 6.94 (1H, s), 7.10-7.28 (22H, m), 7.43 (1H, m), 7.49 (1H, d), 7.60 (1H, d) ES-MS (u/z); 790 [M + H]⁺ |
| 65 | (structure) | ¹H-NMR (CDCl₃); 3.42-3.48 (1H, m), 3.55-3.58 (1H, m), 3.72-3.78 (4H, m), 3.83 (1H, d), 4.14-4.30 (3H, m), 4.39 (1H, d), 4.51-4.67 (4H, m), 4.83-4.94 (2H, m), 6.86-6.90 (1H, m), 6.98 (1H, brs), 7.06-7.37 (24H, m), 7.57-7.60 (1H, m), 7.66-7.69 (1H, m) EI-MS (m/z); 787 [M + Na]⁺ |
| 66 | (structure) | ¹H-NMR (CDCl₃); 3.42-3.48 (1H, m), 3.50-3.64 (1H, m), 3.72-3.78 (4H, m), 3.88 (1H, d), 4.19 (1H, d), 4.22-4.34 (2H, m), 4.35-4.45 (1H, m), 4.50-4.65 (4H, m), 4.85 (1H, d), 4.89 (1H, d), 6.90 (2H, d), 6.94 (1H, s), 7.10-7.42 (23H, m), 7.56 (1H, d), 7.65 (1H, d) |

TABLE 18

| Ex. | STRUCTURE | DATA |
|---|---|---|
| 67 | (structure) | $^1$H-NMR (CDCl$_3$); 3.60-3.68 (1H, m), 3.73-3.85 (3H, m), 3.92-4.23 (3H, m), 4.42-4.78 (8H, m), 4.83-4.95 (2H, m), 6.85-6.98 (3H, m), 7.05-4.39 (23H, m), 7.54-7.61 (1H, m), 7.62-7.69 (1H, m) |
| 68 | (structure) | $^1$H-NMR (CDCl$_3$); 3.40-3.63 (4H, m), 3.68-3.90 (4H, m), 4.10-4.40 (4H, m), 4.45-4.75 (5H, m), 4.80-4.95 (3H, m), 5.22 (2H, s), 6.84-6.95 (3H, m), 7.05-7.40 (23H, m), 7.54 (1H, d), 7.65 (1H, d) |
| 69 | (structure) | $^1$H-NMR (CDCl$_3$); 3.47-3.78 (1H, m), 3.87 (3H, s), 4.13-4.29 (4H, m), 4.33 (1H, d), 4.49-4.75 (4H, m), 4.84-4.94 (3H, m), 6.86-6.95 (3H, m), 7.06-7.37 (23H, m), 7.58 (1H, d), 7.66 (1H, d) FAB-MS (m/z); 775 [M − H]$^-$ |
| 70 | (structure) | $^1$H-NMR (CDCl$_3$); 3.48-3.62 (2H, d), 3.72-3.82 (5H, d), 4.19 (2H, s), 4.22 (1H, d), 4.34 (1H, d), 4.53 (1H, d), 4.63 (2H, d), 4.84-4.94 (3H, m), 6.89 (2H, dd), 6.93 (1H, s), 7.15-7.40 (24H, m), 7.65 (1H, dd), 7.83 (1H, brd) |
| 71 | (structure) | $^1$H-NMR (CDCl$_3$); 3.50 (1H, m), 3.58 (1H, m), 3.74-3.81 (5H, m), 4.16 (2H, s), 4.22 (1H, d), 4.34 (1H, d), 4.52-4.65 (3H, m), 4.85-4.94 (3H, m), 6.87-6.89 (2H, m), 7.00-7.06 (2H, m), 7.15-7.36 (22H, m), 7.45 (1H, dt), 8.50 (1H, m) FAB-MS (m/z); 692 [M + H]$^+$ |
| 72 | (structure) | $^1$H-NMR (CDCl$_3$); 3.36-3.62 (5H, m), 4.21 (1H, d), 4.30 (2H, s), 4.52 (1H, d), 4.60 (1H, d), 4.62 (1H, d), 4.83-4.97 (3H, m), 6.84-6.90 (2H, m), 7.12-7.78 (26H, m) FAB-MS (m/z); 765 [M + H]$^+$ |

TABLE 18-continued

| Ex. | STRUCTURE | DATA |
|---|---|---|
| 73 | 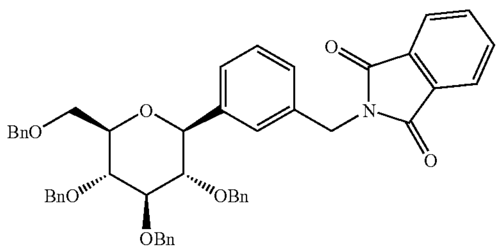 | ¹H-NMR (CDCl₃); 3.50-3.60 (2H, m), 3.72-3.81 (5H, m), 4.22 (1H, d), 4.36 (1H, d), 4.54 (1H, d), 4.62-4.66 (2H, m), 4.72-4.94 (5H, m), 6.82-6.87 (2H, m), 7.11-7.13 (3H, m), 7.19-7.40 (18H, m), 7.53 (1H, s), 7.65-7.68 (2H, m), 7.77-7.80 (2H, m). EI-MS (m/z); 782 [M + Na]⁺ |

TABLE 19

| Ex. | STRUCTURE | DATA |
|---|---|---|
| 74 | 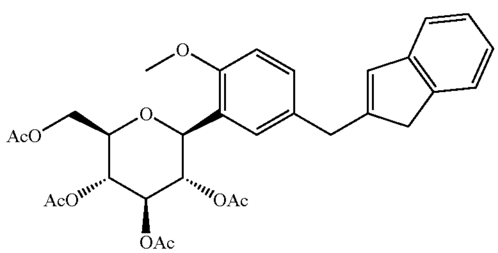 | ¹H-NMR (CDCl₃); 1.73 (3H, s), 2.00 (3H, s), 2.04 (3H, s), 2.05 (3H, s), 3.25 (2H, s), 3.74 (2H, s), 3.82 (3H, s), 3.84 (1H, m), 4.14 (1H, dd), 4.26 (1H, dd), 4.92 (1H, m), 5.23 (1H, m), 5.33 (2H, m), 6.46 (1H, s), 6.79 (1H, d), 7.08-7.35 (6H, m) ES-MS (m/z); 567 [M + H]⁺ |
| 75 | 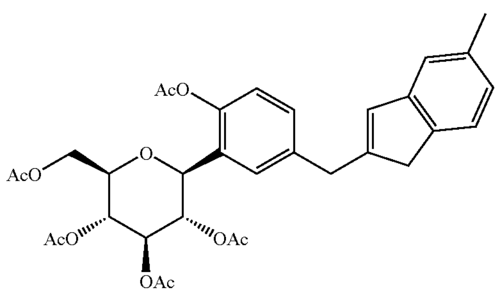 | ¹H-NMR (CDCl₃); 2.29 (3H, s), 2.32 (3H, s), 3.43 (2H, m), 3.58 (2H, m), 3.83 (1H, m), 3.88 (1H, m), 3.99 (2H, s), 4.48 (1H, d), 6.25 (1H, s), 6.83 (1H, d), 7.10 (1H, d), 7.15 (1H, s), 7.20 (2H, s) ES-MS (m/z); 608 [M]⁺ |
| 76 | 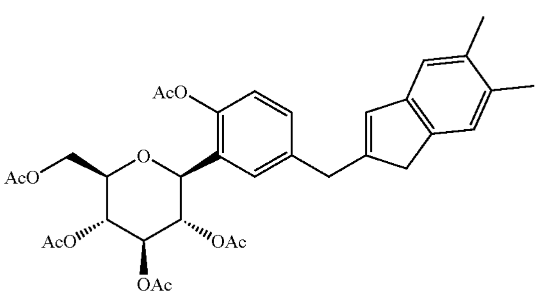 | ¹H-NMR (CDCl₃); 3.26 (2H, s), 3.40 (2H, m), 3.53 (2H, m), 3.67 (1H, dd), 3.76 (2H, s), 3.82 (3H, s), 3.86 (1H, m), 4.70 (1H, d), 6.48 (1H, s), 6.91 (1H, d), 7.01 (1H, m), 7.03-7.22 (3H, m), 7.29 (1H, d), 7.32 (1H, d) ES-MS (m/z); 622[M]⁺ |
| 77 | 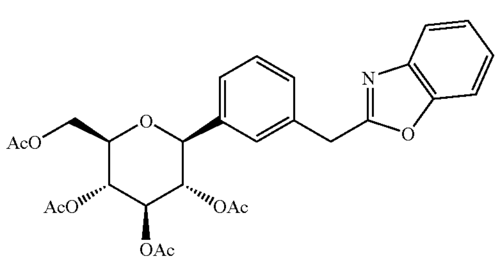 | ¹H-NMR (CDCl₃); 1.71 (3H, s), 1.99 (3H, s), 2.06 (3H, s), 2.11 (3H, s), 3.82 (1H, m), 4.14 (1H, m), 4.25 (2H, s), 4.27 (1H, dd), 4.39 (1H, d), 5.10 (1H, t), 5.22 (1H, t), 5.31 (1H, t) 7.28-7.38 (6H, m), 7.45 (1H, m), 7.67 (1H, m) ES-MS (m/z); 540[M + H]⁺ |

TABLE 19-continued

| Ex. | STRUCTURE | DATA |
| --- | --- | --- |
| 78 | 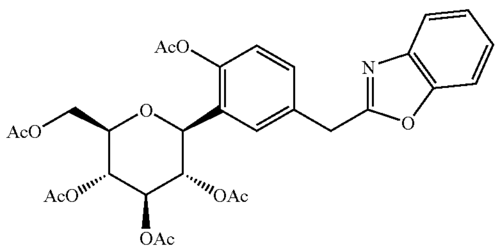 | ¹H-NMR (CDCl₃); 1.76 (3H, s), 2.01 (3H, s), 2.05 (3H, s), 2.09 (3H, s), 2.35 (3H, s), 3.81 (1H, m), 4.30 (1H, dd), 4.60 (1H, d), 4.80 (2H, s), 5.16-5.34 (4H, m), 7.03 (1H, d), 7.40-7.59 (4H, m), 7.70 (1H, dd), 8.32 (1H, d) ES-MS (m/z); 598 [M + H]⁺ |
| 79 | 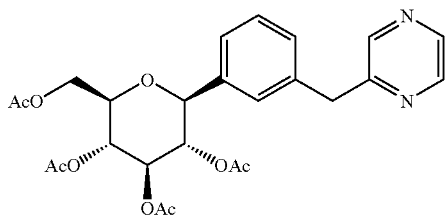 | ¹H-NMR (CDCl₃); 1.75 (3H, s), 1.99 (3H, s), 2.06 (3H, s), 2.08 (3H, s), 3.82 (1H, m), 4.13 (1H, m), 4.17 (2H, s), 4.27 (1H, dd), 4.37 (1H, d), 5.11 (1H, t), 5.22 (1H, t), 5.31 (1H, t), 7.21-7.32 (4H, m), 8.43 (2H, m), 8.53 (1H, s) ES-MS (m/z); 501 [M + H]⁺ |

TABLE 20

| Ex. | STRUCTURE | DATA |
| --- | --- | --- |
| 80 | 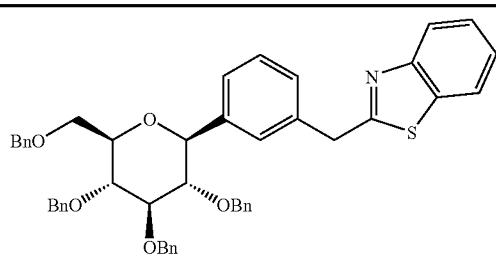 | ¹H-NMR (CDCl₃); 3.49-3.54 (1H, m), 3.58-3.62 (1H, m), 3.74-3.82 (5H, m), 4.25 (1H, d), 4.37 (1H, d), 4.44 (2H, s), 4.55 (1H, d), 4.63 (2H, d), 4.86 (1H, d), 4.88 (1H, d), 4.93 (1H, d), 6.88-6.90 (2H, m), 7.10-7.48 (24H, m), 7.71 (1H, d), 7.97 (1H, d). FAB-MS (m/z); 748 [M + H]⁺ |
| 81 | 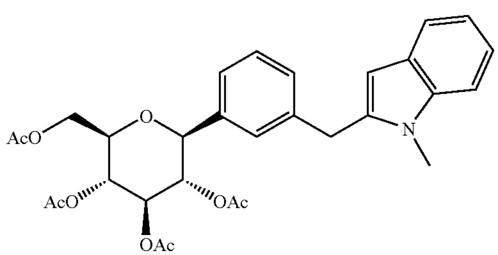 | ¹H-NMR (CDCl₃); 1.68 (3H, s), 1.98 (3H, s), 2.05 (3H, s), 2.06 (3H, s), 3.54 (3H, s) 3.82 (1H, m), 4.11-4.16 (2H, m), 4.17 (1H, d), 4.28 (1H, dd), 4.35 (1H, d), 5.10 (1H, t), 5.18-5.33 (2H, m), 6.24 (1H, s), 7.07 (1H, m), 7.13-7.20 (3H, m), 7.21-7.31 (3H, m), 7.54 (1H, d) FAB-MS (m/z); 552 [M + H]⁺ |
| 82 | 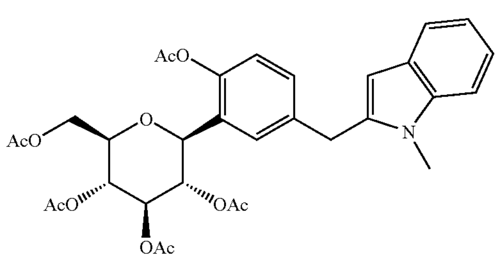 | ¹H-NMR (CDCl₃); 1.74 (3H, s), 2.00 (3H, s), 2.04 (6H, s), 2.35 (3H, s), 3.55 (3H, s), 3.81 (1H, m), 4.10 (1H, dd), 4.13 (2H, s), 4.30 (1H, dd), 4.59 (1H, d), 5.21 (1H, m), 5.23-5.34 (2H, m), 6.26 (1H, brs), 6.99 (1H, d), 7.05-7.20 (3H, m), 7.26 (1H, m), 7.33 (1H, d), 7.55 (1H, m) FAB-MS (m/z); 610 [M + H]⁺ |

TABLE 20-continued

| Ex. | STRUCTURE | DATA |
| --- | --- | --- |
| 83 | 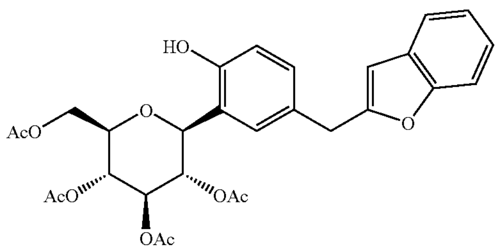 | $^1$H-NMR (CDCl$_3$); 1.64 (3H, s), 1.90 (3H, s), 2.12 (3H, s), 2.60 (3H, s), 3.96 (1H, m), 3.98 (2H, s), 4.17 (1H, m), 4.32 (1H, dd), 4.56 (1H, m), 5.24-5.34 (3H, m), 6.31 (1H, s), 6.88 (1H, m), 7.00-7.48 (7H, m)<br>FAB-MS (m/z); 553 [M − H]$^-$ |
| 84 | 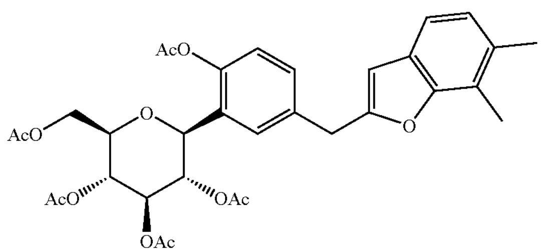 | $^1$H-NMR (CDCl$_3$); 1.74 (3H, s), 2.00 (3H, s), 2.04 (3H, s), 2.05 (3H, s), 2.35 (3H, s), 3.82 (1H, m), 4.09 (3H, m), 4.30 (1H, dd), 4.60 (1H, m), 5.20-5.32 (3H, m), 6.29 (1H, s), 6.96-7.03 (3H, m), 7.18 (1H, d), 7.37 (1H, s)<br>ES-MS (m/z); 642 [M + NH$_4$]$^+$ |
| 85 | 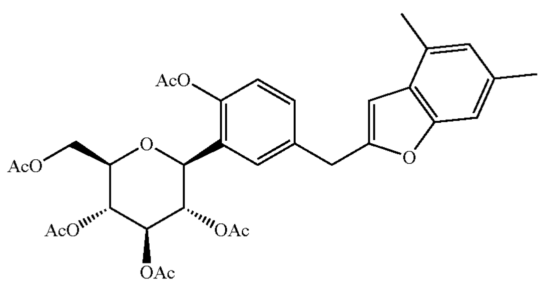 | $^1$H-NMR (CDCl$_3$); 1.73 (3H, s), 2.01 (3H, s), 2.04 (3H, s), 2.07 (3H, s) 2.36 (3H, s), 2.39 (3H, s), 2.41 (3H, s), 3.80 (1H, m), 4.07 (1H, m), 4.30 (1H, dd), 4.59 (1H, d), 5.19 (1H, m), 5.30 (2H, m), 6.32 (1H, s), 6.81 (1H, s), 7.01 (1H, s), 7.03 (1H, s), 7.25 (1H, s), 7.35 (1H, s)<br>ES-MS (m/z); 642 [M + NH$_4$]$^+$ |

TABLE 21

| Ex. | STRUCTURE | DATA |
| --- | --- | --- |
| 86 | 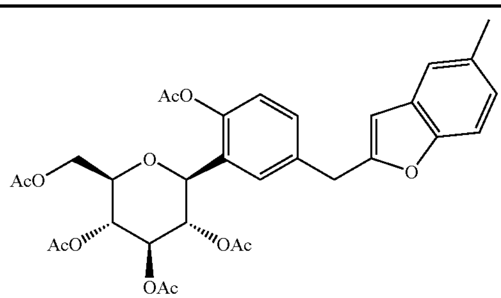 | $^1$H-NMR (CDCl$_3$); 1.79 (3H, s), 1.99 (3H, s), 2.05 (3H, s), 2.09 (3H, s), 2.34 (3H, s), 2.35 (3H, s), 3.80 (1H, m), 4.07 (2H, s), 4.11 (1H, m), 4.28 (1H, m), 4.60 (1H, m), 5.28 (1H, m), 6.30 (1H, s), 6.93 (1H, d), 7.02 (3H, m), 7.26 (1H, m), 7.35 (1H, s)<br>ES-MS (m/z); 628 [M + NH$_4$]$^+$ |
| 87 | 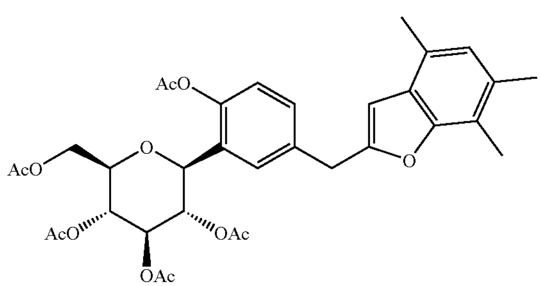 | $^1$H-NMR (CDCl$_3$); 1.74 (3H, s), 2.00 (3H, s), 2.04 (3H, s), 2.05 (3H, s) 2.32 (3H, s), 2.35 (3H, s), 2.36 (3H, s), 2.38 (3H, s), 3.81 (1H, m), 4.08 (2H, s), 4.09 (1H, m), 4.30 (1H, dd), 4.59 (1H, d), 5.20 (1H, m), 5.30 (2H, m), 6.29 (1H, s), 6.79 (1H, s), 7.02 (1H, d), 7.26 (1H, m), 7.37 (1H, d)<br>ES-MS (m/z); 656 [M + NH$_4$]$^+$ |

TABLE 21-continued

| Ex. | STRUCTURE | DATA |
|---|---|---|
| 88 | 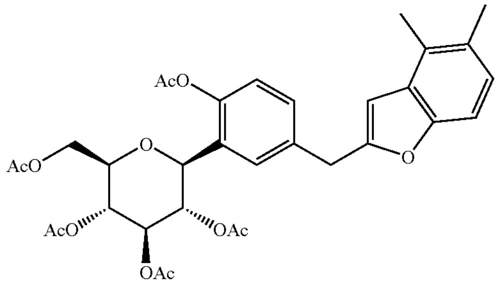 | ¹H-NMR (CDCl₃); 1.74 (3H, s), 2.00 (3H, s), 2.04 (6H, s), 2.32 (3H, s), 2.34 (3H, s), 2.35 (3H, s), 3.80 (1H, m), 4.12 (3H, m), 4.30 (1H, dd), 4.59 (1H, m), 4.92 (1H, m), 5.21 (1H, m), 5.30 (2H, m), 6.36 (1H, s), 7.00 (1H, d), 7.02 (1H, d), 7.12 (1H, d), 7.26 (1H, m), 7.36 (1H, s) ES-MS (m/z); 642 [M + NH₄]⁺ |
| 89 | 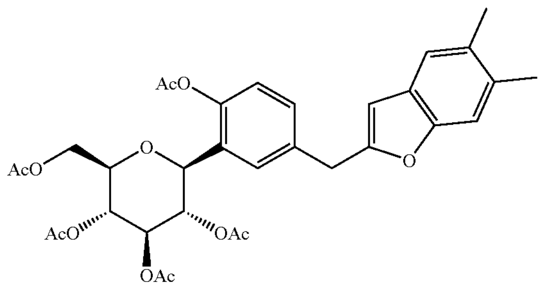 | ¹H-NMR (CDCl₃); 1.65 (3H, s), 1.99 (3H, s), 2.05 (3H, s), 2.08 (3H, s), 2.12 (3H, s), 2.31 (3H, s), 2.33 (3H, s), 3.86 (1H, m), 3.94 (2H, m), 4.16 (1H, m), 4.31 (1H, dd), 4.52 (1H, m), 5.28 (3H, m), 6.20 (1H, s), 6.85 (2H, m), 6.98 (1H, s), 7.13 (1H, s), 7.19 (1H, s) ES-MS (m/z); 642[M + NH₄]⁺ |
| 90 | 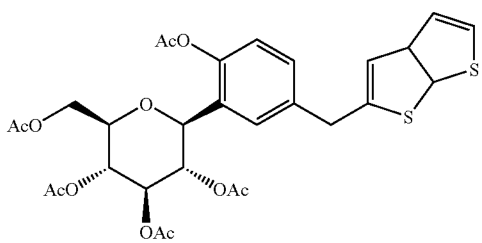 | ¹H-NMR (CDCl₃); 1.12 (1H, d), 1.73 (2H, s), 1.98-2.12 (10H, m), 2.33-2.35 (3H, dd), 3.79-3.81 (1H, m), 4.06-4.09 (1H, d), 4.18 (2H, s), 4.28-4.33 (1H, dd), 4.58-4.60 (1H, m), 5.28-5.30 (2H, m), 6.92 (1H, s), 7.00-7.02 (1H, d), 7.12-7.13 (1H, d) 7.23-7.31 (3H, m) ES-MS (m/z); 636 [M + NH₄]⁺ |
| 91 | 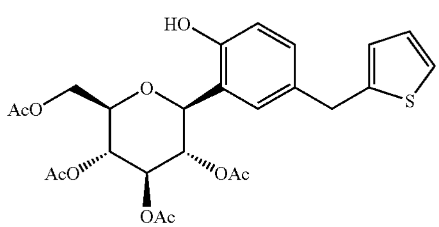 | ¹H-NMR (CDCl₃); 1.67 (3H, s), 2.00 (3H, s), 2.06 (3H, s), 2.12 (3H, s), 3.83-3.89 (1H, m), 4.03 (2H, s), 4.17 (1H, dd), 4.32 (1H, dd), 4.50-4.59 (1H, m), 5.25-5.35 (3H, m), 6.70-7.03 (4H, m), 7.10-7.25 (2H, m) FAB-MS (m/z); 521 [M + H]⁺ |

TABLE 22

| Ex. | STRUCTURE | DATA |
|---|---|---|
| 92 | 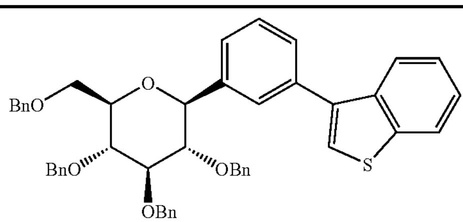 | ¹H-NMR (CDCl₃); 3.50-3.92 (7H, m), 4.33 (1H, dd), 4.49 (1H, d), 4.53-4.70 (3H, m), 4.85-5.00 (3H, m), 6.92 (2H, d), 7.06-7.93 (27H, m) EI-MS (ES): 756 [M + Na]⁺ |

TABLE 22-continued

| Ex. | STRUCTURE | DATA |
|---|---|---|
| 93 | 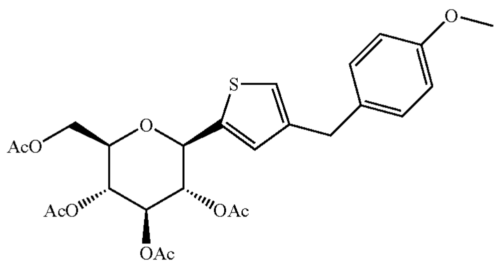 | ¹H-NMR (CDCl₃); 1.79 (3H, s), 2.00 (3H, s), 2.04 (3H, s), 2.08 (3H, s), 3.76-3.85 (6H, m), 4.16 (1H, dd), 4.26 (1H, dd), 4.61 (1H, d), 5.07-5.31 (3H, m), 6.77-6.90 (4H, m), 7.07 (2H, d) EI-MS; 534 |
| 94 | 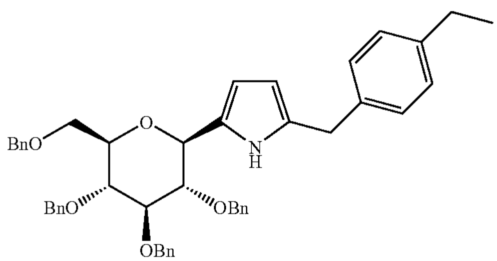 | ¹H-NMR (CDCl₃); 1.19 (3H, t), 2.59 (2H, q), 3.40-3.98 (9H, m), 4.22 (1H, d), 4.33 (1H, d), 4.45-4.62 (4H, m), 4.80-4.96 (3H, m), 5.95 (1H, dd), 6.18 (1H, dd), 6.85-7.33 (26H, m), 8.17 (1H, s) FAB-MS (m/z); 708 [M + H]⁺ |
| 95 | 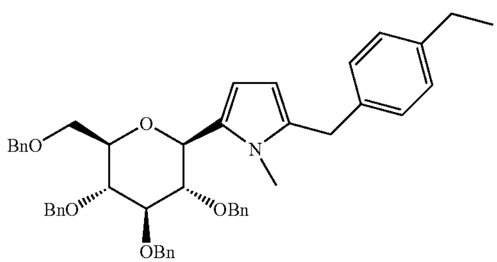 | ¹H-NMR (CDCl₃); 1.20 (3H, t), 2.59 (2H, q), 3.40 (3H, s), 3.49-3.56 (1H, m), 3.65-3.78 (5H, m), 3.91 (2H, s), 4.03 (1H, d), 4.31 (1H, d), 4.39 (1H, d), 4.47-4.64 (3H, m), 4.82-4.97 (3H, m), 5.94 (1H, d), 6.20 (1H, d), 6.98-7.34 (26H, m) FAB-MS (m/z); 722 [M + H]⁺ |
| 96 | 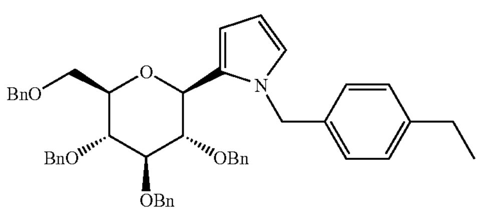 | ¹H-NMR (CDCl₃); 1.18 (3H, t), 2.58 (2H, q), 3.38-3.45 (1H, m), 3.60-3.78 (5H, m), 4.11 (1H, d), 4.31 (1H, d), 4.40-4.63 (4H, m), 4.80-4.95 (3H, m), 5.08 (1H, d), 5.15 (1H, d), 6.17 (1H, dd), 6.31 (1H, dd), 6.64 (1H, dd), 6.97-7.33 (24H, m) FAB-MS (m/z); 708 [M + H]⁺ |
| 97 | 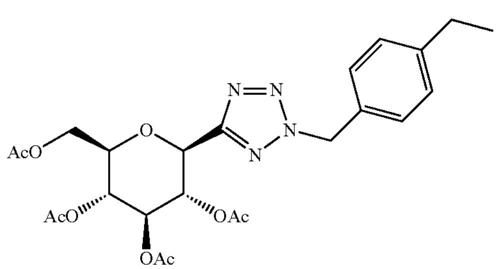 | ¹H-NMR (CDCl₃); 1.21 (3H, t), 1.71 (3H, s), 2.01 (3H, s), 2.05 (3H, s), 2.07 (3H, s), 2.63 (2H, dd), 3.88 (1H, dddd), 4.15 (1H, dd), 4.28 (1H, dd), 4.87 (1H, d), 5.23 (1H, t), 5.33 (1H, t) 5.55 (1H, dd), 5.71 (2H, s), 7.18-7.29 (4H, m) FAB-MS (m/z); 519 [M + H]⁺ |
| 98 | 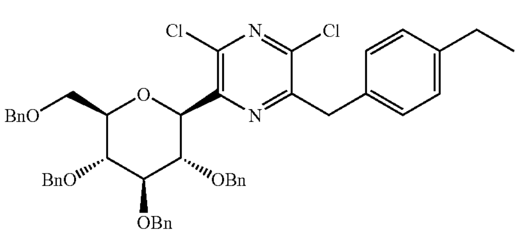 | ¹H-NMR (CDCl₃); 1.10 (3H, t), 2.50 (2H, q), 3.63-3.68 (1H, m), 3.72-3.82 (3H, m), 3.90 (1H, t), 4.10-4.23 (4H, m), 4.49 (1H, d), 4.59-4.66 (3H, m), 4.78 (1H, d), 4.86-4.97 (3H, m), 6.78 (2H, d), 6.97 (2H, d), 7.09-7.33 (20H, m) EI-MS (m/z); 789 [M + H]⁺ |

TABLE 23

| Ex. | STRUCTURE | DATA |
|---|---|---|
| 99 | 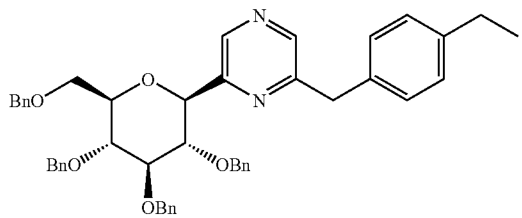 | ¹H-NMR (CDCl₃); 1.15 (3H, t), 2.54 (2H, q), 3.63-3.68 (1H, m), 3.74-3.81 (3H, m), 3.87 (1H, t), 3.93-4.00 (2H, m), 4.11 (2H, s), 4.43 (1H, d), 4.48 (1H, d), 4.53 (1H, d), 4.59 (1H, d), 4.62 (1H, d), 4.87 (1H, d), 4.92 (2H, s), 6.75 (2H, d), 7.04 (2H, d), 7.08-7.34 (20H, m) 8.36 (1H, s), 8.48 (1H, s). |
| 100 | 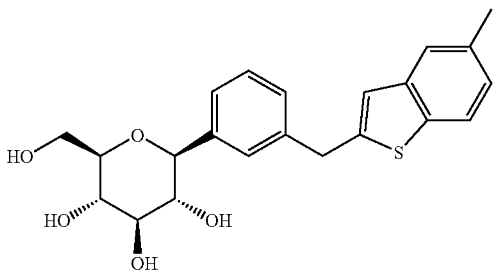 | ¹H-NMR (CD₃OD); 2.44 (3H, s), 3.35-3.49 (4H, m), 3.59-3.71 (1H, m), 3.86-3.89 (1H, m), 4.18 (1H, d), 4.21 (2H, s), 6.97 (1H, s), 7.05-7.08 (1H, m), 7.22-7.32 (3H, m), 7.39 (1H, brs), 7.46 (1H, brs), 7.58 (1H, d) FAB-MS (m/z); 399 [M − H]⁻ |
| 101 | 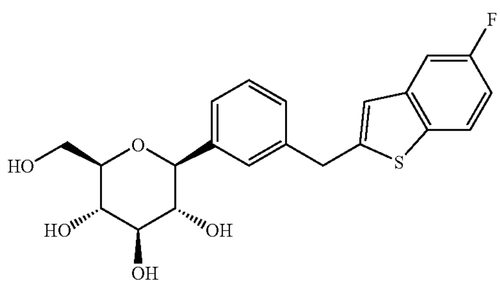 | ¹H-NMR (CD₃OD); 3.34-3.49 (4H, m), 3.59-3.71 (1H, m), 3.86-3.89 (1H, m), 4.12 (1H, d), 4.23 (2H, s), 6.99-7.05 (2H, m), 7.23-7.40 (5H, m), 7.70 (1H, m) FAB-MS (m/z); 403 [M − H]⁻ |
| 102 | 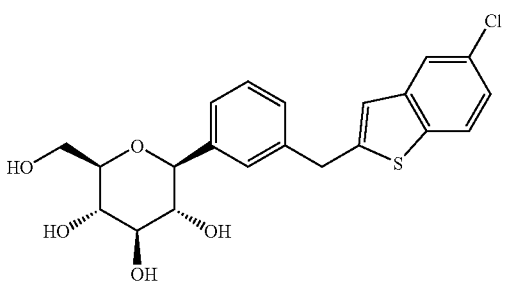 | ¹H-NMR (CD₃OD); 7.69 (1H, d), 7.66 (1H, d), 7.40 (1H, s), 7.20-7.36 (4H, m), 7.05 (1H, s), 4.24 (2H, s), 4.13 (1H, d), 3.86 (1H, dd), 3.70 (1H, dd); 3.33-3.50 (4H, m) FAB-MS (m/z); 420 [M]⁺ |
| 103 | 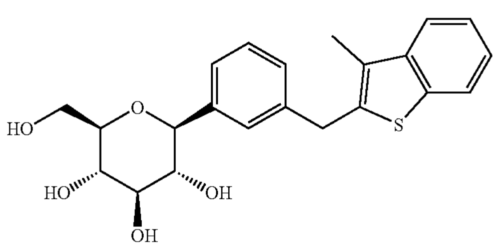 | ¹H-NMR (CD₃OD); 7.71 (1H, d), 7.65 (1H, d), 7.15-7.35 (6H, m), 4.22 (2H, s), 4.10 (1H, d), 3.88 (1H, dd), 3.68 (1H, m), 3.32-3.49 (4H, m), 2.37 (3H, s) FAB-MS (m/z); 400 [M]⁺ |
| 104 | 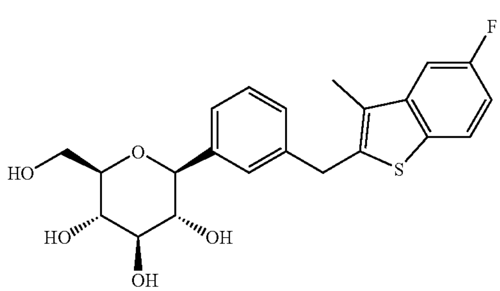 | ¹H-NMR (CD₃OD); 2.34 (3H, s), 3.32-3.46 (4H, m), 3.66-3.70 (1H, m), 3.87 (1H, dd), 4.10 (1H, d), 4.22 (2H, s), 7.01-7.06 (1H, m), 7.16-7.19 (1H, m), 7.27-7.37 (4H, m), 7.70 (1H, dd), FAB-MS (m/z); 417 [M − H]⁻ |

TABLE 23-continued

| Ex. | STRUCTURE | DATA |
| --- | --- | --- |
| 105 | (structure with Cl and methyl substituents on benzothiophene) | $^1$H-NMR (CD$_3$OD); 2.36 (3H, s), 3.33-3.49 (4H, m), 3.66-3.70 (1H, m), 3.86-3.89 (1H, m), 4.10 (1H, d) 4.22 (2H, s), 7.17-7.19 (1H, m), 7.24 (1H, dd), 7.27-7.31 (2H, m), 7.34 (1H, brs), 7.65 (1H, d), 7.69 (1H, d) FAB-MS (m/z); 433 [M − H]$^-$ |

TABLE 24

| Ex. | STRUCTURE | DATA |
| --- | --- | --- |
| 106 | (structure with t-Bu substituent) | $^1$H-NMR (CD$_3$OD); 1.36 (9H, s), 3.35-3.49 (4H, m), 3.67-3.71 (1H, m), 3.86-3.71 (1H, s), 4.12 (1H, d), 4.21 (2H, s), 7.02 (1H, m), 7.15-7.31 (3H, m), 7.33 (1H, dd), 7.39 (1H, brs), 7.62 (1H, d), 7.67 (1H, d) FAB-MS (m/z); 442 [M]$^+$ |
| 107 | (structure with OMe substituent) | $^1$H-NMR (CD$_3$OD); 3.35-3.47 (4H, m), 3.67-3.71 (1H, m), 3.81 (3H, s), 3.86-3.89 (1H, m), 4.12 (1H, d), 4.21 (2H, s), 6.86 (1H, d), 6.99 (1H, s), 7.18 (1H, d), 7.23-7.31 (3H, m), 7.39 (1H, s), 7.56 (1H, d) FAB-MS (m/z); 415[M − H]$^-$ |
| 108 | (structure with NMe$_2$ substituent) | $^1$H-NMR (CD$_3$OD); 2.94 (6H, s), 3.35-3.49 (4H, m), 3.67-3.71 (1H, m), 3.86-3.89 (1H, m), 4.12 (1H, d), 4.19 (2H, s), 6.92 (1H, dd), 6.95 (1H, s), 7.10 (1H, d), 7.17-7.31 (3H, m), 7.39 (1H, brs) 7.54 (1H, d) FAB-MS (m/z); 430 [M + H]$^+$ |
| 109 | (structure with NEt$_2$ substituent) | $^1$H-NMR (CD$_3$OD); 1.13 (6H, t), 3.36 (4H, q), 3.39-3.41 (4H, m), 3.67-3.71 (1H, m), 3.86-3.89 (1H, m), 4.12 (1H, d), 4.18 (2H, s), 6.84 (1H, m) 6.91 (1H, s), 7.02 (1H, s), 7.22-7.30 (3H, m), 7.39 (1H, s), 7.51 (1H, d) FAB-MS (m/z); 458 [M + H]$^+$ |

TABLE 24-continued

| Ex. | STRUCTURE | DATA |
|---|---|---|
| 110 | 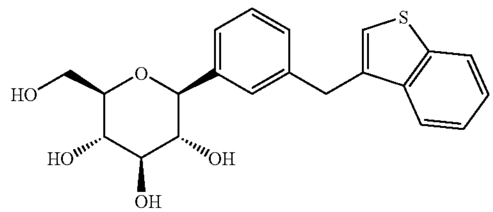 | $^1$H-NMR (CD$_3$OD); 7.84 (1H, m), 7.74 (1H, m), 7.39 (1H, s), 7.14-7.34 (6H, m), 4.24 (2H, s), 4.10 (1H, d); 3.87 (1H, dd), 3.69 (1H, dd), 3.30-3.50 (4H, m)<br>FAB-MS (m/z); 386 [M]$^+$ |
| 111 | 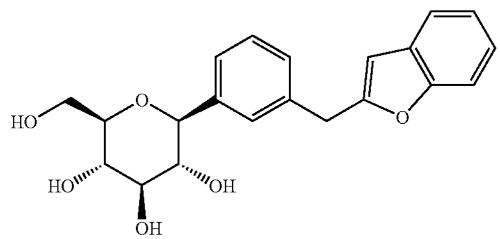 | $^1$H-NMR (CD$_3$OD); 3.35-3.50 (4H, m), 3.67-3.71 (1H, m), 3.86-3.89 (1H, m), 4.10 (2H, s), 4.13 (1H, d), 6.44 (1H, s), 7.13-7.18 (2H, m), 7.26-7.36 (4H, m), 7.41 (1H, brs), 7.45-7.47 (1H, m)<br>FAB-MS (m/z) 369[M − H]$^-$ |
| 112 | 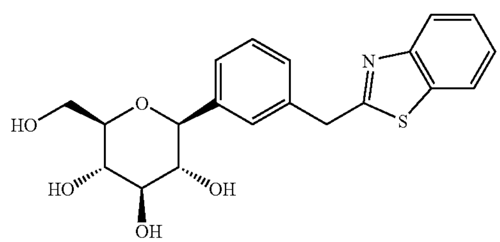 | $^1$H-NMR (CD$_3$OD); 3.35-3.50 (4H, m), 3.67-3.72 (1H, m), 3.88 (1H, dd), 4.14 (1H, d), 4.49 (2H, s), 7.32-7.43 (4H, m), 7.48-7.53 (2H, m), 7.91-7.93 (2H, m).<br>FAB-MS (m/z); 388 [M + H]$^+$ |

TABLE 25

| Ex. | STRUCTURE | DATA |
|---|---|---|
| 113 | 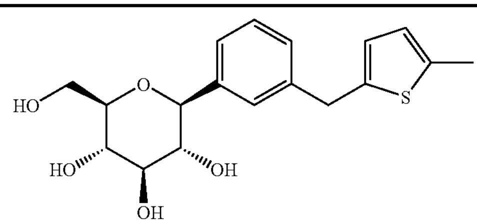 | $^1$H-NMR (CD$_3$OD); 2.42 (3H, s), 3.34-3.94 (6H, m), 4.09 (2H, s), 4.16 (1H, d), 6.57-6.62 (2H, m), 7.20-7.36 (4H, m)<br>ES-MS(m/z); 373[M + Na]$^+$ |
| 114 | 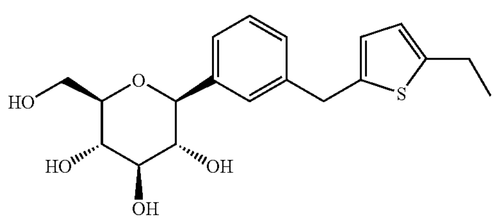 | $^1$H-NMR (CD$_3$OD); 1.27 (3H, t), 2.79 (2H, dd), 3.39-3.52 (4H, m), 3.74-3.94 (2H, m), 4.10 (2H, s), 4.17 (1H, d), 6.62 (2H, dd), 7.20-7.37 (4H, m)<br>ES-MS (m/z); 382 [M + NH$_4$]$^+$ |
| 115 | 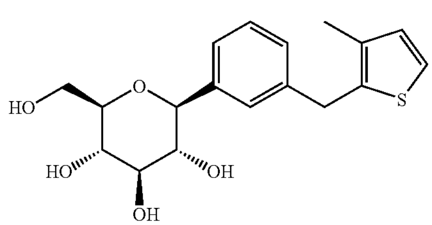 | $^1$H-NMR (CD$_3$OD); 2.21 (3H, s), 3.35-3.52 (4H, m), 3.73-3.94 (2H, m), 4.11 (2H, s), 4.15 (1H, d), 6.84 (1H, d), 7.10 (1H, d), 7.14-7.33 (4H, m)<br>ES-MS (m/z); 368 [M + NH$_4$]$^+$ |

TABLE 25-continued

| Ex. | STRUCTURE | DATA |
| --- | --- | --- |
| 116 | 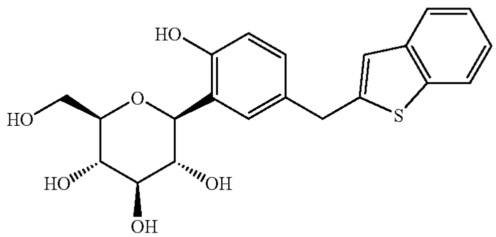 | ¹H-NMR (CD₃OD); 3.39-3.43 (2H, m), 3.44-3.58 (2H, m), 3.67-3.73 (2H, m), 3.86 (1H, m), 4.14 (2H, s), 4.57 (1H, d), 6.78 (1H, d), 7.02 (1H, s), 7.08 (1H, dd), 7.24 (1H, m), 7.31 (1H, d), 7.64 (1H, d), 7.71 (1H, d)<br>EI-MS (m/z); 402 [M]⁺ |
| 117 | 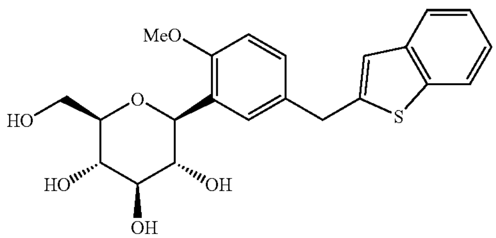 | ¹H-NMR (CD₃OD); 3.36-3.39 (2H, m), 3.46-3.54 (2H, m), 3.63-3.68 (1H, m), 3.81-3.86 (4H, m), 4.12 (2H, s), 4.69 (1H, d), 6.94 (1H, d), 7.04 (1H, s), 7.20-7.28 (3H, m), 7.39 (1H, d), 7.64 (1H, d), 7.71 (1H, d).<br>FAB-MS (m/z); 416 [(M + H)⁺] |
| 118 | 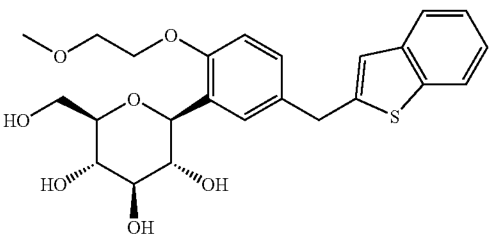 | ¹H-NMR (CD₃OD); 3.38-3.56 (7H, m), 3.64-3.68 (1H, m), 3.74-3.76 (2H, m), 3.82 (1H, d), 4.17 (2H, t), 4.19 (2H, s), 4.70 (1H, d), 6.94 (1H, d), 7.04 (1H, s), 7.19-7.28 (3H, m), 7.40 (1H, d), 7.65 (1H, d), 7.71 (1H, d).<br>FAB-MS (m/z); 483 (M + Na]⁺ |
| 119 | 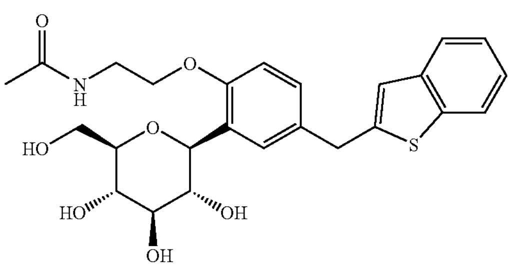 | ¹H-NMR (CD₃OD); 1.96 (3H, s), 3.39-3.41 (2H, m), 3.46-3.52 (3H, m), 3.59-3.70 (2H, m), 3.86 (1H, d), 4.01-4.14 (2H, m), 4.17 (2H, s), 4.72 (1H, d), 6.92 (1H, d), 7.04 (1H, d), 7.18-7.29 (3H, m), 7.42 (1H, d), 7.64 (1H, d), 7.71 (1H, dd).<br>FAB-MS (m/z); 488 [M + H]⁺ |

TABLE 26

| Ex. | STRUCTURE | DATA |
| --- | --- | --- |
| 120 | 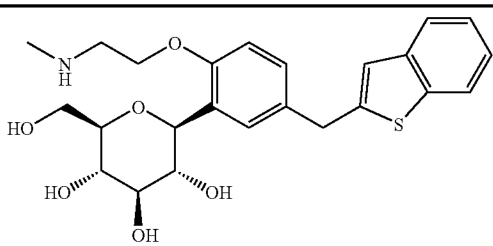 | ¹H-NMR (CD₃OD); 2.43 (3H, s), 2.88-2.99 (2H, m), 3.37-3.39 (2H, m), 3.45-3.55 (2H, m), 3.64-3.68 (1H, m), 3.85 (1H, dd), 4.09-4.15 (2H, m), 4.18 (2H, s), 4.67 (1H, d), 6.94 (1H, d), 7.04 (1H, s), 7.19-7.29 (3H, m), 7.40 (1H, d), 7.65 (1H, d), 7.71 (1H, d).<br>EI-MS (m/z); 460 [M + H]⁺ |
| 121 | 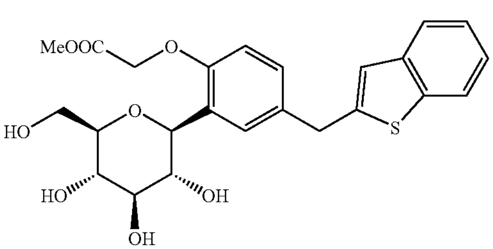 | ¹H-NMR (CD₃OD); 3.59-3.42 (2H, m), 3.47-3.57 (2H, m), 3.66 (1H, m), 3.78 (3H, s), 3.85 (1H, d), 4.18 (2H, s), 4.72-4.74 (2H, m), 6.87 (1H, d), 7.04 (1H, s), 7.18-7.30 (3H, m), 7.44 (1H, d), 7.65 (1H, d), 7.72 (1H, m)<br>FAB-MS (m/z); 475 [M + H] |

TABLE 26-continued

| Ex. | STRUCTURE | DATA |
| --- | --- | --- |
| 122 | 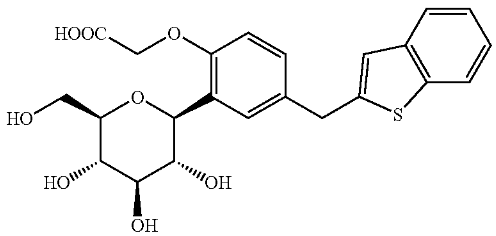 | ¹H-NMR (CD₃OD); 3.39-3.43 (2H, m), 3.50-3.54 (2H, m), 3.67 (1H, m), 3.86 (1H, d), 4.18 (2H, s), 4.56-4.70 (2H, m), 4.78 (1H, m), 6.87 (1H, d), 7.03 (1H, s), 7.17-7.30 (3H, m), 7.44 (1H, d), 7.64 (1H, d), 7.72 (1H, d)<br>FAB-MS (m/z); 459 [M − H]⁻ |
| 123 | 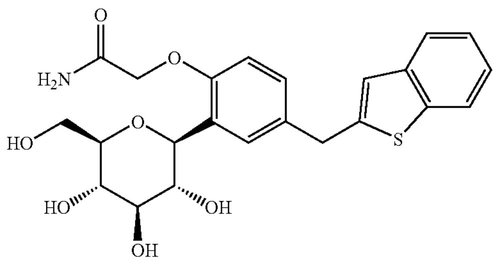 | ¹H-NMR (CD₃OD); 3.39-3.43 (2H, m), 3.48-3.53 (2H, m), 3.68 (1H, m), 3.86 (1H, d), 4.19 (2H, s), 4.48-4.63 (2H, m), 4.69 (1H, d, J = 9.3 Hz), 6.89 (1H, d), 7.04 (1H, s), 7.13-7.30 (3H, m), 7.45 (1H, d), 7.65 (1H, d), 7.71 (1H, d)<br>FAB-MS (m/z); 458 [M − H]⁻ |
| 124 | 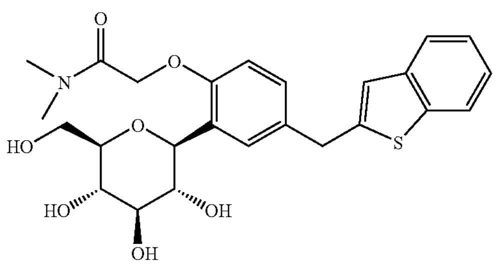 | ¹H-NMR (CD₃OD); 2.97 (3H, s), 3.07 (3H, s), 3.36-3.43 (2H, m), 3.46-3.54 (2H, m), 3.62-3.68 (1H, m), 3.84 (1H, d), 4.18 (2H, s), 4.73-4.87 (3H, m), 6.91 (1H, d), 7.04 (1H, s), 7.15-7.29 (3H, m), 7.44 (1H, d), 7.64 (1H, d), 7.71 (1H, dd)<br>FAB-MS (m/z); 488 [M + H]⁺ |
| 125 | 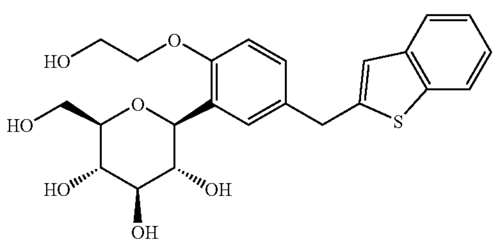 | ¹H-NMR (CD₃OD); 3.38-3.42 (2H, m), 3.47-3.52 (2H, m), 3.67 (1H, m), 3.82-3.94 (3H, m), 4.03-4.12 (2H, m), 4.17 (2H, s), 4.76 (1H, m), 6.94 (1H, d), 7.04 (1H, s), 7.17-7.28 (3H, m), 7.42 (1H, d), 7.65 (1H, d), 7.71 (1H, d)<br>FAB-MS (m/z); 447 [M + H]⁺ |
| 126 | 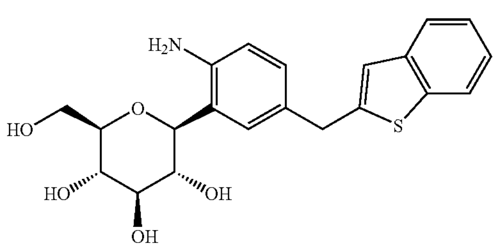 | ¹H-NMR (CD₃OD); 3.38-3.50 (3H, m), 3.62-3.74 (2H, m), 3.87-3.90 (1H, m), 4.13 (2H, s), 4.33 (1H, d), 6.82 (1H, d), 7.02 (1H, s), 7.05-7.08 (1H, m), 7.19-7.28 (3H, m), 2.78 (3H, s), 7.64 (1H, d), 7.70 (1H, d)<br>FAB-MS (m/z); 402 [M + H]⁺ |

TABLE 27

| Ex. | STRUCTURE | DATA |
|---|---|---|
| 127 | 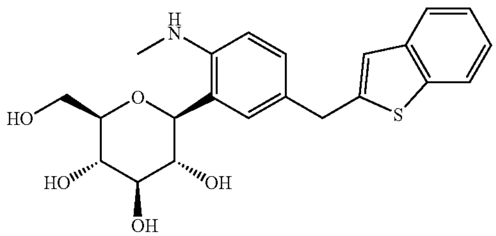 | ¹H-NMR (CD₃OD); 2.78 (3H, s), 3.36-3.51 (3H, m), 3.68-3.76 (2H, m), 3.85-3.88 (1H, m), 4.11 (2H, s), 4.26 (1H, d), 6.65 (1H, d), 7.00 (1H, s), 7.12 (1H, dd), 7.17-7.27 (3H, m), 7.62 (1H, d), 7.69 (1H, d)<br>FAB-MS (m/z); 416 [M + H]⁺ |
| 128 | 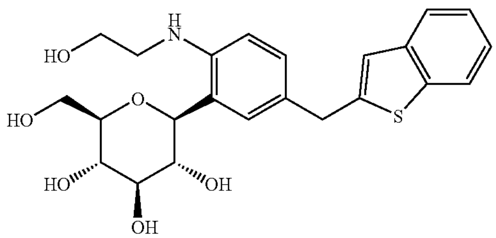 | ¹H-NMR (CD₃OD); 3.15-3.20 (2H, m), 3.36-3.40 (1H, m), 3.45-3.47 (2H, m), 3.69-3.83 (6H, m), 3.87 (1H, dd), 4.10 (2H, s), 4.26 (1H, d), 6.67 (1H, d), 7.00 (1H, s), 7.10 (1H, dd), 7.13 (1H, d), 7.19-7.25 (2H, m), 7.63 (1H, d), 7.70 (1H, d)<br>FAB-MS (m/z); 446 [M + H]⁺ |
| 129 | 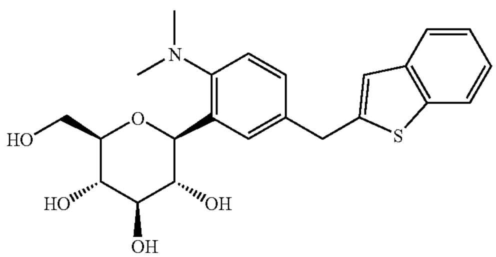 | ¹H-NMR (CD₃OD); 2.76 (6H, s), 3.58-3.40 (4H, m), 3.66 (1H, dd), 3.85 (1H, m), 4.21 (2H, s), 7.06 (1H, s), 7.20-7.29 (4H, m), 7.47 (1H, s), 7.65 (1H, d), 7.71 (1H, d)<br>FAB-MS (m/z); 430 [M + H]⁺ |
| 130 | 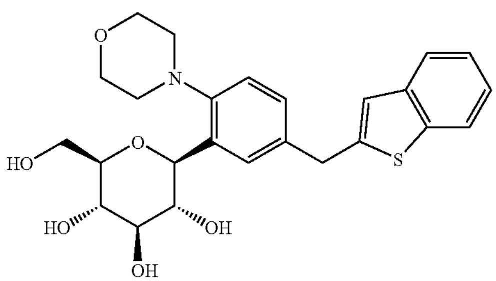 | ¹H-NMR (CD₃OD); 2.89-2.94 (2H, m), 3.02-3.07 (2H, m), 3.36-3.37 (1H, m), 3.56-3.61 (1H, m), 3.70-3.75 (1H, m), 3.78-3.87 (5H, m), 4.21 (2H, s), 4.85 (1H, d), 7.05 (1H, s), 7.17 (1H, d), 7.20-7.29 (3H, m), 7.44 (1H, d), 7.65 (1H, d), 7.72 (1H, d)<br>FAB-MS (m/z); 472 [M + H]⁺ |
| 131 | 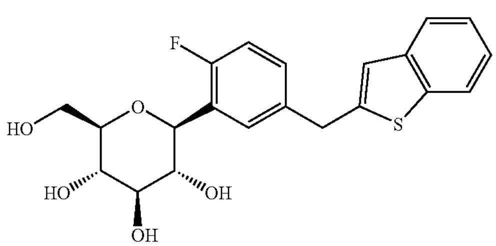 | ¹H-NMR (CD₃OD); 3.34-3.52 (4H, m), 3.66-3.72 (1H, m), 3.87 (1H, d), 4.22 (2H, s), 4.46-4.56 (1H, m), 6.98-7.08 (2H, m), 7.18-7.32 (3H, m), 7.49 (1H, dd), 7.66 (1H, d), 7.72 (1H, d)<br>EI-MS (m/z); 405 [M + H]⁺ |
| 132 | 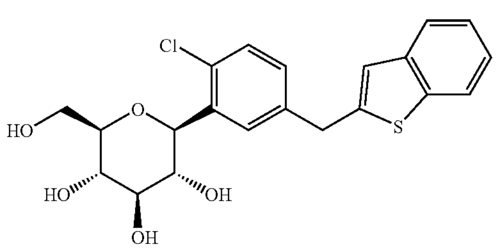 | ¹H-NMR (CD₃OD); 3.41-3.44 (2H, m), 3.49-3.55 (2H, m), 3.66-3.70 (1H, m), 3.86 (1H, d), 4.24 (2H, s), 4.71-4.74 (1H, m), 7.07 (1H, s), 7.21-7.29 (3H, m), 7.34 (1H, d), 7.55 (1H, s), 7.66 (1H, d), 7.73 (1H, d)<br>FAB-MS (m/z); 419 [M − H]⁻ |

TABLE 27-continued

| Ex. | STRUCTURE | DATA |
| --- | --- | --- |
| 133 | 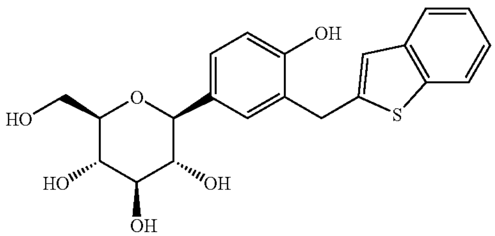 | ¹H-NMR (CD₃OD); 3.33-3.46 (4H, m), 3.62-3.68 (1H, m), 3.84 (1H, dd), 4.02 (1H, d), 4.18 (2H, dd), 6.80 (1H, d) 7.03 (1H, d), 7.11-7.27 (4H, m), 7.62 (1H, m), 7.69 (1H, d) FAB-MS (m/z); 401 [M − H]⁻ |
| 134 | 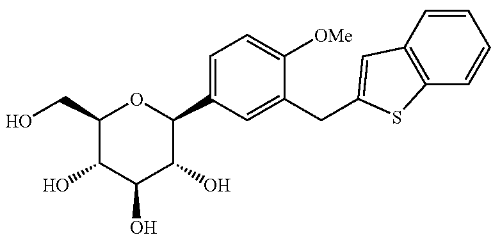 | ¹H-NMR (CD₃OD); 3.34-3.45 (4H, m), 3.65-3.69 (1H, m), 3.85 (3H, s), 4.06 (1H, d), 4.20 (2H, d), 6.96 (1H, d), 7.00 (1H, d), 7.18-7.31 (4H, m), 7.61 (1H, d), 7.69 (1H, d) FAB-MS (m/z); 415 [M − H]⁻ |

TABLE 28

| Ex. | STRUCTURE | DATA |
| --- | --- | --- |
| 135 | 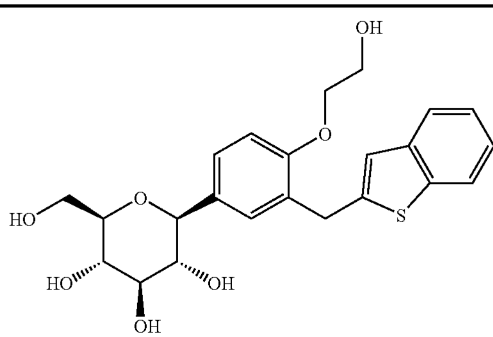 | ¹H-NMR (CD₃OD); 3.33-3.53 (4H, m), 3.60-3.72 (1H, m), 3.80-3.94 (3H, m), 4.02-4.13 (3H, m), 4.27 (2H, dd), 6.96 (1H, d), 7.06 (1H, s), 7.18-7.38 (4H, m), 7.63 (1H, d), 7.70 (1H, d) FAB-MS (m/z); 446 [M + H]⁺ |
| 136 | 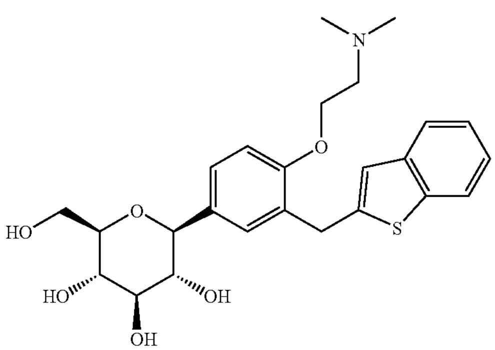 | ¹H-NMR (CD₃OD); 2.21 (6H, s), 2.70 (2H, t), 3.23-3.40 (4H, m), 3.52-3.63 (1H, m), 3.76 (1H, d), 3.94-4.22 (5H, m), 6.87 (2H, d), 7.05-7.27 (4H, m), 7.47-753 (1H, m), 7.56-7.63 (1H, m) FAB-MS (m/z); 474 [M + H]⁺ |
| 137 | 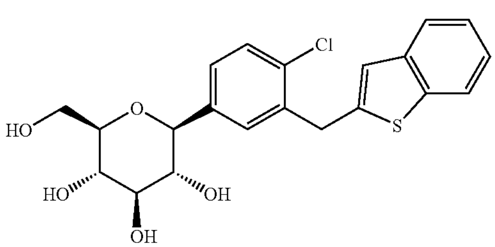 | ¹H-NMR (CD₃OD); 3.26-3.52 (4H, m), 3.69 (1H, dd), 3.87 (1H, d), 4.12 (1H, d), 4.36 (2H, dd), 7.20-7.29 (m, 2H), 7.34 (1H, dd), 7.40 (1H, d), 7.48 (1H, d), 7.64 (1H, d), 7.73 (1H, d) FAB-MS (m/z); 420 [M + H]⁺ |

TABLE 28-continued

| Ex. | STRUCTURE | DATA |
| --- | --- | --- |
| 138 | 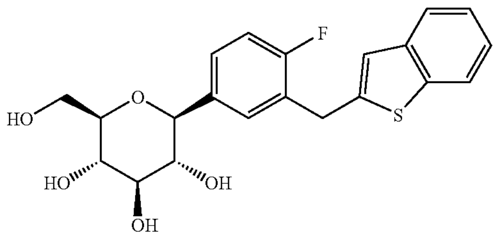 | ¹H-NMR (CD₃OD); 3.38-3.49 (3H, m), 3.68 (1H, dd), 3.87 (1H, d), 4.11 (1H, d); 4.23 (2H, d), 7.05-7.08 (2H, m), 7.21-7.30 (1H, m), 7.33-7.38 (1H, m), 7.43 (1H, d); 7.66 (1H, d); 7.72 (1H, d) FAB-MS (m/z); 404 [M⁺] |
| 139 | 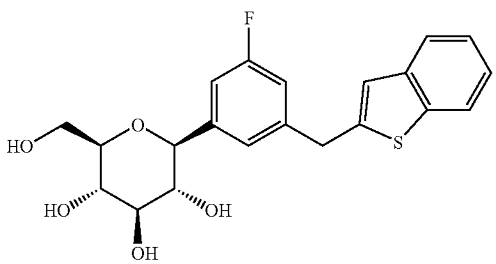 | ¹H-NMR (CD₃OD); 3.33-3.53 (3H, m), 3.70 (1H, dd), 3.88 (1H, dd), 4.13 (1H, d), 4.25 (2H, s), 6.94-6.99 (1H, m), 7.05-7.11 (2H, m), 7.20-7.32 (3H, m), 7.67 (1H, d), 7.73 (1H, d) ES-MS (m/z) 427 [M + Na]⁺ |
| 140 | 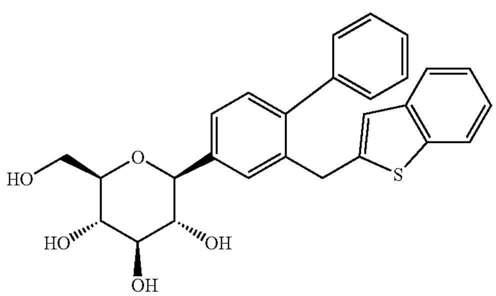 | ¹H-NMR (CD₃OD); 3.36-3.54 (4H, m), 3.64-3.76 (1H, m), 3.89 (1H, d) 4.12-4.22 (3H, m), 6.78 (1H, s), 7.16-7.52 (10H, m), 7.58 (1H, d), 7.78 (1H, d) FAB-MS (m/z); 461 [M − H]⁻ |

TABLE 29

| Ex. | STRUCTURE | DATA |
| --- | --- | --- |
| 141 | 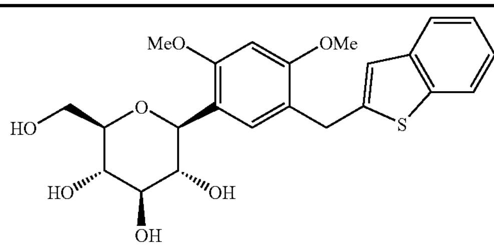 | ¹H-NMR (CD₃OD); 3.24-3.30 (2H, m), 3.36 (1H, t), 3.43 (1H, t), 3.51-3.57 (1H, m), 3.73 (1H, dd), 3.75 (3H, s), 3.78 (3H, s), 4.00 (1H, d), 4.05 (1H, d), 4.51 (1H, d), 6.53 (1H, s), 6.87 (1H, d), 7.08 (1H, ddd), 7.14 (1H, ddd), 7.19 (1H, s), 7.51 (1H, d), 7.58 (1H, dd) ES-MS (m/z); 469 [M + Na]⁺ |
| 142 | 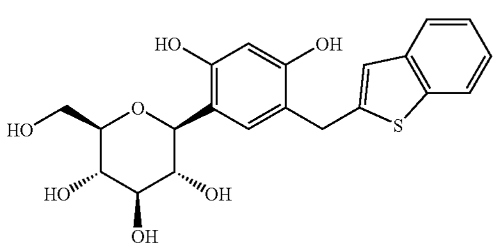 | ¹H-NMR (CD₃OD); 3.24-3.39 (3H, m), 3.45 (1H, t), 3.58 (1H, dd), 3.74 (1H, dd), 3.97 (1H, d), 4.03 (1H, d), 4.35 (1H, d), 6.28 (1H, s), 6.89 (1H, s), 7.02 (1H, s), 7.06-7.17 (2H, m), 7.51 (1H, d), 7.59 (1H, dd) FAB-MS (m/z); 419 [M + H]⁺ |

TABLE 29-continued

| Ex. | STRUCTURE | DATA |
|---|---|---|
| 143 | 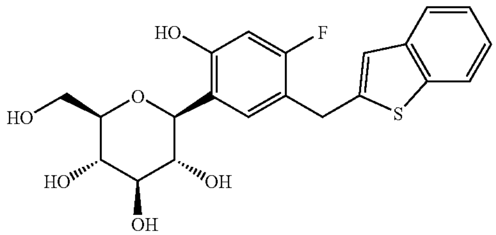 | $^1$H-NMR (CD$_3$OD); 3.35-3.56 (4H, m), 3.69 (1H, dd), 3.85 (1H, d), 4.09-4.21 (2H, m), 4.55 (1H, d), 6.57 (1H, d), 7.01 (1H, s), 7.18-7.30 (2H, m), 7.33 (1H, d), 7.64 (1H, d), 7.71 (1H, d, J = 7.8 Hz) EI-MS (m/z); 420 [M]$^+$ |
| 144 | 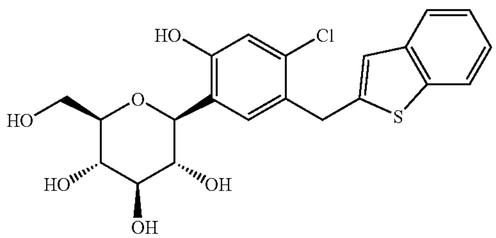 | $^1$H-NMR (CD$_3$OD); 3.37-3.53 (4H, m), 3.66-3.73 (1H, m), 3.82-3.89 (1H, m), 4.26 (2H, dd), 4.56 (1H, d), 6.88 (1H, s), 6.98 (1H, s), 7.18-7.29 (2H, m), 7.40 (1H, s), 7.63 (1H, d), 7.72 (1H, d) EI-MS (m/z); 458 [M + Na]$^+$ |
| 145 | 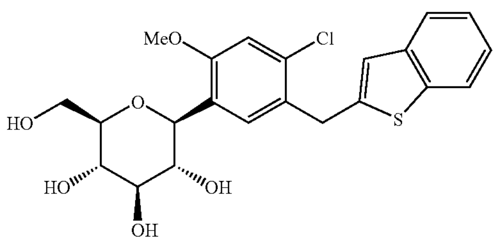 | $^1$H-NMR (CD$_3$OD); 3.35-3.39 (2H, m), 3.44-3.48 (2H, m), 3.62-3.69 (1H, m), 3.83 (3H, s), 3.84-3.86 (1H, m), 4.29 (2H, dd), 4.61-4.68 (1H, m), 6.99 (1H, s), 7.04 (1H, s), 7.18-7.29 (2H, m), 7.48 (1H, s), 7.63 (1H, d), 7.72 (1H, d) FAB-MS (m/z); 449 [M − H]$^-$ |
| 146 | 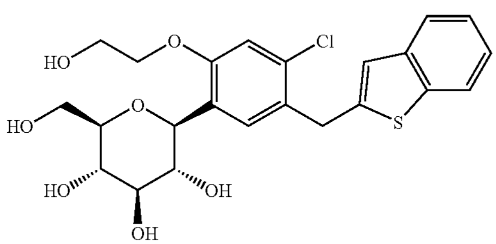 | $^1$H-NMR (CD$_3$OD); 3.37-3.51 (4H, m), 3.62-3.69 (1H, m), 3.81-3.90 (3H, m), 4.10 (2H, dd), 4.30 (2H, dd), 4.72 (1H, d), 7.00 (1H, s), 7.07 (1H, s), 7.19-7.29 (2H, m), 7.5 (1H, s), 7.64 (1H, d), 7.72 (1H, d) EI-MS (m/z); 503 [M + Na]$^+$ |
| 147 | 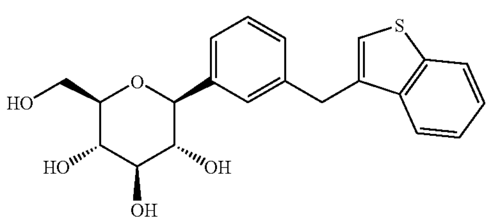 | $^1$H-NMR (CD$_3$OD); 3.30-3.50 (4H, m), 3.69 (1H, dd), 3.87 (1H, dd), 4.10 (1H, d), 4.24 (2H, s), 7.14-7.34 (6H, m), 7.39 (1H, s), 7.74 (1H, m), 7.84 (1H, m) FAB-MS (m/z); 386 [M]$^+$ |
| 148 | 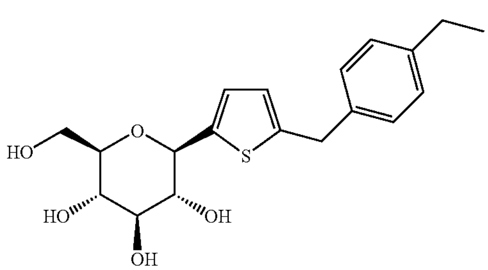 | $^1$H-NMR (CD$_3$OD); 2.61-2.97 (5H, m), 3.54-3.79 (6H, m), 4.07 (1H, d), 4.17-4.95 (4H, m), 7.03-7.24 (7H, m), 7.51 (1H, s) EI-MS (m/z); 370 [M]$^+$ |

TABLE 30

| Ex. | STRUCTURE | DATA |
|---|---|---|
| 149 | 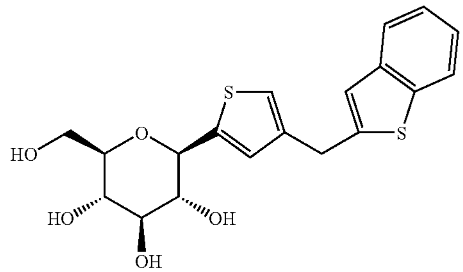 | ¹H-NMR (CD₃OD); 2.61-2.97 (5H, m), 3.54-3.79 (6H, m), 4.07 (1H, d), 3.33-3.52 (4H, m), 3.65 (1H, dd), 3.87 (1H, dd), 4.16-4.22 (2H, m), 4.37 (1H, d), 7.00-7.33 (5H, m), 7.60-7.76 (2H, m) FAB-MS (m/z); 392 [M]⁺ |
| 150 | 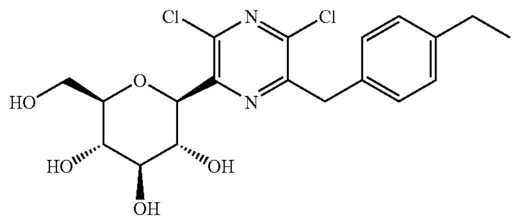 | ¹H-NMR (CD₃OD); 1.19 (3H, t), 2.59 (2H, q), 3.39-3.50 (2H, m), 3.56 (1H, t), 3.66 (1H, dd), 3.88 (1H, dd), 4.01 (1H, t), 4.28 (2H, s), 4.75 (1H, d), 7.12 (2H, d), 7.18 (2H, d). FAB-MS (m/z); 429 [M + H]⁺ |
| 151 | 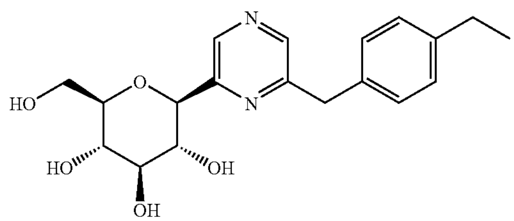 | ¹H-NMR (CD₃OD); 1.20 (3H, t), 2.60 (2H, q), 3.45-3.56 (3H, m), 3.64 (1H, t), 3.70-3.75 (1H, m), 3.89 (1H, dd), 4.17 (2H, s), 4.37 (1H, d), 7.13 (2H, d), 7.19 (2H, d), 8.40 (1H, s), 8.56 (1H, s). EI-MS (m/z); 361 [M + H]⁺ |
| 152 | 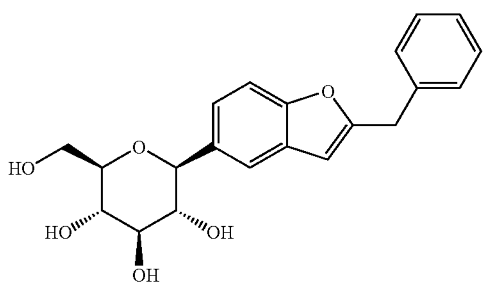 | ¹H-NMR (CD₃OD); 3.39-3.51 (4H, m), 3.70 (1H, dd), 3.88 (1H, dd), 4.09 (2H, s), 4.19 (1H, d), 6.43 (1H, s), 7.20-7.35 (7H, m), 7.54 (1H, d). EI-MS (m/z); 393 [M + Na]⁺ |
| 153 | 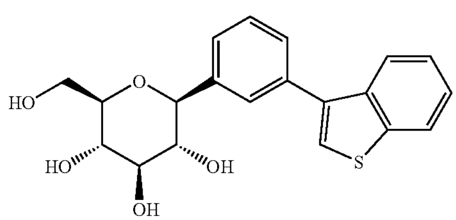 | ¹H-NMR (CD₃OD); 3.40-3.59 (4H, m), 3.66-3.76 (1H, m), 3.90 (1H, dd), 4.24 (1H, d), 7.36-7.42 (2H, m), 7.44-7.57 (4H, m), 7.67 (1H, brs), 7.89-7.96 (2H, m) FAB-MS (m/z); 372 [M + H]⁺ |
| 154 | 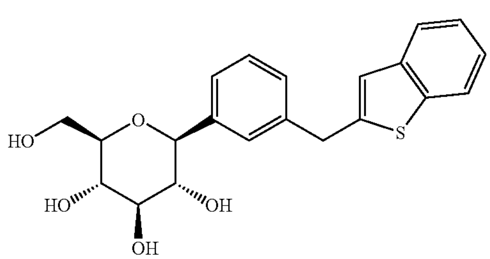 | ¹H-NMR (CD₃OD); 3.34-3.49 (4H, m), 3.67 (1H, m), 3.87 (1H, d), 4.12 (1H, d), 4.24 (2H, s), 7.06 (1H, s), 7.06-7.33 (5H, m), 7.40 (1H, s), 7.65 (1H, d), 7.72 (1H, d) FAB-MS (m/z); 385 [M − H]⁻ |

TABLE 30-continued

| Ex. | STRUCTURE | DATA |
| --- | --- | --- |
| 155 | 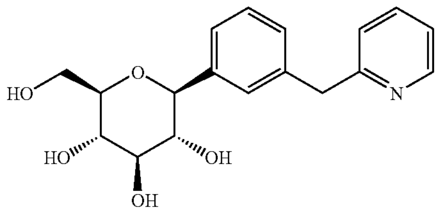 | ¹H-NMR (CD₃OD); 3.23-3.49 (4H, m), 3.69 (1H, dd), 3.87 (1H, m), 4.10 (1H, d), 4.14 (2H, s), 7.15 (1H, m), 7.18-7.31 (4H, m), 7.36 (1H, s), 7.73 (1H, dt), 8.42 (1H, m) FAB-MS (m/z); 332 [M + H]⁺ |

TABLE 31

| Ex. | STRUCTURE | DATA |
| --- | --- | --- |
| 156 | 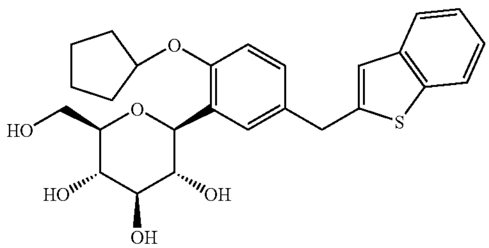 | ¹H-NMR (CD₃OD); 1.61-1.65 (2H, m), 1.79-1.90 (6H, m), 3.34-3.40 (2H, m), 3.44-3.48 (1H, m), 3.61-3.66 (2H, m), 3.83 (1H, dd), 4.17 (2H, s), 4.60 (1H, d), 4.80-4.85 (1H, m), 6.93 (1H, d), 7.04 (1H, d), 7.17-7.29 (3H, m), 7.36 (1H, d), 7.65 (1H, d), 7.70-7.72 (1H, m). EI-MS (m/z); 471 [M + H]⁺ |
| 157 | 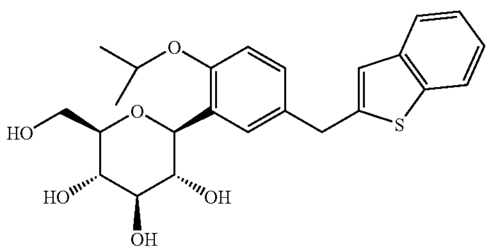 | ¹H-NMR (CD₃OD); 1.33 (6H, t), 3.36-3.39 (2H, m), 3.46-3.50 (1H, m), 3.57-3.67 (2H, m), 3.84 (1H, dd), 4.17 (2H, s), 4.54-4.61 (1H, m), 4.67 (1H, d), 6.94 (1H, d), 7.05 (1H, d), 7.17-7.29 (3H, m), 7.38 (1H, d), 7.65 (1H, d), 7.71 (1H, dd). EI-MS (m/z); 445 [M + H]⁺ |
| 158 | 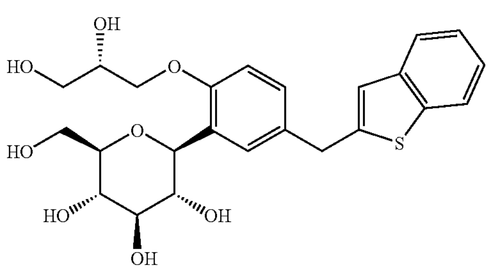 | ¹H-NMR (CD₃OD); 3.38-3.42 (2H, m), 3.45-3.54 (2H, m), 3.64-3.74 (3H, m), 3.87 (1H, dd), 3.93-3.98 (1H, m), 4.03-4.12 (2H, m), 4.18 (2H, s), 4.72 (1H, d), 6.96 (1H, d), 7.04 (1H, s), 7.19-7.22 (1H, m), 7.24 (1H, dd), 7.28 (1H, dd), 7.40 (1H, d), 7.65 (1H, d), 7.71 (1H, d). EI-MS (m/z); 477 [M + H]⁺ |
| 159 | 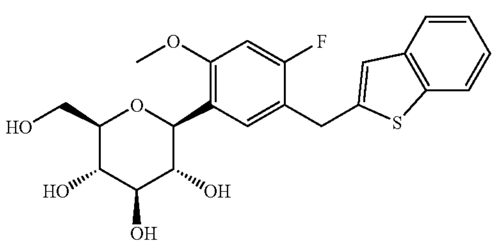 | ¹H-NMR (CD₃OD); 3.33-3.42 (2H, m), 3.43-3.52 (2H, m), 3.61-3.68 (1H, m), 3.80-3.86 (4H, m), 4.12-4.24 (2H, m), 4.63 (1H, d), 6.79 (1H, d), 7.02 (1H, s), 7.18-7.30 (2H, m), 7.41 (1H, d), 7.64 (1H, d), 7.72 (1H, dd) EI-MS (m/z); 457 [M + Na]⁺ |
| 160 | 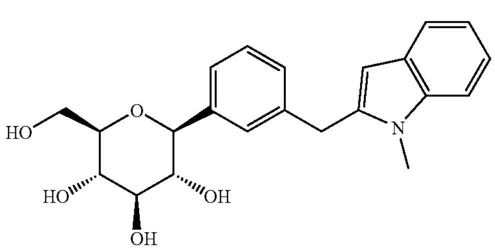 | ¹H-NMR (CD₃OD); 3.32-3.48 (4H, m), 3.57 (3H, s), 3.67 (1H, m), 3.86 (1H, m), 4.09 (1H, d, J = 9.3 Hz), 4.17 (2H, s), 6.22 (1H, s), 6.97 (1H, m), 7.08 (1H, m), 7.14 (1H, m), 7.24-7.32 (4H, m), 7.43 (1H, d). EI-MS (m/z); 382 [M − H]⁻ |

TABLE 31-continued

| Ex. | STRUCTURE | DATA |
|---|---|---|
| 161 | 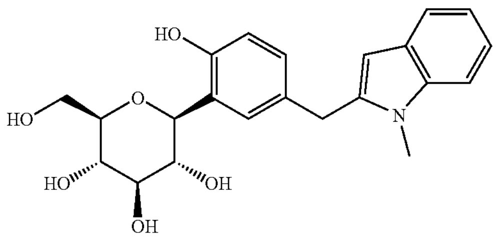 | ¹H-NMR (CD₃OD); 3.38-3.55 (4H, m), 3.56 (3H, s), 3.69 (1H, m), 3.86 (1H, m), 4.06 (2H, s), 4.54 (1H, d, J = 9.2 Hz), 6.17 (1H, s), 6.75 (1H, d), 6.92-7.00 (2H, m), 7.06 (1H, m), 7.20-7.27 (2H, m), 7.42 (1H, d)<br>EI-MS (m/z); 400 [M + H]⁺ |

TABLE 32

| Ex. | STRUCTURE | DATA |
|---|---|---|
| 162 | 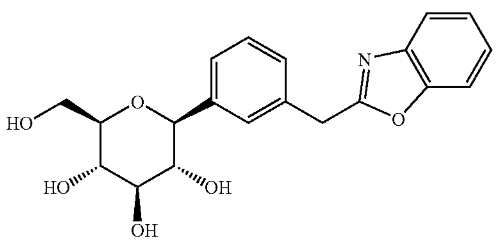 | ¹H-NMR (CD₃OD); 3.44 (2H, m), 3.56 (2H, m), 3.77 (1H, dd), 3.88 (1H, m), 4.17 (1H, d), 4.28 (2H, s), 7.31-7.38 (5H, m), 7.44 (1H, s), 7.50 (1H, m), 7.61 (1H, m)<br>ES-MS (m/z); 372 [M + H]⁺ |
| 163 | 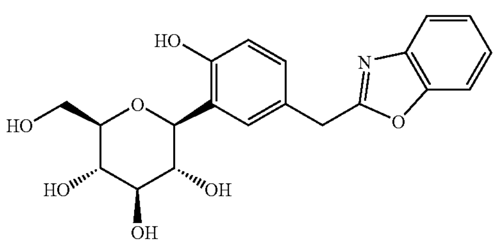 | ¹H-NMR (CD₃OD); 3.46 (1H, m), 3.56 (1H, m), 3.79 (1H, dd), 3.89 (1H, d), 4.20 (2H, s), 4.53 (1H, d), 6.85 (1H, d), 7.17 (1H, d), 7.33 (3H, m), 7.49 (1H, m), 7.61 (1H, m)<br>ES-MS (m/z); 388 [M + H]⁺ |
| 164 | 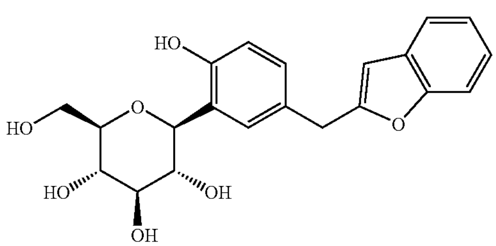 | ¹H-NMR (CD₃OD); 3.38-3.44 (2H, m), 3.45-3.58 (2H, m), 3.70 (1H, m), 3.87 (1H, m), 4.01 (2H, s), 4.58 (1H, d), 6.39 (1H, s), 6.78 (1H, d), 7.06-7.18 (3H, m), 7.30-7.36 (2H, m), 7.44 (1H, m)<br>FAB-MS (m/z); 385 [M − H]⁻ |
| 165 | 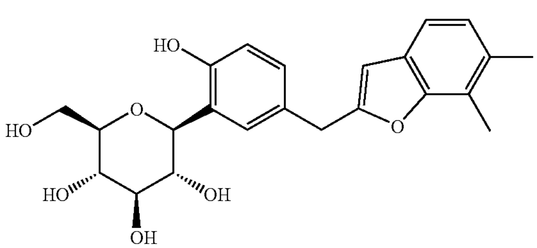 | ¹H-NMR (CD₃OD); 2.35 (3H, s), 2.38 (3H, s), 3.46 (1H, m), 3.56 (3H, m), 3.81 (1H, m), 3.88 (1H, dd), 4.01 (2H, s), 4.51 (1H, d), 6.26 (1H, d), 6.83 (1H, d), 6.96 (1H, d), 7.11 (1H, d), 7.15 (1H, d), 7.25 (1H, s)<br>ES-MS (m/z); 413 [M − H]⁻ |

TABLE 32-continued

| Ex. | STRUCTURE | DATA |
|---|---|---|
| 166 | 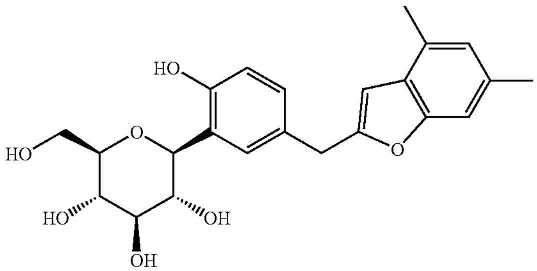 | ¹H-NMR (CD₃OD); 2.39 (3H, s), 2.40 (3H, s), 3.60 (4H, m), 3.82 (1H, m), 3.89 (1H, m), 4.00 (1H, s), 4.51 (1H, d), 6.31 (1H, d), 6.80 (1H, s), 6.83 (1H, dd), 7.01 (1H, s), 7.11 (1H, d), 7.24 (1H, s) ES-MS (m/z); 414 [M]⁺ |
| 167 | 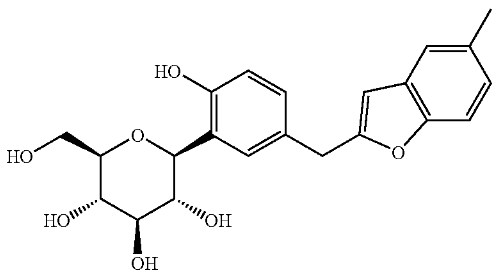 | ¹H-NMR (CD₃OD); 2.40 (3H, s), 3.37-3.58 (4H, m), 3.82 (1H, m), 3.88 (1H, m), 4.00 (2H, s), 4.50 (1H, d), 6.29 (1H, s), 6.83 (1H, d), 6.99 (1H, d), 7.10 (1H, d), 7.23 (1H, m), 7.32 (2H, m) ES-MS (m/z); 399 [M − H]⁻ |

TABLE 33

| Ex. | STRUCTURE | DATA |
|---|---|---|
| 168 | 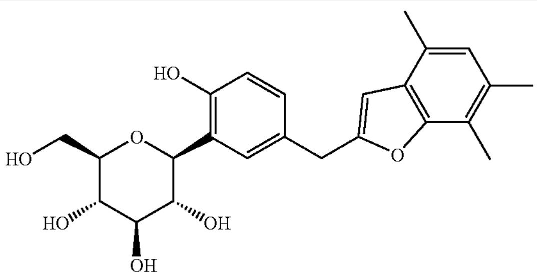 | ¹H-NMR (CD₃OD); 2.31 (3H, s), 2.34 (3H, s), 2.36 (3H, s), 3.45 (1H, m), 3.57 (3H, m), 3.81 (2H, m), 4.01 (2H, s), 4.51 (1H, d), 6.28 (1H, s), 6.78 (1H, s), 6.83 (1H, d), 7.12 (1H, d), 7.26 (1H, s) ES-MS (m/z); 427 [M − H]⁻ |
| 169 | 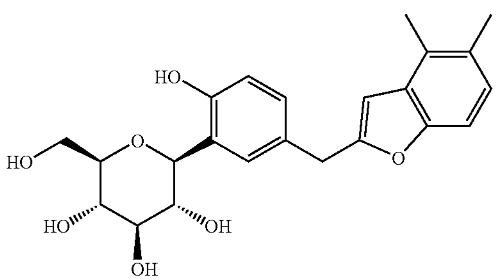 | ¹H-NMR (CD₃OD); 2.31 (3H, s), 2.34 (3H, s), 3.45 (1H, m), 3.58 (3H, m), 3.83 (1H, m), 3.87 (1H, m), 4.01 (2H, s), 4.49 (1H, d), 6.35 (1H, s), 6.84 (1H, d), 6.98 (1H, d), 7.11 (2H, m), 7.21 (1H, s) ES-MS (m/z); 413 [M − H]⁻ |
| 170 | 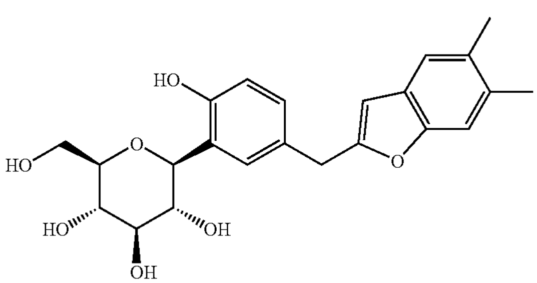 | ¹H-NMR (CD₃OD); 2.29 (3H, s), 2.32 (3H, s), 3.43 (2H, m), 3.58 (2H, m), 3.83 (1H, m), 3.88 (1H, m), 3.99 (2H, s), 4.48 (1H, d), 6.25 (1H, s), 6.83 (1H, d), 7.10 (1H, d), 7.15 (1H, s), 7.20 (2H, s) ES-MS (M/z); 413 [M − H]⁻ |

TABLE 33-continued

| Ex. | STRUCTURE | DATA |
|---|---|---|
| 171 | 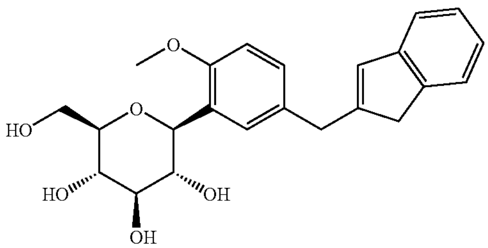 | $^1$H-NMR (CD$_3$OD); 3.26 (2H, s), 3.40 (2H, m), 3.53 (2H, m), 3.67 (1H, dd), 3.76 (2H, s), 3.82 (3H, s), 3.86 (1H, m), 4.70 (1H, d), 6.48 (1H, s), 6.91 (1H, d), 7.01 (1H, m), 7.03-7.22 (3H, m), 7.29 (1H, d), 7.32 (1H, d)<br>ES-MS (m/z); 421 [M + Na]$^+$ |
| 172 | 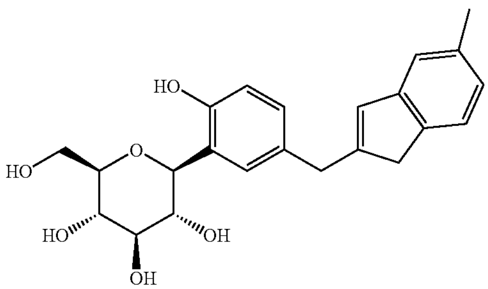 | $^1$H-NMR (CD$_3$OD); 2.31 (3H, s), 3.20 (2H, s), 3.23-3.43 (4H, m), 3.60 (1H, d), 3.68 (2H, s), 3.76 (1H, d), 4.36 (1H, t), 4.47 (1H, d), 4.85 (2H, brs), 4.92 (1H, brs), 6.42 (1H, s), 6.73 (1H, d), 6.84-6.96 (2H, m), 7.03 (1H, s), 7.16 (1H, s), 7.19 (1H, d), 8.74 (1H, brs)<br>ES-MS (m/z); 398 [M]$^+$ |
| 173 | 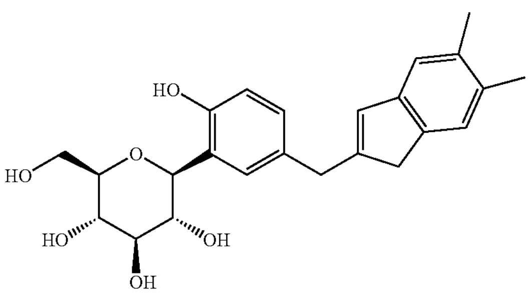 | $^1$H-NMR (CD$_3$OD); 2.23 (6H, s), 3.18 (2H, s), 3.40-3.51 (4H, m), 3.68 (2H, s), 3.70 (1H, d), 3.86 (1H, d), 4.07 (1H, t), 4.50 (1H, d), 4.57 (2H, s), 4.68 (1H, d), 4.91 (1H, d), 6.39 (1H, s), 6.75-6.98 (2H, m), 6.99 (1H, s), 7.08 (1H, s), 7.19 (1H, d), 8.42 (1H, s)<br>ES-MS (m/z); 412 [M]$^+$ |

TABLE 34

| Ex. | STRUCTURE | DATA |
|---|---|---|
| 174 | 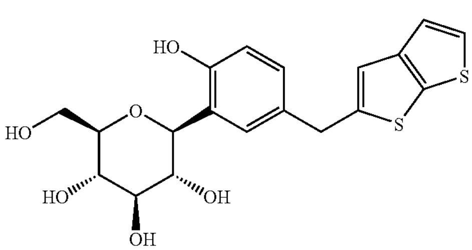 | $^1$H-NMR (CD$_3$OD); 3.25-3.87 (3H, m), 3.67-3.72 (1H, dd), 3.84-3.87 (1H, dd), 4.11 (2H, s), 4.55-4.57 (1H, d), 6.74-6.77 (1H, d), 6.96 (1H, s), 7.04-7.06 (1H, dd), 7.11-7.12 (1H, d), 7.28-7.29 (1H, d), 7.34-7.35 (1H, d)<br>ES-MS (m/z); 431 [M + Na]$^+$ |
| 175 | 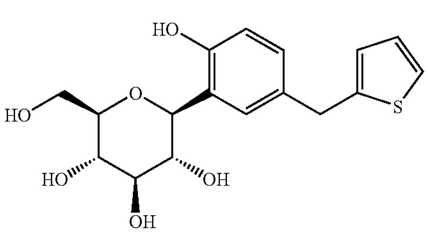 | $^1$H-NMR (CD$_3$OD); 3.27-3.48 (4H, m), 3.61 (1H, dd), 3.77 (1H, dd), 3.96 (2H, s), 4.46 (1H, d), 6.65 (1H, d), 6.68-6.71 (1H, m), 6.78 (1H, dd), 6.91 (1H, dd), 7.06 (1H, dd), 7.16 (1H, d)<br>ES-MS (m/z); 351 [M − H]$^-$ |

TABLE 34-continued

| Ex. | STRUCTURE | DATA |
|---|---|---|
| 176 | 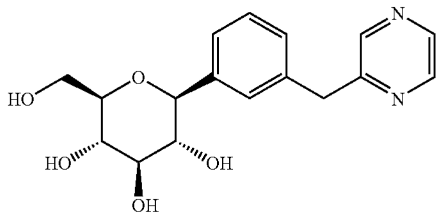 | $^1$H-NMR (CD$_3$OD); 3.36-3.56 (5H, m), 3.77 (1H, dd), 4.16 (1H, d), 4.20 (2H, s), 7.19-7.37 (4H, m), 8.42 (1H, d), 8.49 (2H, d) EI-MS (m/z); 332 [M]$^+$ |
| 177 | 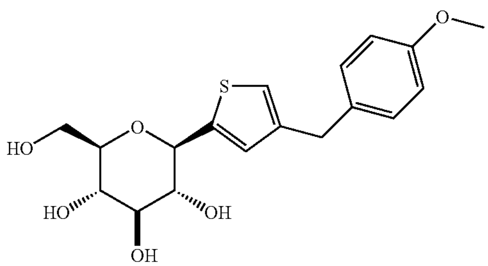 | $^1$H-NMR (CD$_3$OD); 3.29-3.44 (4H, m), 3.64 (1H, dd), 3.75 (3H, s), 3.82-3.90 (3H, m), 4.33 (1H, d), 6.81 (2H, d), 6.92 (2H, s), 7.11 (2H, d) FAB-MS (m/z); 365 [M − H]$^−$ |
| 178 | 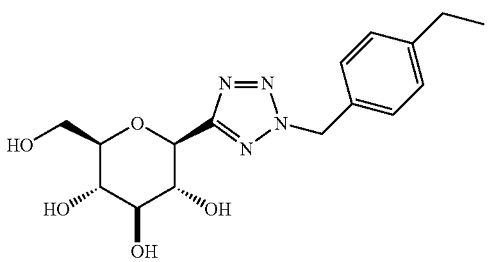 | $^1$H-NMR (CD$_3$OD); 1.20 (3H, t), 2.63 (2H, dd), 3.34-3.86 (6H, m), 4.56 (1H, d), 4.84 (2H, s), 7.21 (2H, d), 7.32 (2H, d) FAB-MS (m/z); 351 [M + H]$^+$ |
| 179 | 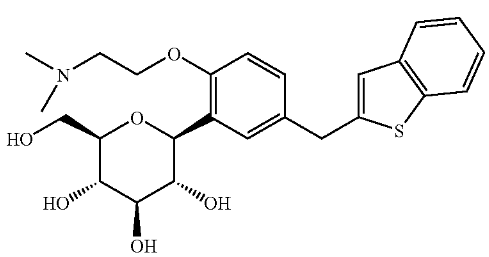 | $^1$H-NMR (CD$_3$OD); 2.27 (6H, s), 2.61-2.75 (2H, m), 3.28 (1H, t), 3.36-3.47 (2H, m), 3.68 (1H, d), 4.01-4.10 (4H, m), 4.18 (2H, s), 4.52 (1H, d), 6.95 (1H, d), 7.15-7.21 (2H, m), 7.23-7.34 (3H, m), 7.73 (1H, d), 7.83 (1H, d) FAB-MS (m/z); 474 [M + H]$^+$ |
| 180 | 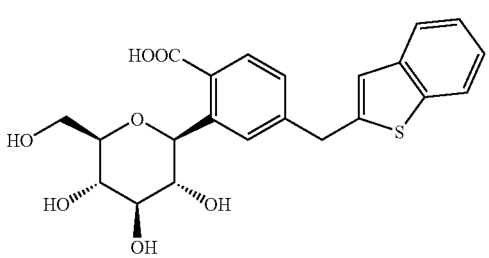 | $^1$H-NMR (CD$_3$OD); 3.31-3.54 (4H, m), 3.72 (1H, dd), 3.88 (1H, dd), 4.30 (2H, s), 5.19 (1H, d), 7.08 (1H, s), 7.20-7.35 (3H, m), 7.68 (1H, d), 7.71-7.80 (3H, m) FAB-MS (m/z); 429 [M − H]$^−$ |

TABLE 35

| Ex. | STRUCTURE | DATA |
| --- | --- | --- |
| 181 | 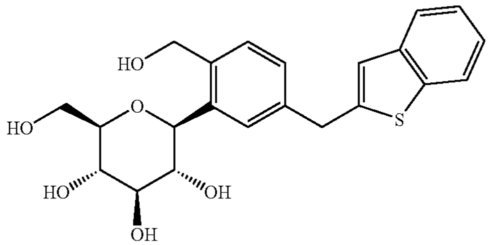 | ¹H-NMR (CD₃OD); 3.38-3.53 (4H, m), 3.68 (1H, dd), 3.88 (1H, dd), 4.24 (2H, s), 4.55 (1H, d), 4.66 (1H, d), 4.73 (1H, d), 7.06 (1H, d), 7.19-7.30 (3H, m), 7.34 (1H, d), 7.54 (1H, d), 7.63-7.74 (2H, m)<br>FAB-MS (m/z); 415 [M − H]⁻ |
| 182 | 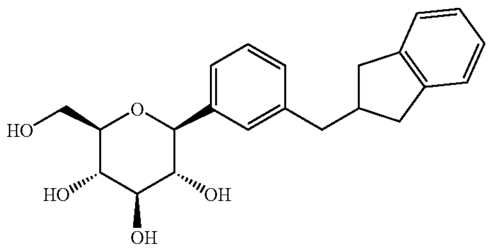 | ¹H-NMR (CD₃OD); 2.61-2.97 (5H, m), 3.54-3.79 (6H, m), 4.07 (1H, d), 4.17-4.95 (4H, m), 7.03-7.24 (7H, m), 7.51 (1H, s)<br>EI-MS (m/z); 370 [M]⁺ |
| 183 | 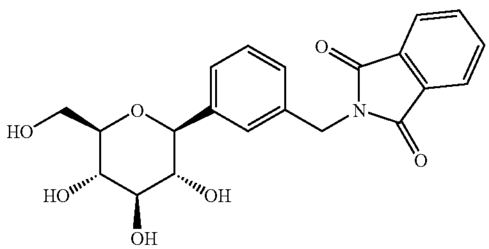 | ¹H-NMR (CD₃OD); 3.34-3.51 (4H, m), 3.66-3.70 (1H, m), 3.87 (1H, dd), 4.13 (1H, d), 4.40 (2H, s), 7.26 (1H, d), 7.31-7.40 (3H, m), 7.48-7.52 (2H, m), 7.57-7.61 (1H, m), 7.81 (1H, d). |
| 184 | 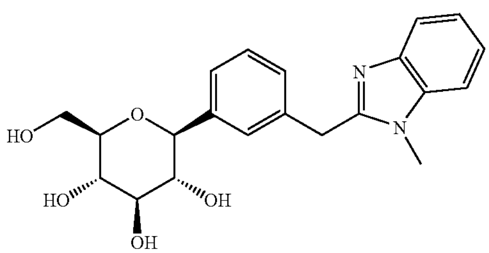 | ¹H-NMR (CD₃OD); 3.29-3.50 (4H, m), 3.64-3.70 (1H, m), 3.70 (3H, s), 3.86 (1H, dd), 4.09 (1H, d), 4.35 (2H, s), 7.18 (1H, d), 7.21-7.37 (5H, m), 7.43 (1H, dd), 7.60 (1H, dd)<br>FAB-MS (m/z); 385 [M + H]⁺ |
| 185 | 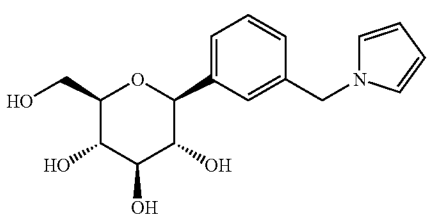 | ¹H-NMR (CD₃OD); ¹H-NMR (CD₃OD); 3.32-3.50 (4H, m), 3.69 (1H, dd), 3.84 (1H, dd), 4.10 (1H, d), 5.07 (1H, d), 6.05 (2H, t), 6.70 (2H, t), 7.05 (1H, d), 7.25-7.35 (3H, m)<br>FAB-MS (m/z); 320 [M + H]⁺ |
| 186 | 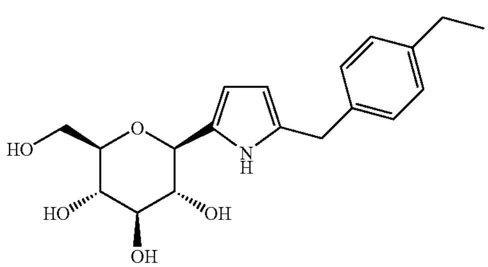 | ¹H-NMR (CD₃OD); 1.19 (3H, t), 2.58 (2H, q), 3.24-3.46 (4H, m), 3.65 (1H, dd), 3.80-3.86 (3H, m), 4.15 (1H, d), 5.73 (1H, d), 6.02 (1H, d), 7.07 (1H, d), 7.12 (1H, d)<br>FAB-MS (m/z); 348 [M + H]⁺ |

TABLE 36

| Ex. | STRUCTURE | DATA |
|---|---|---|
| 187 | (structure) | $^1$H-NMR (CD$_3$OD); 1.10 (3H, t), 2.49 (2H, q), 3.19-3.63 (7H, m), 3.70-3.83 (4H, m), 4.16 (1H, d), 5.71 (1H, d), 6.01 (1H, d), 6.95 (1H, d), 6.98 (1H, d) FAB-MS (m/z); 360 [M − H]$^-$ |
| 188 | (structure) | $^1$H-NMR (CD$_3$OD); 1.20 (3H, t), 2.60 (2H, q), 3.20-3.39 (3H, m), 3.56 (1H, dd), 3.66 (1H, dd), 3.73 (1H, dd), 4.17 (1H, d), 5.13 (1H, d), 5.22 (1H, d), 6.06 (1H, dd), 6.23 (1H, dd), 6.70 (1H, dd), 7.06 (2H, d), 7.13 (2H, d) FAB-MS (m/z); 348 [M + H]$^+$ |

TABLE 37

TABLE 37-continued
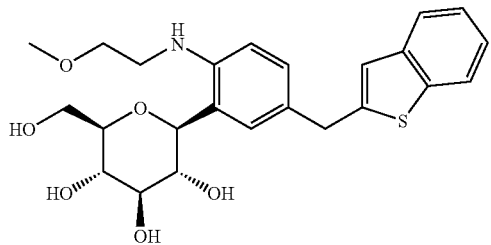
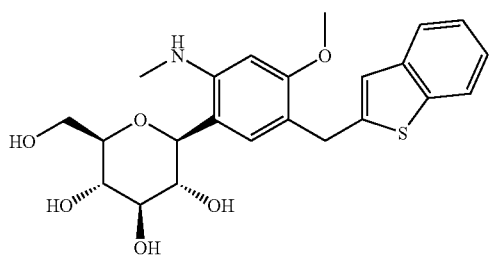
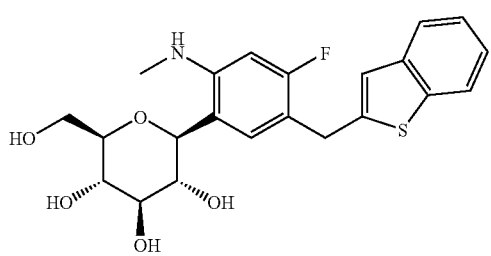
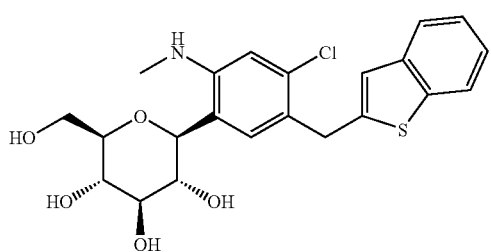
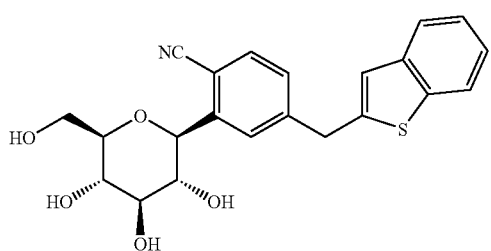
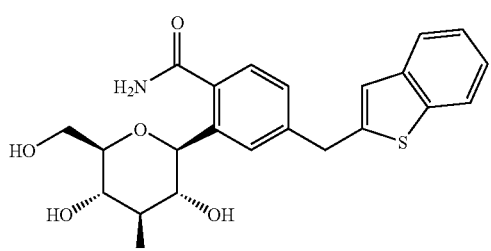
TABLE 37-continued
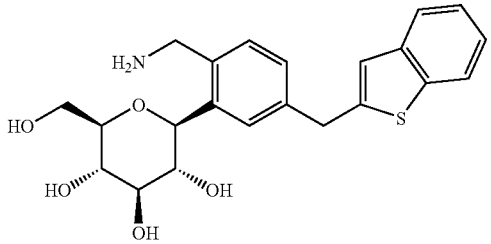
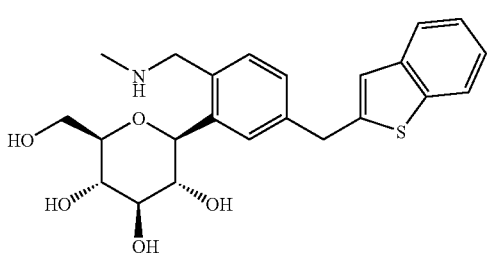
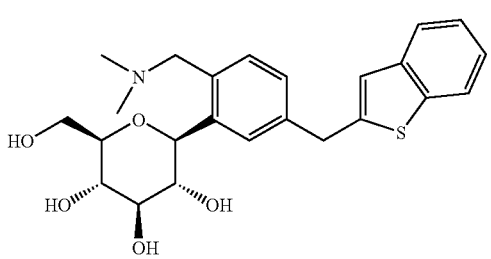
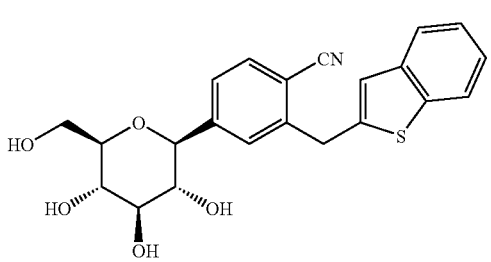
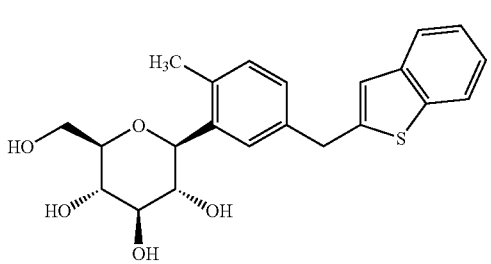
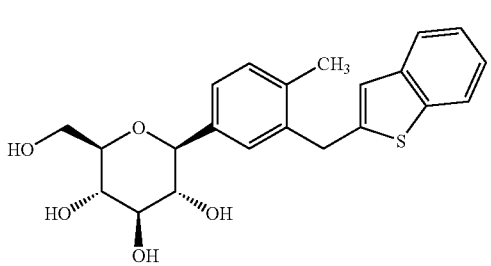

TABLE 37-continued
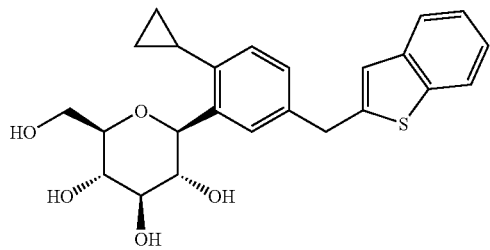
TABLE 38
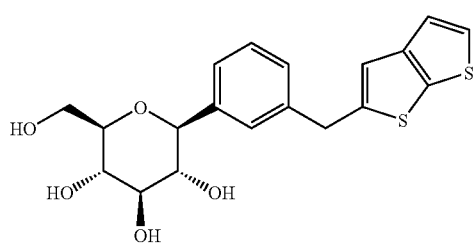
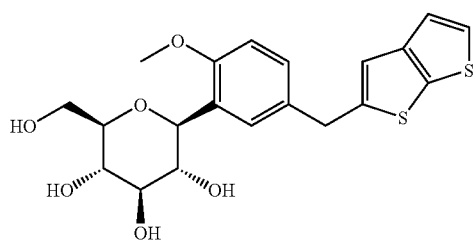
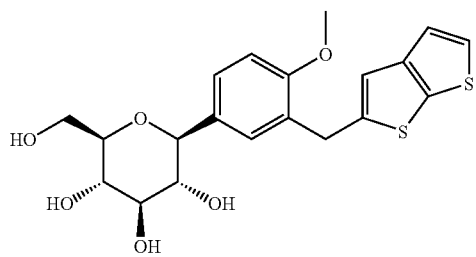
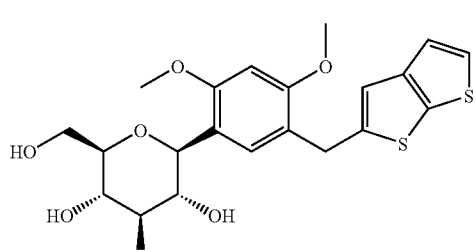
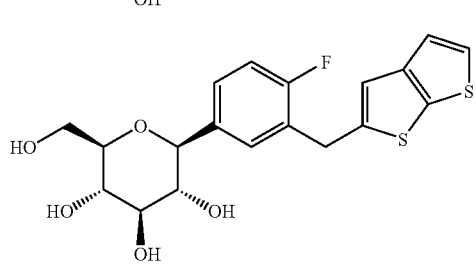
TABLE 38-continued
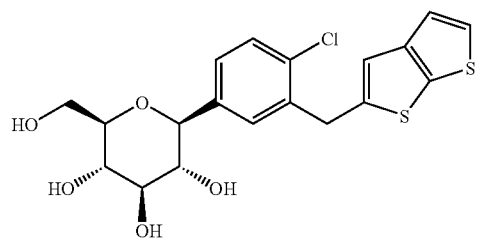
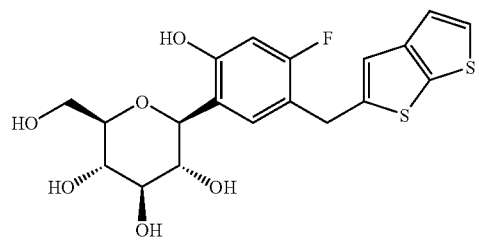
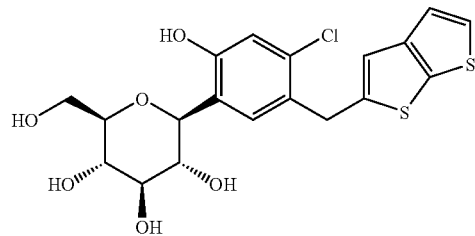
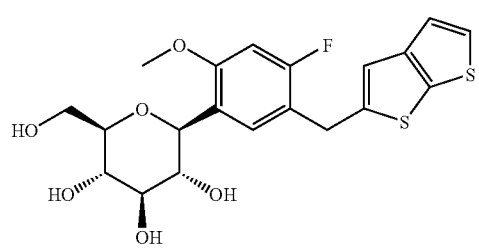
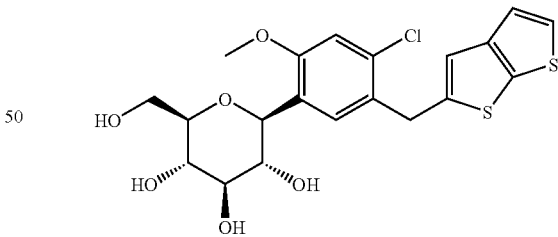
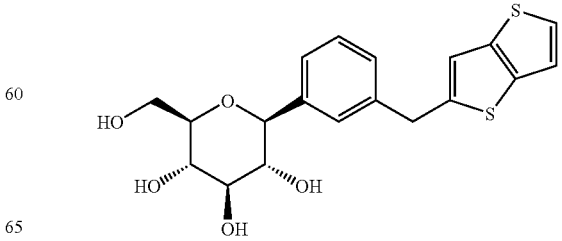

TABLE 38-continued
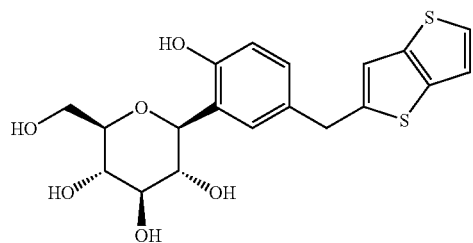
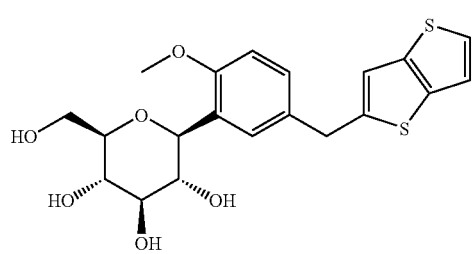
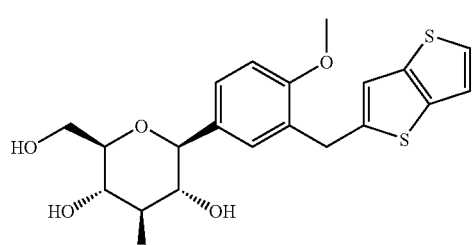
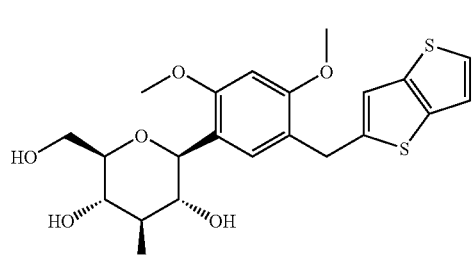
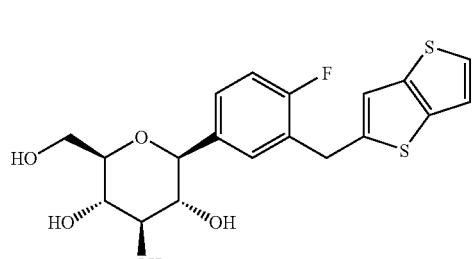
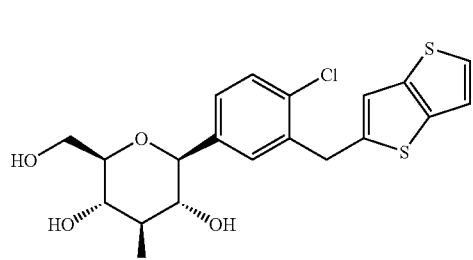
TABLE 38-continued
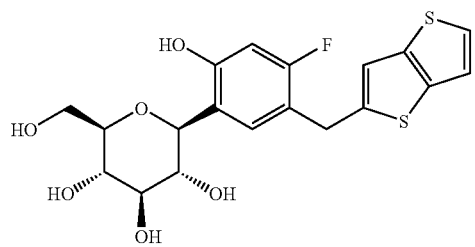
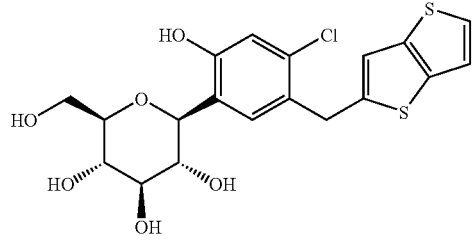
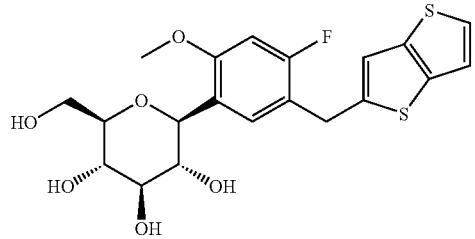
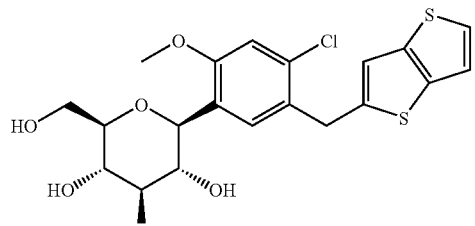
TABLE 39
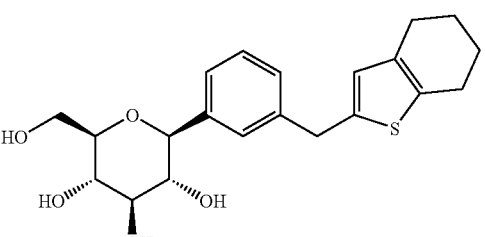
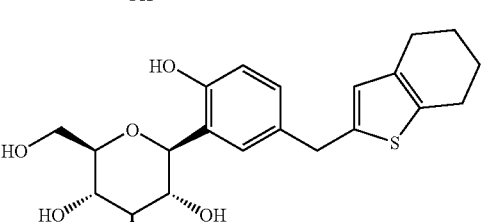

TABLE 39-continued
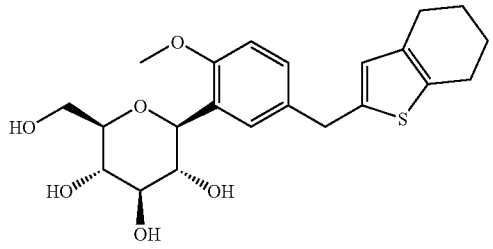
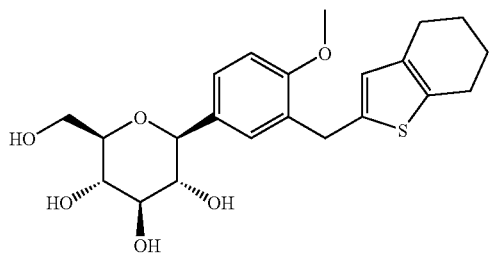
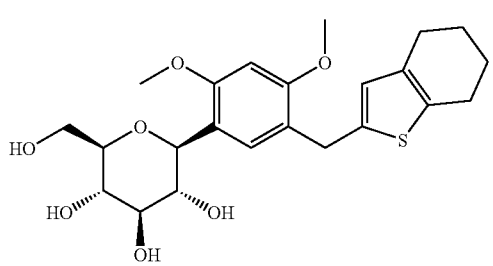
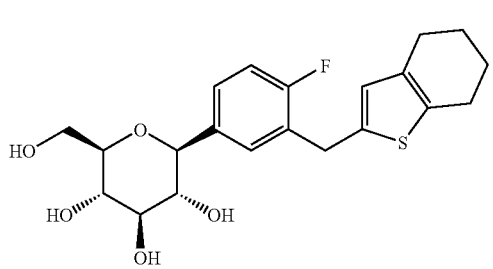
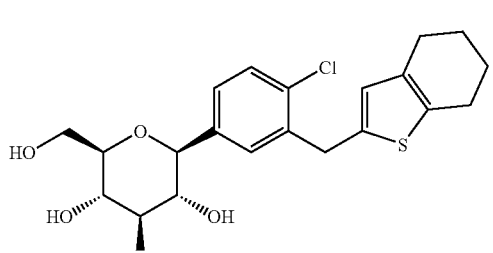
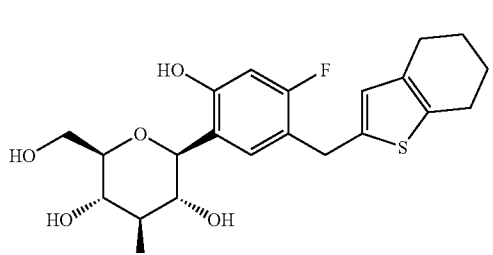
TABLE 39-continued
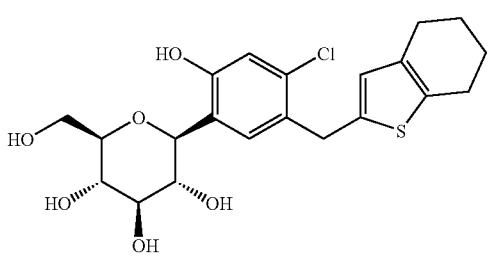
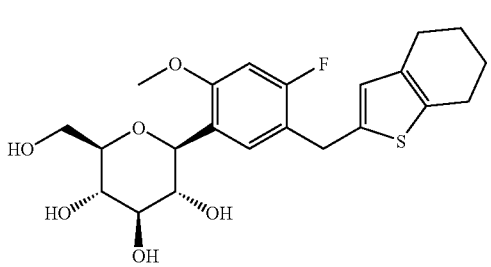
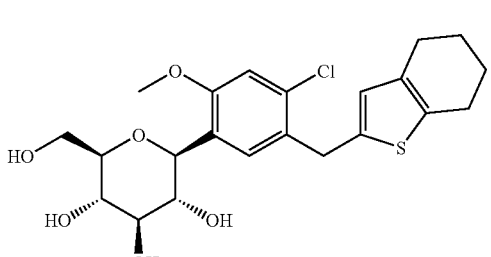
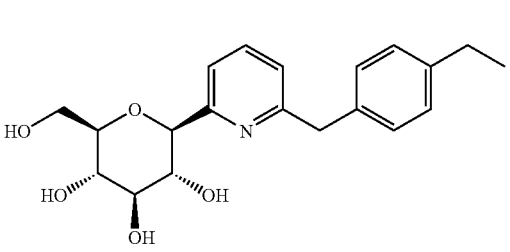
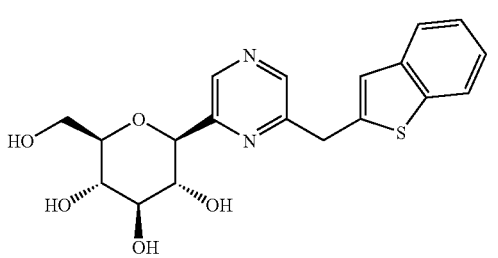
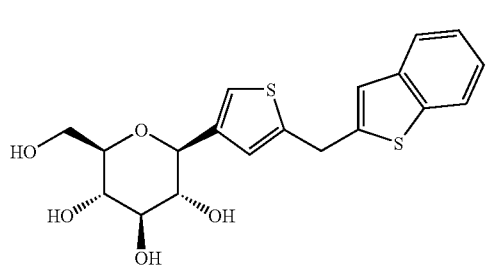

TABLE 39-continued

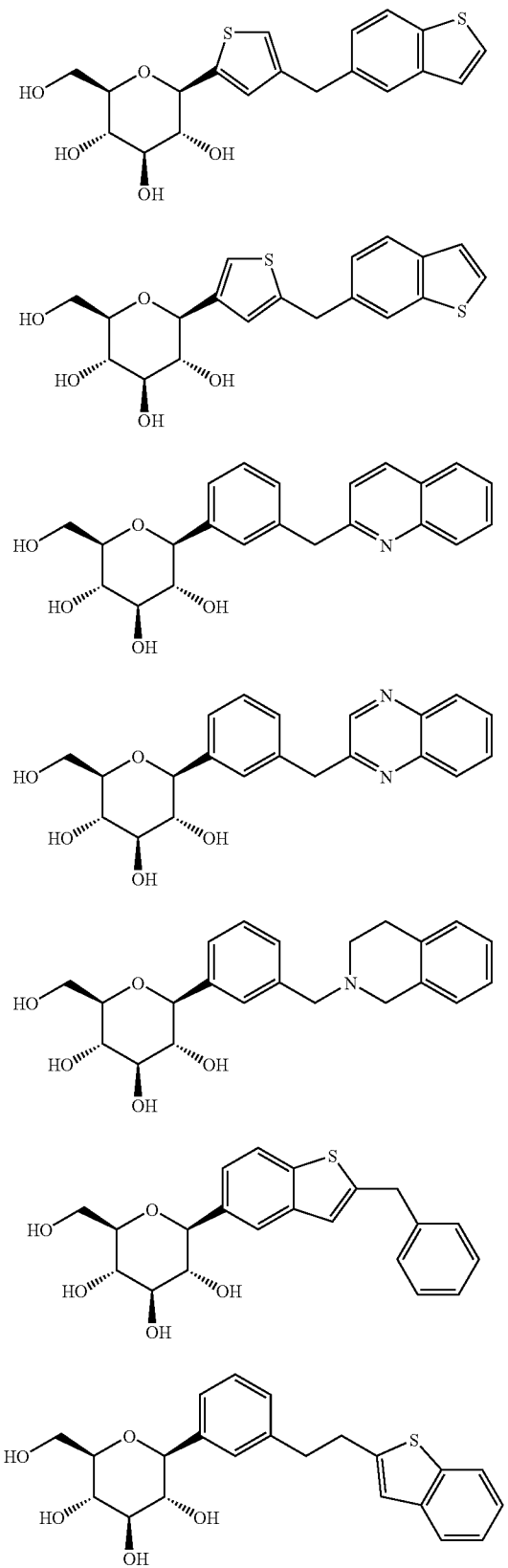

The invention claimed is:

1. A C-glycoside derivative of the following formula (I) or a salt thereof:

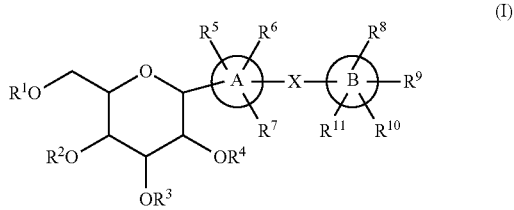

(I)

wherein;

A ring represents a benzene ring;

X represents methylene;

B ring represents a saturated or unsaturated eight to ten-membered bicyclic hetero ring which has 1 to 4 hetero atom(s) selected from N, S, and O and includes a benzene ring, and X is bonded to the B ring in a part other than the benzene ring included in the B ring;

$R^1$ to $R^4$ individually represent a hydrogen atom, a lower alkyl, —C(=O)-lower alkyl, or -lower alkylene-aryl;

$R^8$, $R^9$ and $R^{11}$ individually represent a hydrogen atom; and

—$R^5$, $R^6$, $R^7$, and $R^{10}$ individually represent a hydrogen atom, a lower alkyl, a halogen, a halogen-substituted lower alkyl, —OH, =O, —$NH_2$, lower alkyl sulfonyl-, aryl sulfonyl-, -lower alkylene-OH, -lower alkylene-O-lower alkyl, -lower alkylene-O—C(=O)-lower alkyl, —COOH, —CN, —C(=O)—O-lower alkyl, —O-lower alkyl, —O-lower alkylene-OH, —O-lower alkylene-O-lower alkyl, —O-lower alkylene-COOH, —O-lower alkylene-C(=O)—O-lower alkyl, or —O-lower alkylene-$NH_2$.

2. The C-glycoside derivative or the salt thereof according to claim 1, wherein the $R^1$ to $R^4$ in the formula (I) are hydrogen atoms.

3. The C-glycoside derivative or the salt thereof according to claim 1, wherein the C-glycoside derivative of the formula (I) is at least one compound selected from the group consisting of (1S)-1,5-anhydro-1-[3-(1-benzothien-2-ylmethyl)phenyl]-D-glucitol, (1S)-1,5-anhydro-1-[5-(1-benzothien-2-ylmethyl)-2-hydroxyphenyl]-D-glucitol, (1S)-1,5-anhydro-1-[5-(1-benzothien-2-ylmethyl)-2-methoxyphenyl]-D-glucitol, (1S)-1,5-anhydro-1-[5-(1-benzothien-2-ylmethyl)-2-(2-hydroxyethoxy)phenyl]-D-glucitol, (1S)-1,5-anhydro-1-[5-(1-benzothien-2-ylmethyl)-4-methoxyphenyl]-D-glucitol, (1S)-1,5-anhydro-1-[5-(1-benzothien-2-ylmethyl)-4-chlorophenyl]-D-glucitol, (1S)-1,5-anhydro-1-[5-(1-benzothien-2-ylmethyl)-4-fluorophenyl]-D-glucitol, (1S)-1,5-anhydro-1-[5-(1-benzothien-2-ylmethyl)-2,4-dimethoxyphenyl]-D-glucitol, (1S)-1,5-anhydro-1-[5-(1-benzothien-2-ylmethyl)-4-chloro-2-methoxyphenyl]-D-glucitol, (1S)-1,5-anhydro-1-[5-(1-benzothien-2-ylmethyl)-4-chloro-2-hydroxyphenyl]-D-glucitol, (1S)-1,5-anhydro-1-[5-(1-benzothien-2-ylmethyl)-4-fluoro-2-hydroxyphenyl]-D-glucitol, and (1S)-1,5-anhydro-1-[5-(1-benzothien-2-ylmethyl)-4-fluoro-2-methoxyphenyl]-D-glucitol.

4. A pharmaceutical composition containing a C-glycoside derivative or a salt thereof according to claim 2, and a pharmaceutically acceptable carrier or diluent.

5. A method for treating diabetes comprising administering an effective amount of the C-glycoside derivative or the salt thereof according to claim 2, to a patient in need thereof.

6. A pharmaceutical composition containing a C-glycoside derivative or a salt thereof according to claim 3 and a pharmaceutically acceptable carrier or diluent.

7. A method for treating diabetes comprising administering an effective amount of the C-glycoside derivative or the salt thereof according to claim 3 to a patient in need thereof.

* * * * *